(12) United States Patent
Maynard et al.

(10) Patent No.: US 11,951,176 B2
(45) Date of Patent: Apr. 9, 2024

(54) STABILIZATION OF GLUCAGON BY TREHALOSE GLYCOPOLYMER NANOGELS

(71) Applicant: The Regents of the University of California, Oakland, CA (US)

(72) Inventors: Heather D. Maynard, Los Angeles, CA (US); Natalie Boehnke, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 498 days.

(21) Appl. No.: 16/771,588

(22) PCT Filed: Nov. 30, 2018

(86) PCT No.: PCT/US2018/063225
§ 371 (c)(1),
(2) Date: Jun. 10, 2020

(87) PCT Pub. No.: WO2019/118202
PCT Pub. Date: Jun. 20, 2019

(65) Prior Publication Data
US 2020/0297866 A1    Sep. 24, 2020

Related U.S. Application Data

(60) Provisional application No. 62/597,033, filed on Dec. 11, 2017.

(51) Int. Cl.
| | |
|---|---|
| A61K 47/58 | (2017.01) |
| A61K 47/69 | (2017.01) |
| C07K 14/605 | (2006.01) |
| C08F 8/34 | (2006.01) |
| C08F 220/28 | (2006.01) |
| C08F 220/38 | (2006.01) |
| C08G 81/02 | (2006.01) |
| A61K 38/00 | (2006.01) |

(52) U.S. Cl.
CPC .......... *A61K 47/6903* (2017.08); *A61K 47/58* (2017.08); *C07K 14/605* (2013.01); *C08F 8/34* (2013.01); *C08F 220/282* (2020.02); *C08F 220/385* (2020.02); *C08G 81/025* (2013.01); *A61K 38/00* (2013.01); *C08F 2800/10* (2013.01); *C08F 2810/20* (2013.01)

(58) Field of Classification Search
CPC .... A61K 47/6903; A61K 47/58; A61K 38/00; C08F 20/10; C08F 20/26; C08F 20/28; C08F 220/10; C08F 220/26; C08F 220/28; C08F 220/282; C08F 224/00; C08F 24/00; C08F 20/38; C08F 220/38; C08F 220/385
See application file for complete search history.

(56) References Cited

U.S. PATENT DOCUMENTS

2017/0240711 A1    8/2017  Maynard

FOREIGN PATENT DOCUMENTS

| WO | 2016025668 A1 | 2/2016 |
| WO | WO2016025551 A1 * | 2/2016 |

OTHER PUBLICATIONS

Boehnke, Natalie. Degradable Hydrogels and Nanogels for the Delivery of Cells and Therapuetics pp. 81-151 (Year: 2017).*
Ryu, J. H., et al. (2010). Self-cross-linked polymer nanogels: a versatile nanoscopic drug delivery platform. Journal of the American Chemical Society, 132(48), 17227-17235.
Ryu, J. H., et al. (2010). Surface-functionalizable polymer nanogels with facile hydrophobic guest encapsulation capabilities. Journal of the American Chemical Society, 132(24), 8246-8247.
Sakurai, M. (2009). Biological functions of trehalose as a substitute for water. In Water and Biomolecules (pp. 219-240). Springer, Berlin, Heidelberg.
Sizovs, A., et al. "Poly (trehalose): sugar-coated nanocomplexes promote stabilization and effective polyplex-mediated siRNA delivery." Journal of the American Chemical Society 135.41 (2013): 15417-15424.
Sola-Penna, M., et al. (1998). Stabilization against thermal inactivation promoted by sugars on enzyme structure and function: why is trehalose more effective than other sugars ?. Archives of biochemistry and biophysics, 360(1), 10-14.
Stigsnaes, P., et al. (2007). Characterisation and physical stability of PEGylated glucagon. International journal of pharmaceutics, 330(1-2), 89-98.
Sueiras-Diaz, J., et al. (1984). Structure activity studies on the N-terminal region of glucagon. Journal of medicinal chemistry, 27(3), 310-315.
Tapia, H., et al. (2014). Trehalose is a versatile and long-lived chaperone for desiccation tolerance. Current Biology, 24(23), 2758-2766.
Tapia, H., et al. (2015). Increasing intracellular trehalose is sufficient to confer desiccation tolerance to *Saccharomyces cerevisiae*. Proceedings of the National Academy of Sciences of the United States of America, 112 (19), 6122.
Tolstyka, Z. P., et al. "Trehalose-based block copolycations promote polyplex stabilization for lyophilization and in vivo pDNA Delivery." ACS biomaterials science & engineering 2.1 (2016): 43-55.
Unger, R. H. "Glucagon physiology and pathophysiology in the light of new advances." Diabetologia 28.8 (1985): 574-578.

(Continued)

*Primary Examiner* — Irina S Zemel
*Assistant Examiner* — Jeffrey S Lenihan
(74) *Attorney, Agent, or Firm* — Quarles & Brady LLP

(57) ABSTRACT

Trehalose-based nanogels for stabilizing and controlled releasing biomolecules such as glucagons are disclosed. Specifically, trehalose-based nanogels comprise (a) a copolymer comprising first methacrylate units and second methacrylate units, wherein (i) the first methacrylate units comprise trehalose side chains; and (ii) the second methacrylate units comprise disulfide side chains; (b) dithiol cross-linkers; wherein the dithiol cross-linkers cross link the copolymer through the disulfide side chains of the second methacrylate units.

17 Claims, 29 Drawing Sheets

(56) References Cited

OTHER PUBLICATIONS

Ventura, J., et al. (2015). Reactive self-assembly of polymers and proteins to reversibly silence a killer protein. Biomacromolecules, 16(10), 3161-3171.
Webber, M. J., et al. (2016). Supramolecular PEGylation of biopharmaceuticals. Proceedings of the National Academy of Sciences, 113(50), 14189-14194.
Wendorf, J. R., et al. (2004). Reduced protein adsorption at solid interfaces by sugar excipients. Biotechnology and bioengineering, 87(5), 565-573.
Winther, J. R., et al. (2014). Quantification of thiols and disulfides. Biochimica et Biophysica Acta (BBA)-General Subjects, 1840(2), 838-846.
Yi, X., et al. (2008). Protein conjugation with amphiphilic block copolymers for enhanced cellular delivery. Bioconjugate chemistry, 19(5), 1071-1077.
Authier, F., et al. (2008). Glucagon receptors. Cellular and Molecular Life Sciences, 65(12), 1880-1899.
Bat, E., et al. (2015). Trehalose glycopolymer resists allow direct writing of protein patterns by electron-beam lithography. Nature communications, 6(1), 1-8.
Belton, P. S., et al. (1994). IR and Raman spectroscopic studies of the interaction of trehalose with hen egg white lysozyme. Biopolymers: Original Research on Biomolecules, 34(7), 957-961.
Boehnke, N., et al. (2018). Stabilization of Glucagon by Trehalose Glycopolymer Nanogels. Advanced Functional Materials, 28(10), 1705475.
Bromer, W. W., et al. (1956). The amino acid sequence of glucagon. Journal of the American Chemical Society, 78 (15), 3858-3860.
Caputo, N., et al. (2013). Mechanisms of glucagon degradation at alkaline pH. Peptides, 45, 40-47.
Chabenne, J. R., et al. (2010). Glucagon: Physiology and Pharmacotherapy: Optimization of the Native Glucagon Sequence for Medicinal Purposes. Journal of Diabetes Science and Technology, 4(6), 1322.
Chabenne, J., et al. (2014). A glucagon analog chemically stabilized for immediate treatment of life-threatening hypoglycemia. Molecular metabolism, 3(3), 293-300.
Chang, C. W., et al. (2009). Differences in cytotoxicity of poly (PEGA) s synthesized by reversible addition-fragmentation chain transfer polymerization. Chemical communications, (24), 3580-3582.
Charulatha, V., et al. "Dimethyl 3, 3'-dithiobispropionimidate: A novel crosslinking reagent for collagen." Journal of Biomedical Materials Research 54 (2001): 122-128.
Christie, R. J., et al. (2011). Effect of polymer structure on micelles formed between siRNA and cationic block copolymer comprising thiols and amidines. Biomacromolecules, 12(9), 3174-3185.
Cottone, G., et al. (2002). Protein-trehalose-water structures in trehalose coated carboxy-myoglobin. The Journal of chemical physics, 117(21), 9862-9866.
Crowe, J. H., et al. (1998). The role of vitrification in anhydrobiosis. Annual review of physiology, 60(1), 73-103.
Cryer, P. E., et al. (2003). Hypoglycemia in diabetes. Diabetes care, 26(6), 1902-1912.
Dutta, K., et al. (2017). Templated self-assembly of a covalent polymer network for intracellular protein delivery and traceless release. Journal of the American Chemical Society, 139(16), 5676-5679.
Eroglu, A., et al. (2000). Intracellular trehalose improves the survival of cryopreserved mammalian cells. Nature biotechnology, 18(2), 163-167.
Fang, W.-J., et al. "Effects of excipients on the chemical and physical stability of glucagon during freeze-drying and storage in dried formulations." Pharmaceutical research 29.12 (2012): 3278-3291.
Ghodke, S., et al. (2012). Mapping out the multistage fibrillation of glucagon. The FEBS journal, 279(5), 752-765.

Ghosh, S., et al. (2006). Simultaneous and reversible functionalization of copolymers for biological applications. Macromolecules, 39(17), 5595-5597.
Guo, N., et al. (2000). Trehalose expression confers desiccation tolerance on human cells. Nature biotechnology, 18 (2), 168-171.
Herdeiro, R. S., et al. (2006). Trehalose protects *Saccharomyces cerevisiae* from lipid peroxidation during oxidative stress. Biochimica et Biophysica Acta (BBA)-General Subjects, 1760(3), 340-346.
Hunter, M. J., et al. (1962). The reaction of imidoesters with proteins and related small molecules. Journal of the American Chemical Society, 84(18), 3491-3504.
International Searching Authority. International Search Report and Written Opinion for application PCT/US2018/063225. dated Feb. 11, 2019.
Jain, N. K., et al. (2009). Effect of trehalose on protein structure. Protein Science, 18(1), 24-36.
Joshi, A. B., et al. (2002). The relative rates of glutamine and asparagine deamidation in glucagon fragment 22-29 under acidic conditions. Journal of pharmaceutical sciences, 91(11), 2332-2345.
Kabanov, A. V., et al. (2009). Nanogels as pharmaceutical carriers: finite networks of infinite capabilities. Angewandte Chemie International Edition, 48(30), 5418-5429.
Kale, S. S., et al. (2016). Trehalose monooleate: a potential antiaggregation agent for stabilization of proteins. Molecular Pharmaceutics, 13(12), 4082-4093.
Kaushik, J. K., et al. (2003). Why is trehalose an exceptional protein stabilizer? An analysis of the thermal stability of proteins in the presence of the compatible osmolyte trehalose. Journal of Biological Chemistry, 278(29), 26458-26465.
Koth, C. M., et al. "Molecular basis for negative regulation of the glucagon receptor." Proceedings of the National Academy of Sciences 109.36 (2012): 14393-14398.
Lau, U. Y., et al. (2016). Direct write protein patterns for multiplexed cytokine detection from live cells using electron beam lithography. ACS nano, 10(1), 723-729.
Lee, J., et al. (2013). Trehalose glycopolymers as excipients for protein stabilization. Biomacromolecules, 14(8), 2561-2569.
Lee, J., et al. (2015). Trehalose hydrogels for stabilization of enzymes to heat. Polymer chemistry, 6(18), 3443-3448.
Li, L., et al. (2013). Surface charge generation in nanogels for activated cellular uptake at tumor-relevant pH. Chemical Science, 4(9), 3654-3660.
Liu, Y., et al. (2017). Trehalose glycopolymer enhances both solution stability and pharmacokinetics of a therapeutic protein. Bioconjugate chemistry, 28(3), 836-845.
Mancini, R. J., et al. (2012). Trehalose glycopolymers for stabilization of protein conjugates to environmental stressors. Journal of the American Chemical Society, 134(20), 8474-8479.
Matilainen, L., et al. (2009). The stability and dissolution properties of solid glucagon/?- cyclodextrin powder. european journal of pharmaceutical sciences, 36(4-5), 412-420.
Matsumoto, N. M., et al. (2013). Synthesis of nanogel-protein conjugates. Polymer chemistry, 4(8), 2464-2469.
Moens, K., et al. "Expression and functional activity of glucagon, glucagon-like peptide I, and glucose-dependent insulinotropic peptide receptors in rat pancreatic islet cells." Diabetes 45.2 (1996): 257-261.
Mokotoff, M., et al. (2001). Caution in the use of 2-iminothiolane (Traut's reagent) as a cross-linking agent for peptides. The formation of N-peptidyl-2-iminothiolanes with bombesin (BN) antagonist (d-Trp6, Leu13-? [CH2NH]—Phe14) BN6- 14 and d-Trp-Gln-Trp-NH2. The Journal of Peptide Research, 57(5), 383-389.
Montero, D., et al. "Intracellular glutathione pools are heterogeneously concentrated." Redox biology 1.1 (2013): 508-513.
Mroz, P. A., et al. (2016). Native Design of soluble, aggregation-resistant bioactive peptides: chemical evolution of human glucagon. ACS chemical biology, 11(12), 3412-3420.
Oh, N., et al. (2014). Endocytosis and exocytosis of nanoparticles in mammalian cells. International journal of nanomedicine, 9(Suppl 1), 51.
Ohtake, S., et al. (2011). Trehalose: current use and future applications. Journal of pharmaceutical sciences, 100(6), 2020-2053.

(56) References Cited

OTHER PUBLICATIONS

Onoue, S., et al. "Mishandling of the therapeutic peptide glucagon generates cytotoxic amyloidogenic fibrils." Pharmaceutical research 21.7 (2004): 1274-1283.

O'Shea, T. M., et al. (2015). Covalent Incorporation of Trehalose within Hydrogels for Enhanced Long-Term Functional Stability and Controlled Release of Biomacromolecules. Advanced healthcare materials, 4(12), 1802-1812.

Pedersen, J. S .. "Glucagon: Physiology and Pharmacotherapy: The Nature of Amyloid-like Glucagon Fibrils." Journal of Diabetes Science and Technology 4.6 (2010): 1357.

Pelegri-O'Day, E. M., et al. (2017). Substituted Polyesters by Thiol-ene Modification: Rapid Diversification for Therapeutic Protein Stabilization. Journal of the American Chemical Society, 139(3), 1145.

Peterson, C. D., et al. (1984). Glucagon therapy for ß-blocker overdose. Drug intelligence & clinical pharmacy, 18 (5), 394-398.

Pinholt, C., et al. (2011). Influence of PEGylation with linear and branched PEG chains on the adsorption of glucagon to hydrophobic surfaces. European journal of pharmaceutics and biopharmaceutics, 77(1), 139-147.

\* cited by examiner

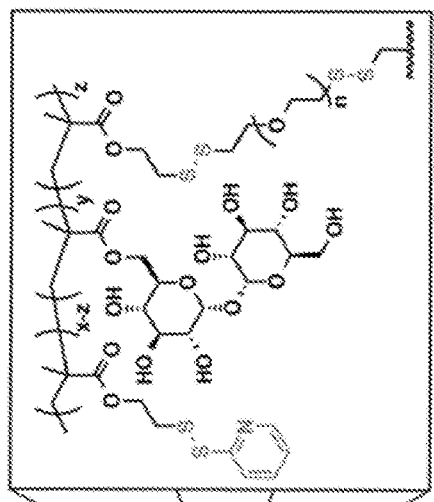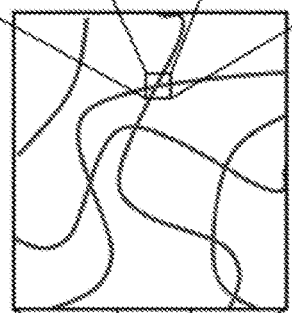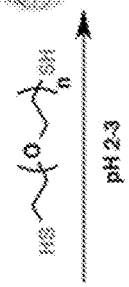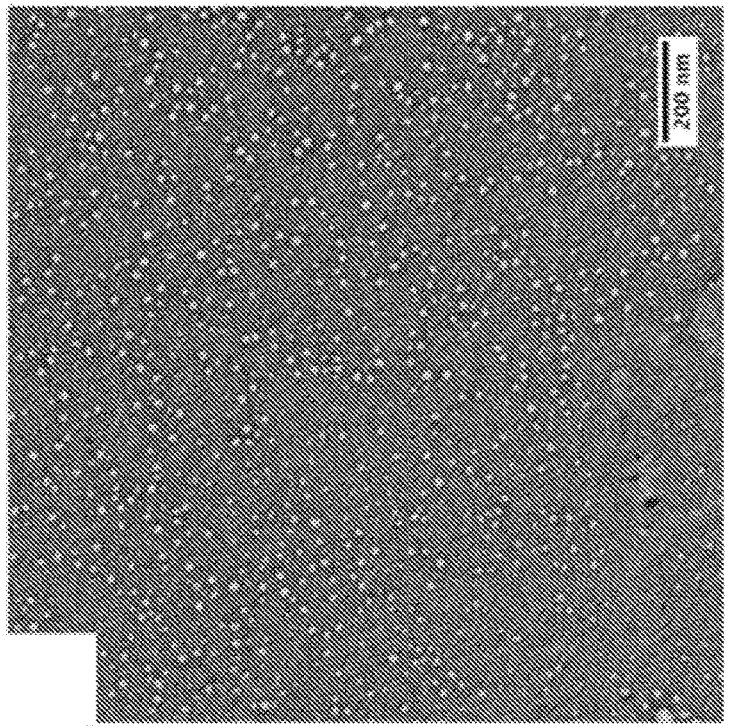
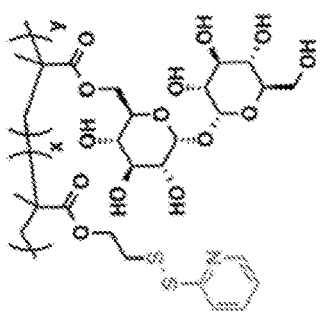
FIG. 1A
FIG. 1C

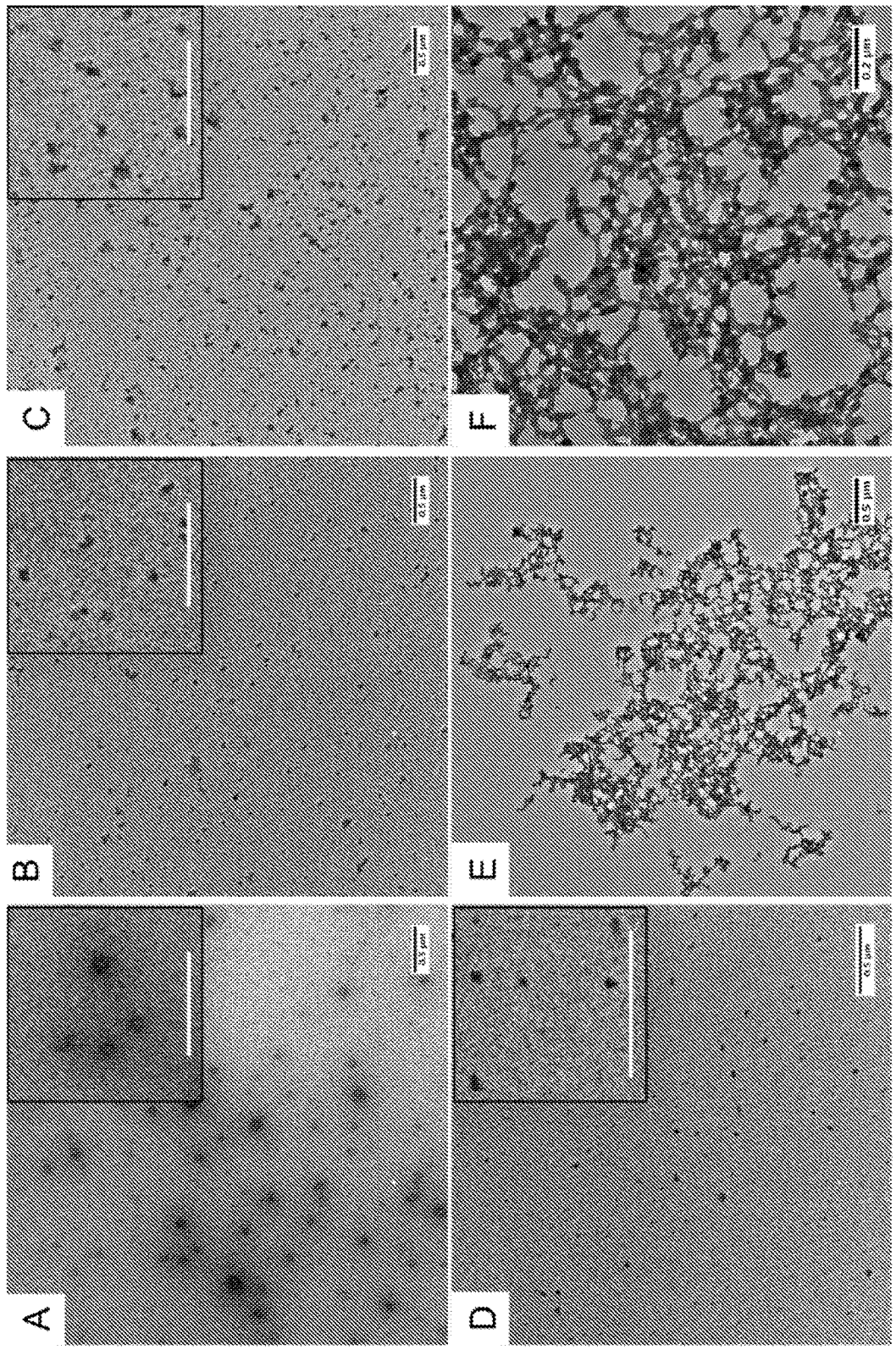
FIGS. 5A-F

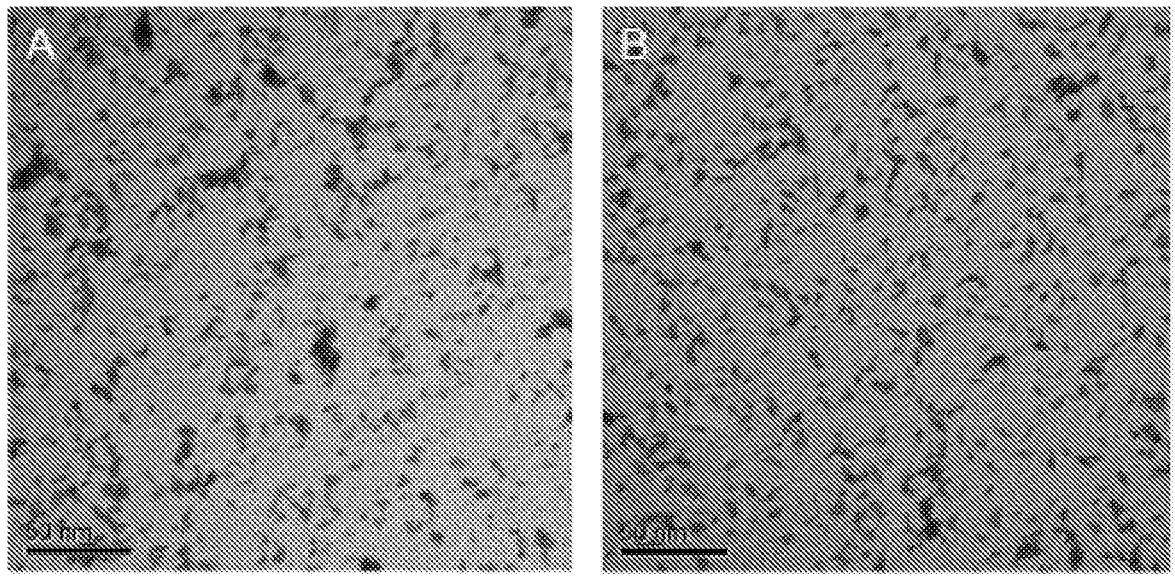
FIGS. 19 A-B
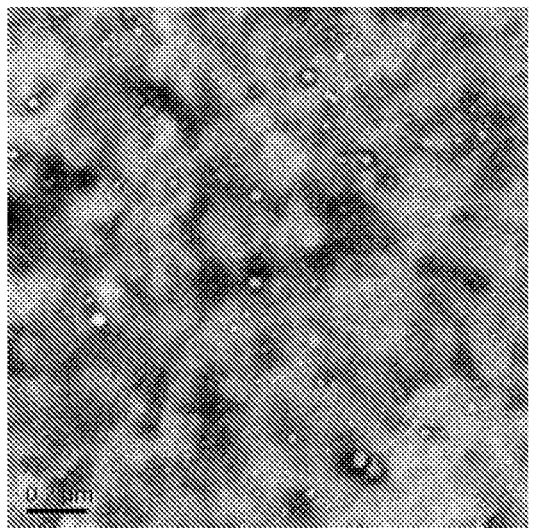
FIG. 20

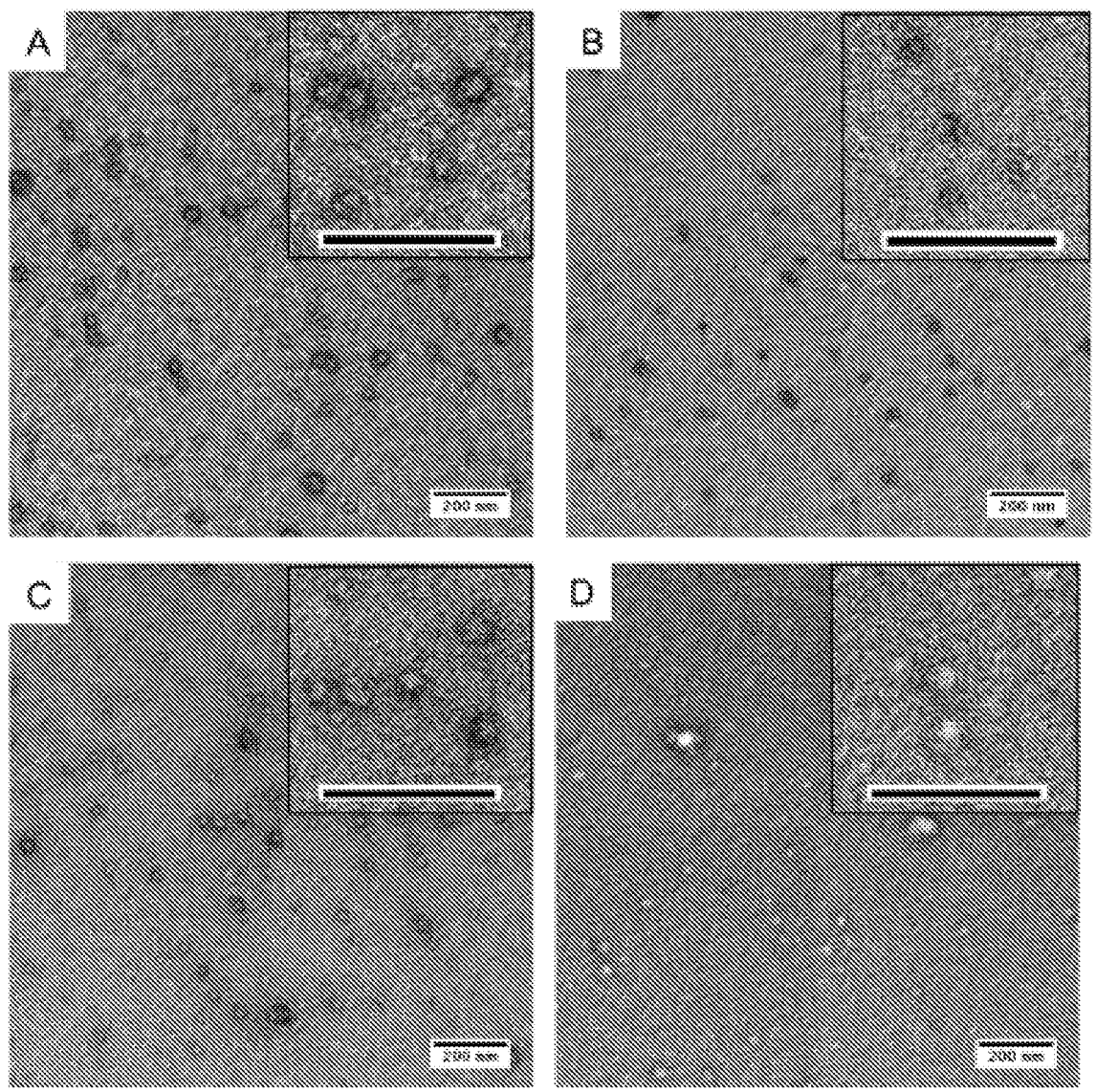
FIGS. 26A-D

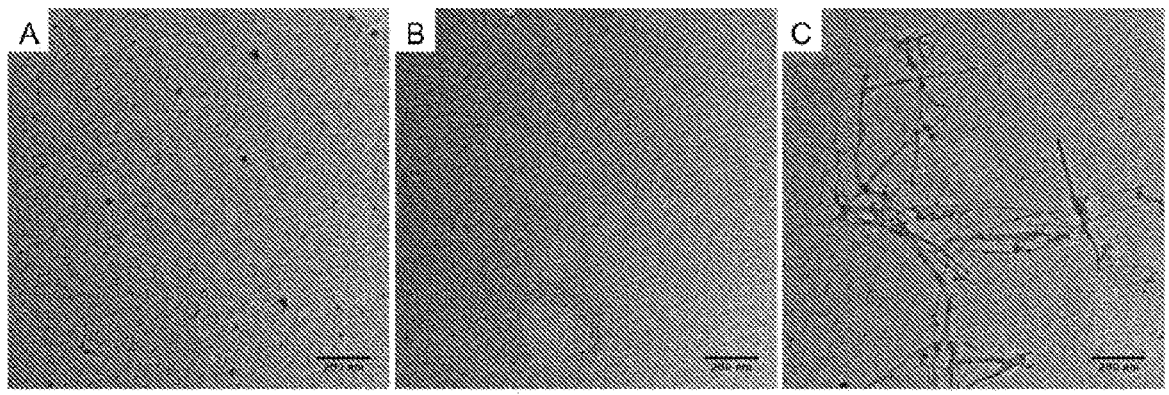
FIGS. 27A-C
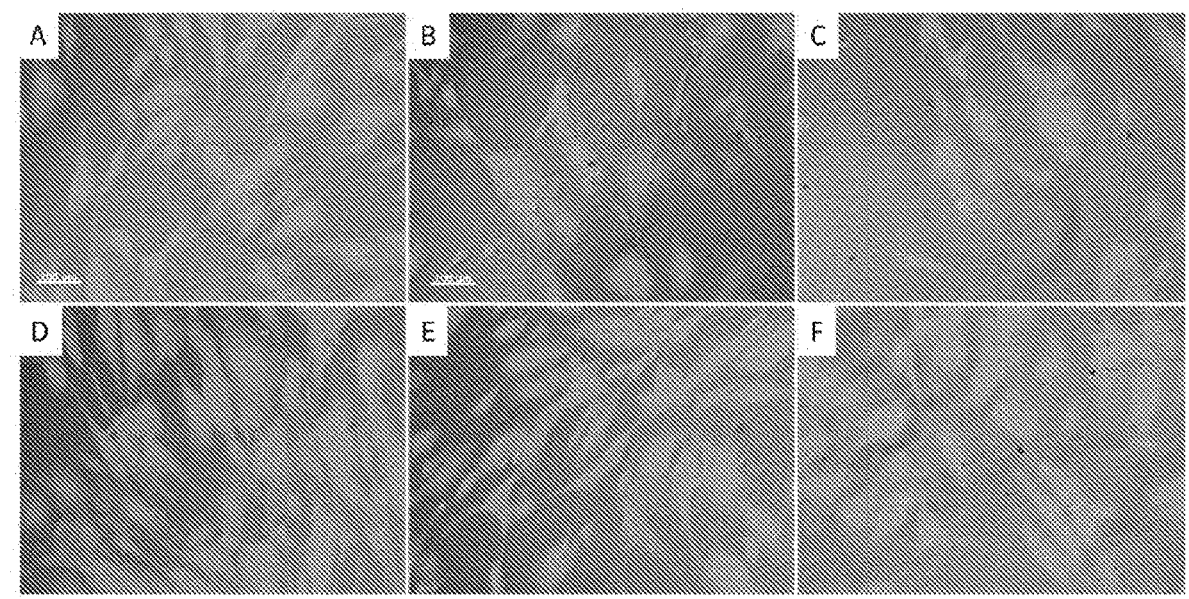
FIGS. 28A-F

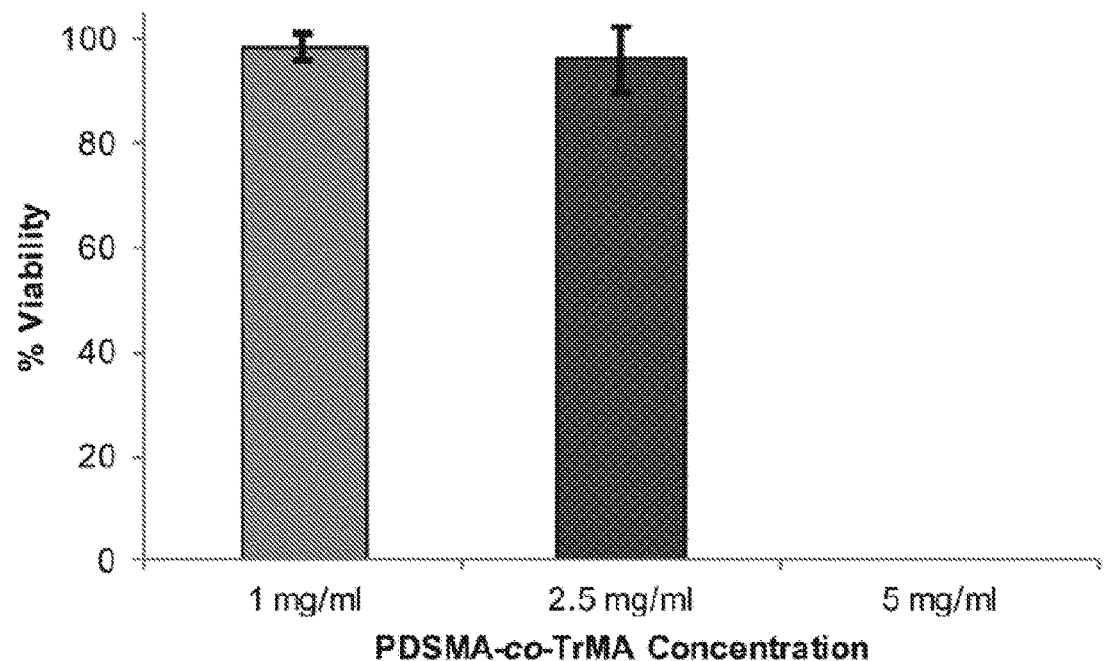
FIG. 29
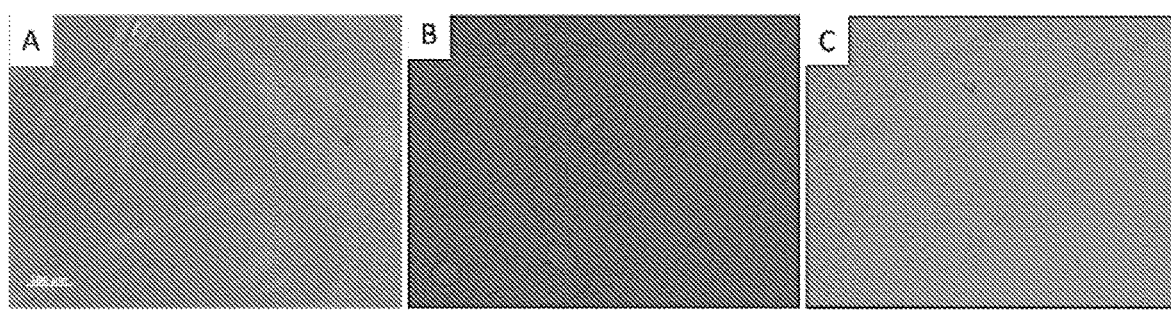
FIGS. 30A-C

STABILIZATION OF GLUCAGON BY TREHALOSE GLYCOPOLYMER NANOGELS

CROSS-REFERENCE TO RELATED APPLICATION

The present application represents the national stage entry of International Application PCT/US2018/063225, filed Nov. 30, 2018, which claims priority to U.S. provisional Patent Application 62/597,033 filed Dec. 11, 2017. The contents of this application are hereby incorporated by reference as if set forth in their entirety herein.

STATEMENT REGARDING FEDERALLY SPONSORED RESEARCH/DEVELOPMENT

This invention was made with Government support under Grant Number 1112550, awarded by the National Science Foundation. The Government has certain rights in the invention.

FIELD OF THE INVENTION

Compositions and methods for stabilizing biomolecules such as glucagons are disclosed. Specifically, trehalose-based nanogels comprise trehalose-based copolymers conjugated to biomolecules such as glucagon, wherein the nanogels protect, stabilize, deliver and controlled-release the biomolecules.

BACKGROUND OF THE INVENTION

Glucagon is a peptide hormone that interacts with glucagon receptors in the liver to trigger the conversion of glycogen into glucose, raising blood glucose levels. It is commonly used by hypoglycemic patients and to treat bradycardia resulting from beta-blocker overdose; however, high cost, limited availability, and primarily instability currently thwart its full clinical potential. There are two reasons for these limitations. First, the isoelectric point of glucagon is near seven, making the peptide insoluble at neutral pH. For administration, glucagon is typically dissolved in dilute HCl, which can lead to patient discomfort upon injection. Second, glucagon begins aggregating within hours in solution, mainly through side chain deamidation, forming amyloid fibers that are cytotoxic. This instability severely limits its clinical usefulness and any unused solution must be discarded immediately. Therefore, there is a great need to create stable glucagon formulations.

Several approaches have been developed to stabilize glucagon in solution. One strategy is to chemically modify glucagon to increase its solubility and stability. DiMarchi and coworkers have chemically modified glucagon through iterative amino acid substitutions to change the isoelectric point, resulting in a more soluble analog at physiological pH. Additionally, they developed glucagon prodrugs with increased stability that convert to active glucagon at slightly basic pH.

A second strategy to prevent glucagon aggregation involves the covalent attachment of poly(ethylene glycol) (PEG), known as PEGylation. This strategy has been shown to improve glucagon stability to lyophilization cycles as well as resistance to adsorption onto surfaces. Further, Anderson and coworkers showed that supramolecular PEGylation could stabilize glucagon against aggregation in solution. However, none of these reports mention whether or not the conjugates retain bioactivity after polymer conjugation. Since glucagon interacts with its receptor on the cell surface, irreversibly attached conjugates may not be active because the steric shield of the polymer could prevent interactions between the small peptide ligand and receptor. A final strategy to stabilize glucagon is through the addition of excipients, such as sugars, to the formulation. Common excipients such as lactose, trehalose, cyclodextrins, and hydroxyethyl starch have all been shown to stabilize glucagon; however, use of these excipients still resulted in significant peptide degradation after a two-week incubation in solution.

Trehalose that is used in glucagon formulations is an excipient employed for many pharmaceuticals due to its stabilizing properties. Consisting of two alpha-linked glucose units, it is a non-reducing sugar commonly accumulated in large amounts by organisms with tolerance to desiccation, known as anhydrobiotes. The addition of trehalose to living cells, such a *Saccharomyces cerevisiae* and primary human fibroblasts, has also been shown to confer desiccation tolerance. As an excipient, trehalose acts as a chemical chaperone and can reduce aggregation and adsorption of proteins because of its ability to stabilize biological structures. The protection by trehalose against additional environmental stressors, including freezing, heating, and oxidation has also been reported. To date, three main hypotheses on the mechanism of trehalose stabilization have been proposed: vitrification, water replacement, and water entrapment. These hypotheses suggest that protein movement is restricted by glassy sugars, that the hydrogen bonding capabilities of trehalose could potentially displace water and stabilize protein structure, and that trehalose is able to trap water near the protein surface, stabilizing protein structure, respectively, all protecting proteins from damage. Current research suggests that potentially trehalose stabilization occurs due to a combination of the above hypotheses.

Our group has shown that trehalose is able to more effectively stabilize proteins to environmental stressors in a polymeric form. We have prepared trehalose glycopolymers with various hydrophobic backbones containing trehalose side chains and have shown that when used as either excipients or conjugates, the glycopolymers can stabilize proteins to heat stress, lyophilization, and electron beam irradiation. Moreover, conjugation to insulin has been shown to improve the circulation time in vivo. Trehalose glycopolymers have also been utilized as hydrogels, allowing for protein stabilization as well as controlled release, and by others to form serum stable nanocomplexes for nucleic acids.

Because nanomaterials allow for high cargo loading, intravenous administration, and often exhibit improved targeted delivery over conjugates, we chose to investigate the use of trehalose glycopolymers to form nanogels to encapsulate, stabilize, and release glucagon. To accomplish this, we synthesized copolymers containing trehalose and pyridyl disulfide (PDS) side chains, which formed redox-responsive nanogels via disulfide exchange with thiolated glucagon as a cross-linker. The choice of pyridyl disulfide groups to form nanogels is based on disulfide cross-linked poly(ethylene glycol) methacrylate (PEGMA)-co-pyridyl disulfide ethyl methacrylate (PDSMA) nanogels first reported by the Thayumanavan group. The group has shown the disulfide linked particles to be biocompatible and recently demonstrated that the nanogel formation conditions are mild enough to encapsulate therapeutic proteins, such as caspase 3, with retention of activity. In collaboration with their group, we showed that bovine serum albumin (BSA) could be covalently yet reversibly conjugated to the outside of PEGMA based nanogels. We anticipated that the use of trehalose polymers would stabilize biomolecules and the use of the peptide as the actual cross-linker would enable high loadings. The results are described herein.

There is a need in the art for agents that are more effective at stabilizing and protecting biomolecules (such as glucagons) against degradation or for delivery and controlled releasing.

SUMMARY OF THE INVENTION

The inventors demonstrate herein the effects of trehalose-based nanogels in protecting biomolecules such as proteins and peptides (with glucagon as an example) from degradation and in controlled release of the biomolecules.

Accordingly, in one aspect, the disclosure encompasses a trehalose-based nanogel comprising (a) a copolymer comprising first units and the second units, wherein (i) the first units comprises trehalose side chains; and (ii) the second units comprise disulfide side chains; and (b) dithiol cross-linkers; wherein the dithiol cross-linkers cross link the copolymer through the disulfide side chains of the second units to form the trehalose-based nanogel.

In one embodiment, the copolymer comprises the first and second units of acrylates, acrylamides, methacrylamides, styrenes, or any other flexible backbones.

In one embodiment, the disulfide cross-linker is a) a dithiol such as a PEG with thiols on either end or b) any peptide or protein with two free thiols as the crosslinker.

In one embodiment, the disclosure encompasses a trehalose-based nanogel comprising (a) a copolymer comprising the first methacrylate units and the second methacrylate units, wherein (i) the first methacrylate units comprises trehalose side chains; and (ii) the second methacrylate units comprise disulfide side chains; and (b) dithiol cross-linkers; wherein the disulfide cross-linkers cross link the copolymer through the disulfide side chains of the second methacrylate units to form the trehalose-based nanogel.

As compared with other work such as those reported by the Reineke group, the nanogels here comprise polymers having trehalose in the side chain rather than oligoPEG in order to stabilize peptides and proteins rather than just encapsulate them. The Reineke Group made nanoparticles with trehalose polymers (where one block was had trehalose side chains and the other block contained positive charges, e.g., J. Am. Chem. Soc. 2013, 135, 15417-15424; ACS Biomater. Sci. Eng. 2016, 2, 43-55). The nanoparticles were made by electrostatic interactions with oligonucleotides. This approach would not work for proteins and peptides that are not highly charged. The applicants are preparing trehalose-based nanogels by covalent disulfide bond formation. The applicants make the nanogels by adding other agents such as cross linkers to cross-link polymers. As one example, Applicants added modified PEG as cross linkers to make the nanogels and another example, a peptide was utilized as a crosslinker providing high loadings of the peptide In addition, the Thayumanavan group nanoparticles are prepared by self-condensation to the disulfide side chains, whereas the nanogels described here by the Applicants utilize external cross-linkers such as peptides; the advantage of such a system is high loadings and encapsulation of small biomolecules.

Further, the proteins of Thayumanavan group's research are encapsulated or conjugated to the outside of already-formed gels. Applicants in this disclosure use glucagon as the cross-linker, thereby increasing loading and eliminating the use of the reductant otherwise needed, which can harm/denature proteins, peptides or other biomolecules.

Applicants use trehalose as an exemplary sugar molecule in the nanogels. Applicants envision other sugar molecules or mixture of sugar molecules could be used for the present invention.

These and other features of the present invention will become apparent to the skilled artisan from the following detailed description considered in conjunction with the accompanying drawings.

BRIEF DESCRIPTION OF THE DRAWINGS

FIGS. 1A-C are a series of diagrams, graphs and images showing that (A) PDSMA1-co-TrMA0.8 nanogels were formed using PEG-dithiol as a cross-linker and characterized using (B) DLS and (C) TEM (2 mg/mL trehalose polymer, 25 mol % PEG-dithiol).

FIGS. 5A-F are a set of images showing TEM images of PDSMA1-co-TrMA1.7 glucagon nanogels in HEPES buffer on (A) day 7, (B, C) day 14, and (D) day 21. Scale bars=0.5 µm. (E, F) After imaging the last time point, nanogels were reduced with TCEP to release glucagon from the nanogels and re-imaged three days later, at which point glucagon aggregates were observed that were not seen in the glucagon nanogel samples. Scale bars=0.5 m (E) and 0.2 m (F). Nanogels were formed at 2 mg/mL polymer at a 5:1 ratio of polymer to protein with respect to thiol groups.

FIGS. 19A-B are a set of TEM images of (A) $PDSMA_{1-co}$-$TrMA_{0.8}$ only and of (B) $PDSMA_{1-co}$-$TrMA_{0.8}$ (+) TCEP. Scale bar=50 nanometers.

FIG. 20 is a TEM image of $PDSMA_{-co}$-TrMA nanogels formed at 10 mg/ml $PDSMA_{1-co}$-$TrMA_{0.8}$ using PEG-dithiol as the cross-linker. Scale bar=0.2 micrometers.

FIGS. 26A-D are a set of TEM images of nanogels formed using (A) 5:1 and (B) 10:1 $PDSMA_{1-co}$-$TrMA_{0.8}$ and (C) 5:1 and (D) 10:1 $PDSMA_{1-co}$-$TrMA_{1.7}$ to thiolated glucagon. Scale bars=200 nanometers.

FIGS. 27A-C are a set of images of fresh $PDSMA_{1-co}$-$TrMA_{1.7}$ glucagon nanogels (A) in solution, (B) aged (2 days) nanogels imaged immediately after TCEP reduction, (C) and three days after reduction. Scale bars=200 nm.

FIGS. 28A-F are a set of characteristic fluorescence microscopy images of HDFs incubated with $PDSMA_{1-co}$-$TrMA_{1.7}$ nanogels cross-linked with thiolated glucagon at (A) 0.5 and (B) 1.0 and (C) 2.5 mg/mL polymer and nanogels cross-linked with PEG-dithiol at (D) 0.5 and (E) 1.0 and (F) 2.5 mg/mL polymer using LIVE/DEAD staining. Scale bar—100 μm.

FIG. 29 is a graph of cytotoxicity studies of $PDSMA_{1-co}$-$TrMA_{1.7}$ Note: The 5 mg/mL has 0% visibility.

FIGS. 30A-C are characteristic fluorescence microscopy images of HDFs incubated with (A) 1.0, (B) 2.5, and (C) 5.0 mg/mL $PDSMA_{1-co}$-$TrMA_{1.7}$ using LIVE/DEAD staining. Scale bar=100 μm.

DETAILED DESCRIPTION OF THE INVENTION

I. In General

Figure 1B:
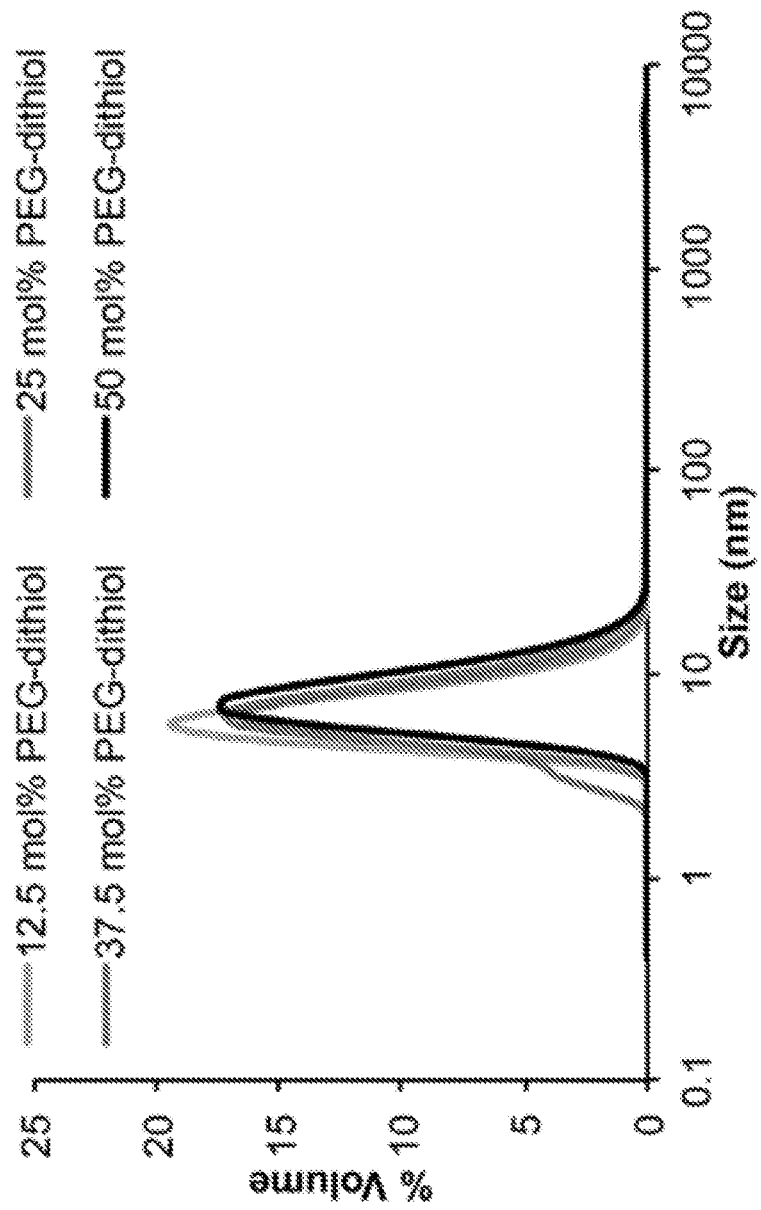

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably.

Unless defined otherwise, all technical and scientific terms used herein have the same meanings as commonly understood by one of ordinary skill in the art. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

A sugar polymer-based nanogel such as a trehalose-based nanogel that remarkably stabilizes and controlled releases biomolecules when biomolecules are covalently conjugated to the nanogel is disclosed herein. The nanogel includes a copolymer comprising at least first units and second units. The first units comprise trehalose side chains and the second units comprise disulfide side chains. The nanogel further includes cross-linkers such as dithiols which link the copolymer through the disulfide side chains of the second units to form the nanogel.

In one embodiment, the copolymer comprises first and second units comprising acrylates, acrylamides, methacrylamides, styrenes, or any other flexible backbones.

In one embodiment, the first and second units are the same type of polymer backbones. In one embodiment, the first and second units are different type of polymer backbones.

In one embodiment, the dithiol cross-linker is a dithiol such as a PEG with thiols on either end or b) any peptide or protein with two free thiols as the crosslinker.

In one embodiment, the disclosure encompasses a trehalose-based nanogel comprising (a) a copolymer comprising the first methacrylate units and the second methacrylate units, wherein (i) the first methacrylate units comprises trehalose side chains; and (ii) the second methacrylate units comprise disulfide side chains; and (b) disulfide cross-linkers; wherein the disulfide cross-linkers cross link the copolymer through the disulfide side chains of the second methacrylate units to form the trehalose-based nanogel.

In one embodiment, the trehalose-based nanogel further comprises a biomolecule. In one embodiment, the biomolecule is glucagon.

In one embodiment, the biomolecule such as glucagon is chemically modified to include functional groups, which covalently link the biomolecule such as glucagon to the nanogel.

In one embodiment, the biomolecule such as glucagon is chemically modified to include more than one thiol as the functional groups.

In one embodiment, the chemically modified biomolecule such as chemically modified glucagon can be used as cross linkers to link the copolymer of the nanogel through the disulfide side chains of the second methacrylate polymer to form the nanogel.

In one embodiment, the trehalose-based nanogel is biocompatible. Boehnke et al. (Adv. Funct. Mater., 2018.) shows the toxicity studies of the trehalose-based nanogel according to one embodiment of the invention.

In another embodiment, the biomolecule such as glucagon which is conjugated within the trehalose-based nanogel is controlled releasable. As shown in Scheme 2C, the thiolated glucagon can be conjugated into the nanogel under pH 2-3 and the glucagon can be released from the nanogel when another reducing agent is added. One of the exemplary reducing agent is GSH.

The reducing agent may also be selected from 2-meracptoethanol, 2-mercaptoethylamine hydrochloride, tris(2-carboxyethyl)phosphine, tris(2-carboxyethyl)phosphine hydrochloride, cysteine, cysteine hyrdochloride, dithiothreitol, glutathione, dithiolbutylamine, and tris-(2-hydroxyethyl) phosphine and any thiol will break a disulfide bond through disulfide exchange.

The reducing agent may also be any agent as described in the art such as https://www.ncbi.nlm.nih.gov/pmc/articles/PMC3766385/.

In another embodiment, the average size of the trehalose-based nanogel is in the range of 0.1 nm to 10 μm, 1 nm-1 μm, 2-500 nm, 5-200 nm, 6-100 nm, 6-50 nm, 6-20 nm, or 7-10 nm.

In one preferred embodiment, the average size of the trehalose-based nanogel is in the range of 1 nm-100 nm, preferable 2 nm-50 nm, or more preferable 5 nm-20 nm.

In another embodiment of the invention, the average size of the trehalose-based nanogel is controllable. For example, the average size of the trehalose-based nanogel can be controlled by varying the concentrations of the copolymer. As shown FIG. 2, 2 mg/mL of a copolymer such as PDSMA-co-TrMA to form nanogels resulted in fairly disperse nanogels ranging from 10-100 nm in diameter (FIG. 2C). When the co-polymer PDSMA-co-TrMA concentration was decreased to 1.0-0.5 mg/mL, a decrease in particle size and dispersity was observed (FIG. 2D). Particles observed via TEM corresponded well to DLS results, which indicated that nanogels were approximately 9 nm in diameter (FIG. 3).

In one embodiment, the trehalose-based copolymer has the structure of:

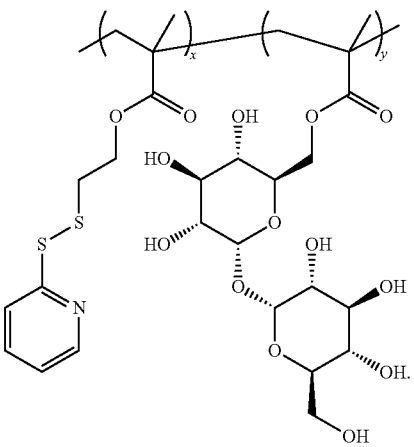

In one aspect, the disclosure reveals a glucagon-containing nanogel. The nanogel comprises a trehalose-based copolymer comprising: a) a methacrylate-based backbone; b) at least one trehalose-based side chain; c) at least one disulfide side chain; and d) glucagon; wherein the glucagon is chemically modified to include more than one thiol and the glucagon cross link the disulfide side chains of the nanogel.

In one embodiment, the glucagon-containing nanogel is biocompatible and controlled releasable regarding to glucagon.

In another embodiment, the average size of the trehalose-based nanogel is in the range of 0.1 nm to 10 μm, 1 nm-1 μm, 2-500 nm, 5-200 nm, 6-100 nm, 6-50 nm, 6-20 nm, or 7-10 nm.

In one preferred embodiment, the average size of the trehalose-based nanogel is in the range of 1 nm-100 nm, preferable 2 nm-50 nm, or more preferable 5 nm-20 nm.

In one embodiment, the trehalose-based copolymer of the Glucagon-containing nanogel has the structure of:

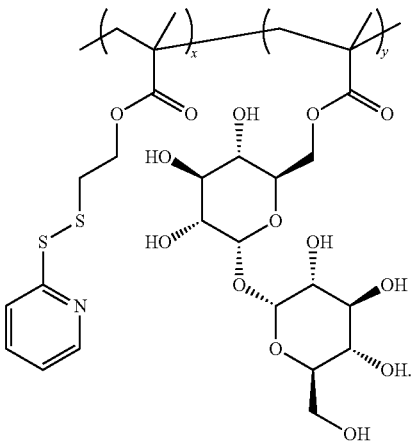

The invention may also include, but is not limited to, stabilization and controlled release of proteins, enzymes, antibodies, DNA, siRNA, and pharmaceutical compositions by using trehalose-based nanogels against the environmental stresses which include but are not limited to heat, desiccation, light, storage, exposure to enzymes, endo- and exo-nucleases and pH variation. Commercial applications of this invention include, but are not limited to, stabilization and controlled release of proteins, enzymes, antibodies, DNA, siRNA, and pharmaceutical compositions thereof utilized as therapeutics, biochemical reagents, and chemical reagents.

In another aspect, the disclosure reveals a method making glucagon-containing nanogels. In one embodiment, the method comprises the steps of: a) producing a copolymer comprising the first units and the second units, wherein the first units comprise trehalose side chains; and the second units comprise disulfide side chains; b) reacting glucagon with a thiolating agent to produce modified glucagon having more than one thiol; c) conjugating the modified glucagons into the copolymer to form glucagon-containing nanogels.

In one embodiment, the copolymer comprises the first and second units of acrylates, acrylamides, methacrylamides, styrenes, or any other flexible backbones.

In one embodiment, the first and second units are the same type of polymer backbones. In one embodiment, the first and second units are different type of polymer backbones.

In one embodiment, the method comprises the steps of: a) producing a copolymer comprising the first methacrylate units and the second methacrylate units, wherein the first methacrylate units comprise trehalose side chains; and the second methacrylate units comprise disulfide side chains; b) reacting glucagon with a thiolating agent to produce modified glucagons having more than one thiol; c) conjugating the modified glucagons into the co-polymer to form glucagon-containing nanogels.

In one embodiment, other biomolecules such as peptides, proteins, RNAs or DNAs may be used to substitute glucagon in the methods. For example, other biomolecules such as peptides, proteins or DNAs may also be modified to include more than one thiol and may be used as cross linkers.

The trehalose-based co-polymer may be added to a solution or powder form of the biomolecule alone or as part of a formulation. The trehalose-based co-polymer may also be covalently attached to a protein or other biomolecule to form the nanogel.

In another embodiment, glucagon-containing nanogels can be used to controlled release glucagon. Boehnke et al. (Adv. Funct. Mater., 2018.) includes the data showing the controlled releasing property of the glucagon-containing nanogels.

Throughout the disclosure, glucagon is used an exemplary biomolecule for the claimed trehalose-based nanogels. Applicants envision that the trehalose-based nanogel may be used to stabilize and controlled release other biomolecule such as proteins, peptides, DNAs, RNAs, enzymes, antibodies, others.

The following examples are offered for illustrative purposes only, and are not intended to limit the scope of the present invention in any way. Indeed, various modifications of the disclosed method in addition to those shown and described herein will become apparent to those skilled in the art from the foregoing description and the following examples and fall within the scope of the appended claims.

III. Definitions

Before the composition and related methods are described, it is to be understood that this invention is not limited to the particular methodology, protocols, materials, and reagents described, as these may vary. The terminology used herein is for the purpose of describing particular embodiments only, and is not intended to limit the scope of the present invention which will be limited only by any later-filed non-provisional applications.

The invention described herein provides a trehalose-based nanogel for stabilizing and controlled-releasing biomolecules.

According to one embodiment of the invention, a trehalose-based nanogel comprises (a) a copolymer comprising the first methacrylate units and the second methacrylate units, wherein (i) the first methacrylate units comprise trehalose side chains; and (ii) the second methacrylate units comprise disulfide side chains; and (b) dithiol cross-linkers; wherein the dithiol cross-linkers cross link the copolymer through the disulfide side chains of the second methacrylate units to form the trehalose-based nanogel.

In one embodiment, the trehalose-based nanogel is used to stabilize and/or controlled release proteins, peptides (such as glucagons) or other biomolecules. In one embodiment, biomolecules, such as glucagons, are encapsulated in the nanogel with covalent bonding to the nanogel. For example, biomolecules, such as glucagons, may be chemically modified to include functional groups such as thiols to covalently bond with copolymers of the nanogel or they may contain more than one thiol.

In one preferred embodiment, the thiolated biomolecules such as thiolated glucagons are covalently conjugated with side chains of the copolymers of the nanogels. For example, in one embodiment, the thiolated biomolecules such as thiolated glucagons are covalently bonded with the disulfide side chains of the copolymers of the nanogel. The encapsulated biomolecules such as encapsulated glucagons may be controlled released from the nanogels.

In one embodiment, the trehalose-based nanogels have many advantages over the existing polymers such as those reported by the Thayumanavan group. For example, those with PEG side chains could self-reduce. Unexpectedly, Applicants demonstrate here that the copolymer could not self-reduce to form the nanogel. To form nanogels, Applicants had to introduce a cross-linker.

In methods of the invention, a trehalose-based nanogel can be used to stabilize and to controlled release a biomolecule such as protein in aqueous solution, or in dry form, e.g., produced by desiccation, dehydration, evaporation or lyophilisation (freeze drying) of an aqueous solution.

In another embodiment, the invention discloses a peptide (such as glucagon) stabilizing formulation comprising a trehalose-based nanogel.

The term "nanogel," as used herein, refers to a nanoparticle composed of a hydrogel—a crosslinked hydrophilic polymer network. Nanogels may be most often composed of synthetic polymers or biopolymers which are chemically or physically crosslinked. Nanogels may be usually in the few to hundreds of nanometers in diameter. Like hydrogels, the pores in nanogels can be filled with small molecules or macromolecules, and their properties, such as swelling, degradation, and chemical functionality, can be controlled.

Nanogels with cross-linked structure may provide a versatile platform for storage and release of proteins and peptides. Nanogels may be used for loading and delivering active forms of proteins toward cells for remaining activity, enhancing stability, and avoiding potential immunogenicity of proteins and peptides.

In one embodiment, nanogels in the present invention are trehalose-based nanogels, which include a copolymer including two methacrylate polymers with trehalose as side-chains of one of the methacrylate polymers.

In one embodiment, the trehalose-based nanogels of the present invention are used to encapsulated, stabilized and controlled-released glucagon.

The term "glucagon," as used herein, refers to a peptide hormone, produced by alpha cells of the pancreas. Glucagon works to raise the concentration of glucose and fat in the bloodstream. Glucagon may be considered to be the main catabolic hormone of the body. Glucagon may also be used as a medication to treat a number of health conditions. Glucagon's effect is opposite to that of insulin, which lowers the extracellular glucose.

In one embodiment, glucagon is a 29-amino acid polypeptide. Glucagon's primary structure in humans is: NH2-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-COOH. The polypeptide of glucagon has a molecular weight of 3482.75 daltons.

The term "glucagon analog" or "glucagon derivative," as used herein, refers to a substance that binds to a glucagon receptor and elicits the same biological activity as that of glucagon. The glucagon derivative may have an amino acid sequence which shares at least 80% homology with native glucagon, and may include a chemical substitution, deletion or modification at some amino acid residues. The glucagon derivative suitable for the present invention may be selected from the group consisting of agonists, derivatives, fragments and variants of native glucagon, and a combination thereof.

The term "biomolecule" as used herein refers to, but is not limited to proteins or peptides, enzymes, antibodies, DNA, siRNA, and pharmaceutical compositions.

In one embodiment, the biomolecules such as glucagon can be chemically synthesized by either solution or solid phase.

The term "protein" used herein refers to any compound of two or more individual amino acids (whether or not naturally occurring) linked via peptide bonds, as occur when the carboxyl carbon atom of the carboxylic acid group bonded to the a-carbon of one amino acid (or amino acid residue) becomes covalently bound to the amino nitrogen atom of the amino group bonded to the a-carbon of an adjacent amino acid. These peptide bond linkages, and the atoms comprising them (i.e., a-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide." Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. As may be appreciated, a "fragment" of a protein may be a form of the protein truncated at the amino terminus, the carboxyl terminus, and/or internally (such as by natural splicing), and may also be variant and/or derivative. A "domain" of a protein is also a fragment, and comprises the amino acid residues of the protein required to confer biochemical activity corresponding to naturally occurring protein. The term "protein" used herein also include "protein conjugate" which refers to a compound complex comprising a "protein" which is interlinked to one another molecule or subject. The term "complex" is used herein to mean those compounds comprising at least two components. The protein may be produced using DNA recombination or mutation techniques. The protein may be produced in vivo in a whole animal, or in a eukaryotic or prokaryotic cell; alternatively, the protein may be generated using an in vitro method such as cell-free in vitro translation e.g. using E. coli lysate, wheat germ extract, or rabbit reticulocyte. Cell free in vitro translation methods can be employed following in vitro transcription, e.g. following phage or ribosome display.

Examples of proteins include, without limitation, Glucagon, Lysozyme, Adenosine deaminase, L-Asparaginase, Mammalian urate oxidase, Interferons, Anti-TNF a Fab, G-CSF, Continuous srythropoietin receptor activator, hGH antagonist B2036, Insulin, Insulin human inhalation, Insulin aspart, insulin glulisine, insulin lispro, Isophane insulin, Insulin detemir, insulin glargine, Insulin zinc extended, Pramlintide acetate, Growth hormone (GH), Somatotropin, Mecasermin, Mecasermin rinfabate, Factor VIII. Factor IX, Antithrombin III (AT-iii), fibroblast growth factor (FGF), basic fibroblast growth factor (bFGF), vascular endothelial growth factor (VEGF), platelet derived growth factor (PDGF), Protein C concentrate, β-Gluco-cerebrosidase, Alglucosidase-α, Laronidase (α-L-iduronidase), Idursulphase (iduronate-2-sulphatase), Galsulphase, Agalsidase-β (human α-galactosidase A), α-1-Proteinase inhibitor, Lactase, Pancreatic enzymes, lipase, amylase, protease, Adenosine deaminase, Pooled immunoglobulins, Human albumin, Erythropoietin, Epoetin-α, Darbepoetin-α, Sargramostim (granulocytemacrophage colony stimulating factor; GM-CSF), Oprelvekin (interleukin11; IL11) Human follicle-stimulating hormone (FSH), Human chorionic gonadotropin (HCG), Lutropin-α, Type I alpha-interferon, interferon alfacon 1, consensus interferon, Aldesleukin (interleukin 2 (IL2), epidermal thymocyte activating factor (ETAF), Alteolase (tissue plasminogen activator: tPA), Reteplase (deletion mutein of tPA), Tenecteplase, Urokinase, Factor VIIa, Drotrecogin-α (activated protein C), Salmon calcitonin, Teriparatide (human parathyroid hormone residues 1-34), Exenatide, Octreotide, Dibotermin-α (recombinant human bone morphogenic protein 2; rhBMP2), Recombinant human bone morphogenic protein 7 (rhBMP7), Histrelin acetate (gonadotropin releasing hormone; GnrH), Palifermin (keratinocyte growth factor; KGF), Becaplermin (platelet-derived growth factor; PDGF), Trypsin, Nesiritide, Botulinum toxin type A, Botulinum toxin type B, Collages, Collagenase, Human deoxyribonuclease I, dornase-α, Hyaluronidase (bovine, ovine), Hyaluronidase (recombinant human), Papain, L-Asparaginase, Rasburicase, Lepirudin, Bivalirudin, Streptokinase, Anistreplase (anisoylated plasminogen streptokinase activator complex; APSAC), Bevacizumab, Cetuximab, Panitumumab, Alemtuzumab, Rituximab, Trastuzumab, Abatacept Anakinra, Adalimumab, Etanercept, Infliximab, Alefacept, Efalizumab, Natalizumab, Eculizumab, Antithymocyte globulin (rabbit), Basiliximab, Daclizumab, Muromonab-CD3, Omalizumab, Palivizumab, Enfuvirtide, Abciximab, Crotalidae polyvalent immune Fab (ovine), Digoxin immune serum Fab (ovine), Ranibizumab, Denileukin diftitox, Ibritumomab tiuxetan, Gemtuzumab ozogamicin, Tositumomab, and itositumomab.

A denatured protein can be fully denatured, or partially denatured or renatured such that the protein is in non-native form as unfolded protein and/or partially folded refolding intermediate(s). An aqueous solution or dried sample comprising denatured protein may contain one or more of these forms. A native protein is in a folded, functional conformation. Some protein may also be present in aqueous solution, or in a dried sample, in the form of contaminating aggregates and/or inclusion bodies.

It is envisioned that, for example, when a protein or peptide like glucagon is conjugated (e.g., covalently bonded through a cross-linker) with trehalose-based nanogels as described here, the peptide such as glucagon may retain at least some of its native bioactivity compared to Glucagon by itself, which is insoluble in water at neutral pH and is unstable in solution. Those skilled in the art appreciate that the percent of bioactivity that is retained is protein or peptide dependent. Furthermore, the length of time that a conjugated protein is able to maintain its bioactivity or function compared to a naked/unmodified protein varies depending on the environmental stressors it is subjected to. It is envisioned the conjugated proteins as described here can retain bioactivity for 5, 10, 20, 30, 40, 50, 60, 70, 80, 90, 100 times longer than an unconjugated native protein under identical environmental conditions.

IV. Examples

Glucagon is a peptide hormone used for the treatment of hypoglycemia; however, its clinical potential is limited by its insolubility and instability in solution. Herein, the encapsulation, stabilization, and release of glucagon by trehalose glycopolymer nanogels are reported. Methacrylate-functionalized trehalose is copolymerized with pyridyl disulfide ethyl methacrylate using free radical polymerization conditions to form trehalose glycopolymers with thiolreactive handles. Glucagon is chemically modified to contain two thiol groups and is subsequently utilized as the cross-linker to form redox-responsive trehalose nanogels with greater than 80% conjugation yield. Nanogel formation and subsequent glucagon stabilization are characterized using polyacrylamide gel electrophoresis, dynamic light scattering, and transmission electron microscopy. It is determined that the solution stability of the glucagon increased from less than 24 h to at least three weeks in the nanogel form. Additionally, in vitro activity of the synthesized glucagon analog and released glucagon is investigated, demonstrating that the glucagon remains active after modification. It is anticipated that these glucagon-nanogel conjugates will be useful as a stabilizing glucagon formulation, allowing for cargo release under mild reducing conditions.

Example 1: Synthesis of TrMA Monomer and a Copolymer Containing PDS and Trehalose Side Chains, PDSMA-Co-TrMA The detailed synthesis can be found in Boehnke et al. (Adv. Funct. Mater., 2018.)

Figure 12:
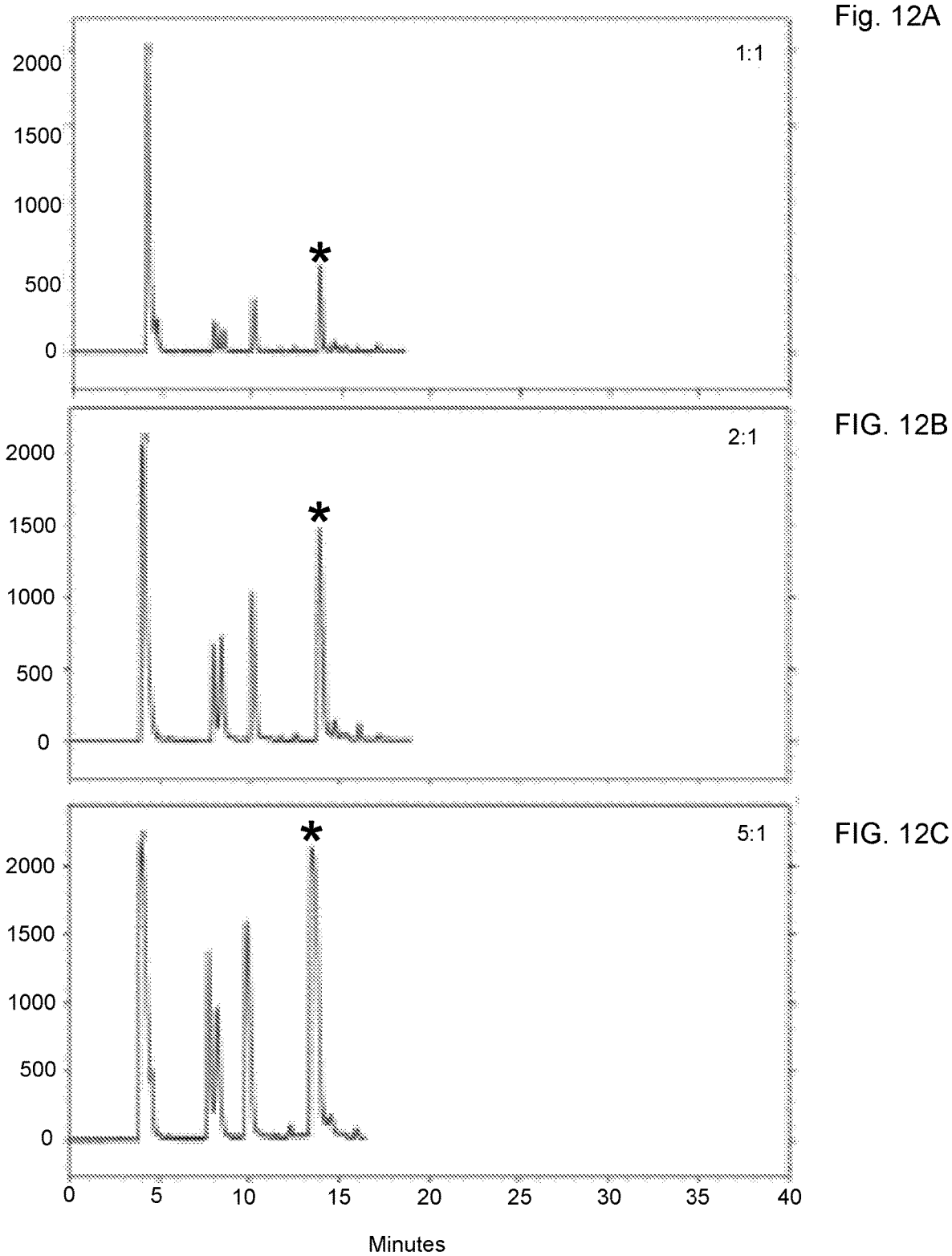
FIGS. 12A-C are a set of graphs showing HPLC traces of TrMA at (A) 1:1, (B) 2:1, and (C) 5:1 trehalose to methacrylic anhydride. Unreacted trehalose elutes first, at 4 minutes, followed by the other TrMA regioisomers between 7 and 10 minutes. C6 TrMA regioisomer elutes at 14 minutes, as indicated by an asterisk.
Figure 13:
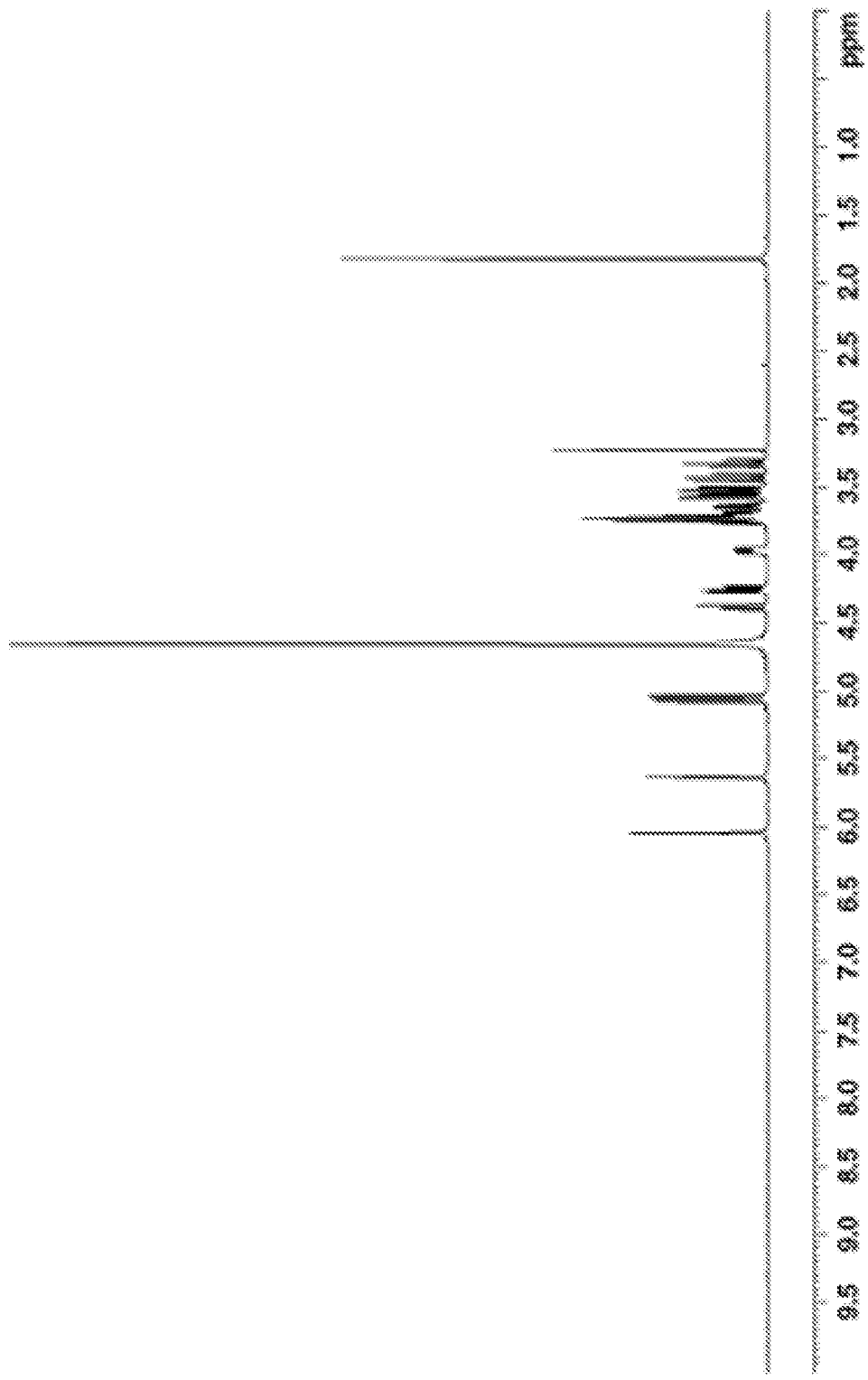
FIG. 13 is a $^1$H NMR spectrum of TrMA (C6) in $D_2O$.
Figure 14:
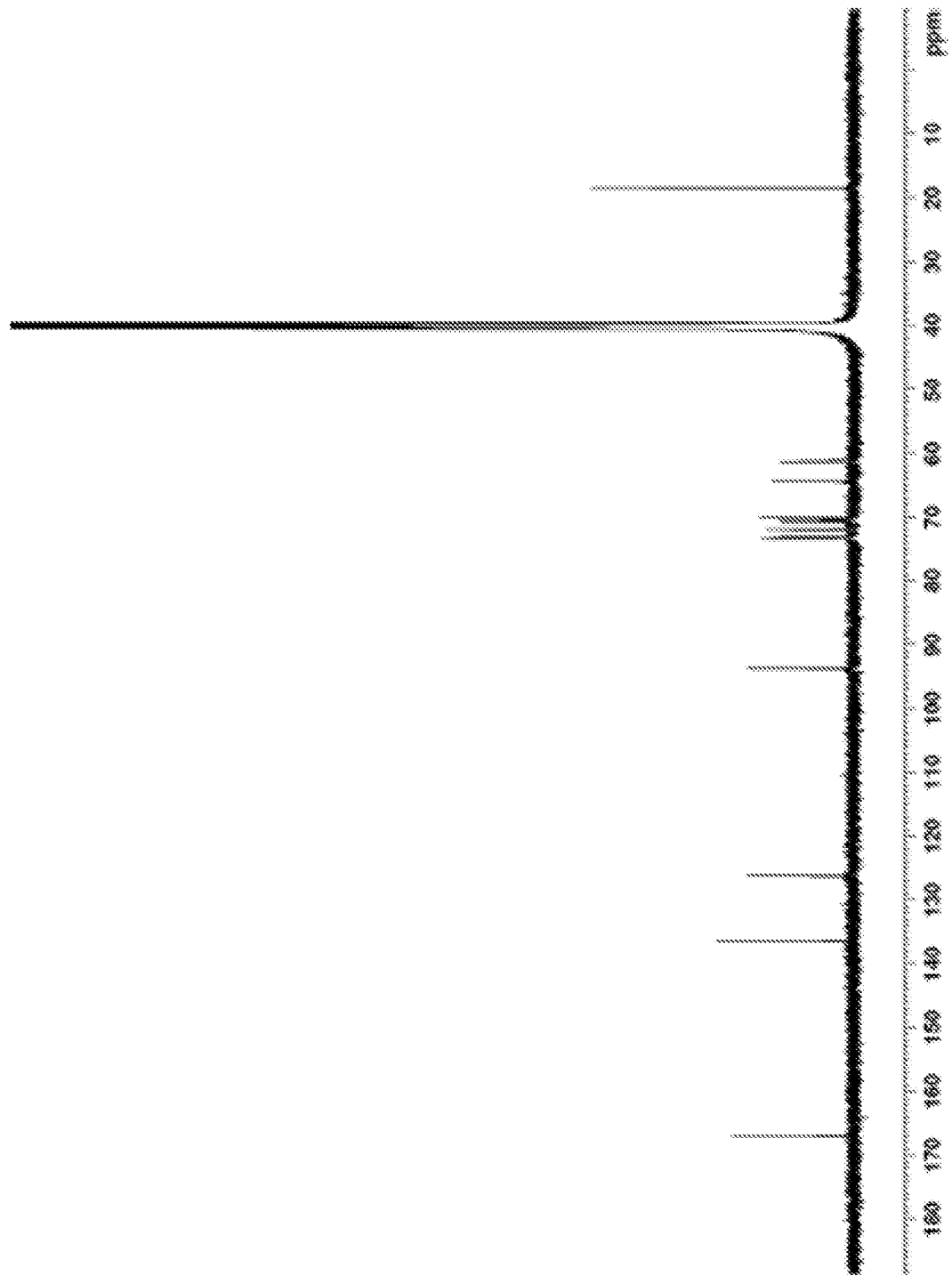
FIG. 14 is a $^{13}$C NMR spectrum of TrMA (C6) in DMSO-$d_6$.
Figure 15:
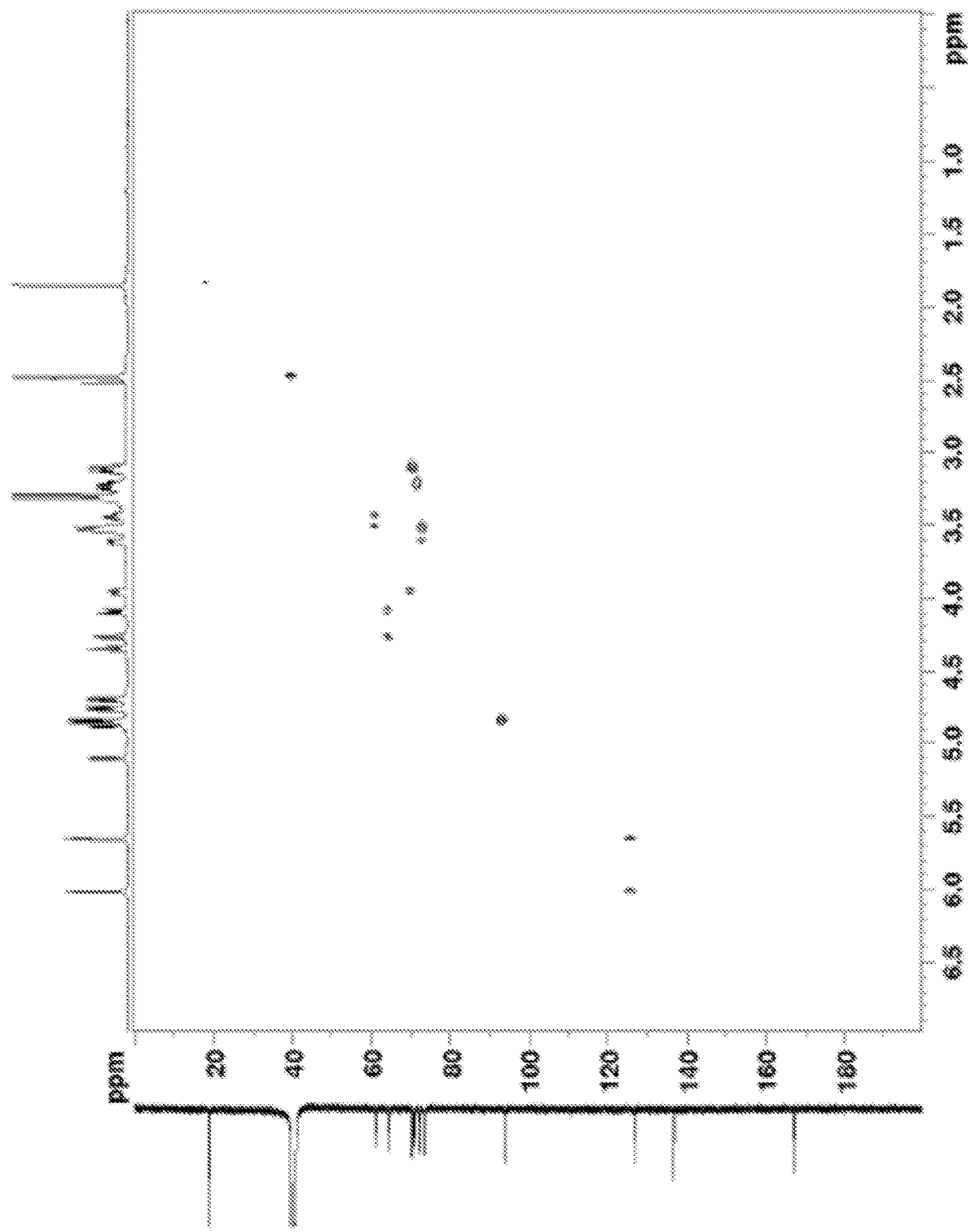
FIG. 15 is a HSQC NMR spectrum of TrMA in DMSO-$d_6$.

To create redox-responsive nanogels, copolymers containing pyridyl disulfide and trehalose side chains were prepared for cross-linking via disulfide exchange. PDSMA was synthesized following a previously reported procedure (FIGS. 8-11). We chose to utilize a methacrylate-functionalized trehalose monomer (TrMA) that we had synthesized previously using a multistep synthesis that employed protecting groups to obtain a single regioisomer (C6). To simplify the synthesis, we reacted unprotected trehalose with methacrylic anhydride in the presence of triethylamine and found that this gave the desired monomer as a mix of regioisomers with the C6 isomer as the predominant product (Scheme 1A). We screened several ratios of trehalose to methacrylic anhydride and found that a five-fold excess of trehalose gave the highest yield of TrMA after HPLC purification (FIGS. 12A-C and Table 2). Monomers were purified by HPLC, and unreacted trehalose could be recovered for resubjection. The TrMA structure and regioisomer assignments were confirmed by 1D and 2D NMR analysis; the overall yield of all regioisomers was 63% and the yield of C6 was 42% (FIGS. 12A-C, 13, 14, and 15).

Scheme 1. (A) Synthesis of TrMA monomer. (B) The copolymer containing PDS and trehalose side chains, PDSMA-co-TrMA, was synthesized using free radical polymerization conditions.

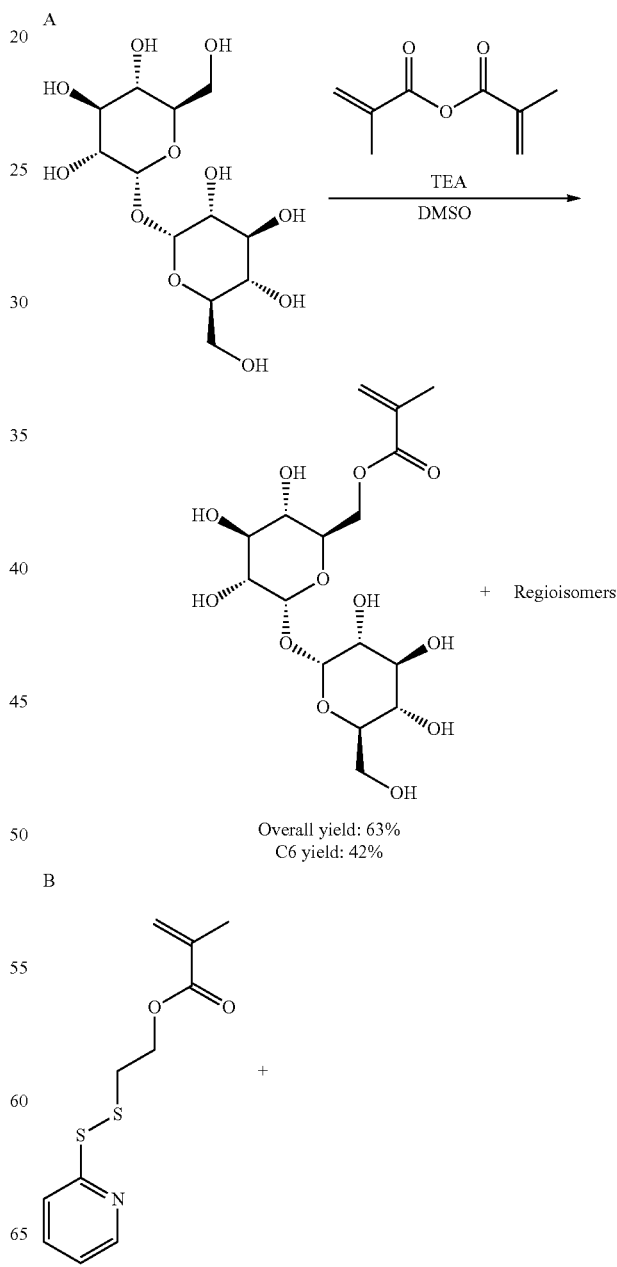

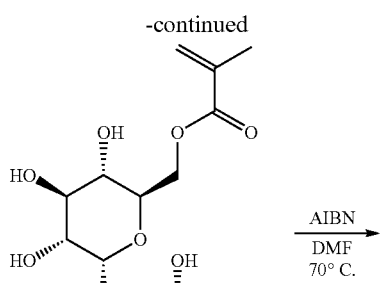

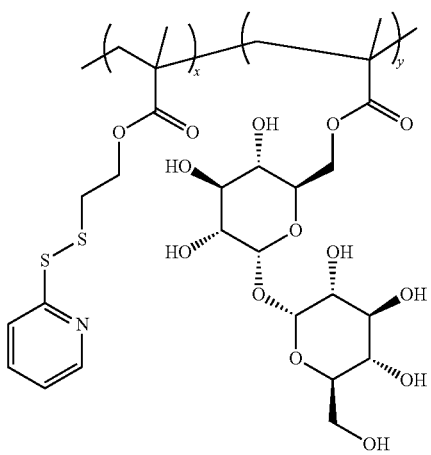

TABLE 1

GPC characterization of PDSMA-co-TrMA polymers.

| Polymer | Feed (PDSMA:TrMA) | Polymer (PDSMA:TrMA) | $M_n$ (Da) | Đ | Yield (%) |
|---|---|---|---|---|---|
| PDSMA$_1$-co-TrMA$_{0.8}$ | 1:1 | 1:0.8 | 4,900 | 2.90 | 60 |
| PDSMA$_1$-co-TrMA$_{1.7}$ | 1:3 | 1:1.7 | 9,700 | 2.38 | 70 |

TABLE 2

Reagent amounts for TrMA syntheses.

| Condition | Eq. Trehalose | Eq. TEA | Eq. Methacrylic Anh. | % Overall yield (% C6) |
|---|---|---|---|---|
| 1:1 | 1 | 15 | 1 | <5 (<1) |
| 2:1 | 2 | 15 | 1 | 25 (16) |
| 5:1 | 5 | 15 | 1 | 63 (42) |

Example 2: Nanogel Synthesis and Characterization

Initially, nanogel formation was attempted using previously described conditions wherein substoichiometric amounts of reducing agent were used to facilitate cross-linking via disulfide formation between the thiol monomers. However, TEM images of polymer plus TCEP indicated no nanogels had formed, and no change in morphology was observed when compared to polymer only samples (FIGS. 19A-B). We hypothesized that the lack of cross-linking was caused by the steric bulk of the trehalose side chains.

Applicants note that this is where the trehalose-based nanogels differs from the PEG side chain gels—where this was very unexpected and for trehalose polymer Applicants could not just reduce but had to add a cross-linker.

To circumvent this issue, we introduced 1,000 Da PEG-dithiol as a cross-linker (FIG. 1A). Resulting PDSMA$_1$-co-TrMA$_{0.8}$ nanogels were characterized using dynamic light scattering (DLS) and transmission electron microscopy (TEM), and fairly uniform particles approximately 9 nm in diameter were observed (FIG. 1B-C). Four different PEG-dithiol cross-linker amounts were investigated: 12.5, 25, 37.5, and 50 mol %, corresponding to 25, 50, 75, and 100% cross-linking if quantitative conversions were achieved. We were surprised to find that changing the amount of PEG-dithiol cross-linker did not appear to change the overall nanogel size. We again hypothesized that this was due to trehalose's large hydrodynamic radius that may prevent nanogels from being contracted smaller than the observed sizes. We did, however, observe that we could change nanogel size by altering the overall polymer concentration. At higher concentrations, the cross-linker could interact with more polymer chains, potentially increasing the size of the particle. At lower concentrations, the cross-linker likely interacts with fewer polymers, potentially even cross-linking the same chain to create single chain nanogels. The above-mentioned nanogels were formed at a PDSMA$_1$-co-TrMA$_{0.8}$ concentration of 2 mg/mL. At a PDSMA$_1$-co-TrMA$_{0.8}$ concentration of 10 mg/mL, nanogels closer to 50 nm in diameter were obtained. These nanogels were more disperse, as evidenced by TEM imaging (FIG. 20).

Figure 16:
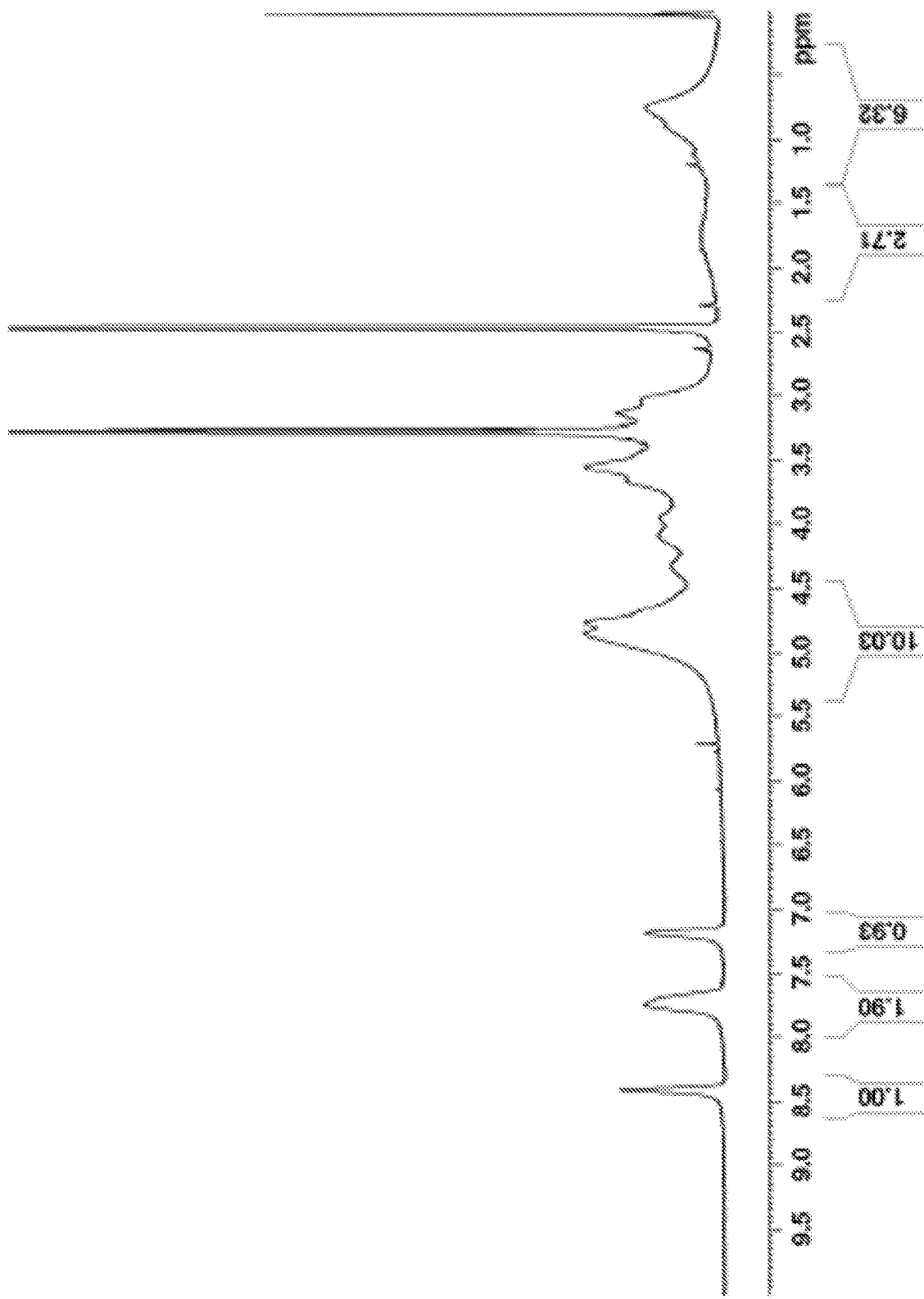
FIG. 16 is a $^1$H NMR spectrum of $PDSMA_{1-co}$-TrMA (1:1 feed ratio) acquired in in DSMO-$d_6$.
Figure 17:
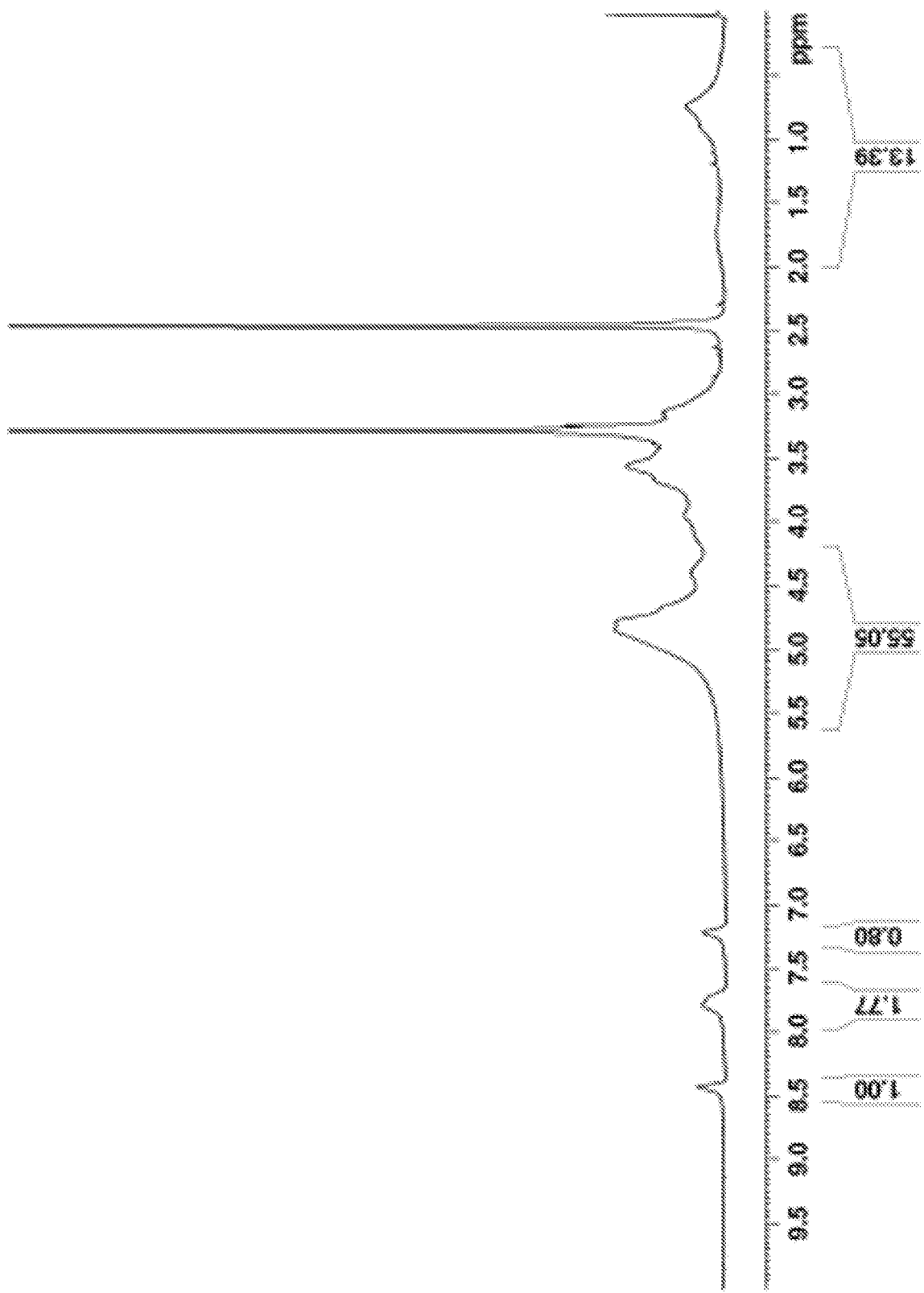
FIG. 17 is a $^1$H NMR spectrum of $PDSMA_{1-co}$-TrMA (1:3 feed ratio) acquired in in DSMO-$d_6$.

Switching from self-cross-linking to the use of a cross-linker could have several advantages. Cross-linkers of different sizes and structures could be added to tune nanogel properties further. Moreover, because we eliminated the Free radical polymerization (FRP) conditions were utilized to synthesize PDSMA-co-TrMA polymers at two different ratios, 1:1 and 1:3 PDSMA to TrMA (Scheme 1B, FIGS. 16 and 17). These monomer feed ratios were chosen to create nanogels with trehalose content for protein stabilization, yet with enough PDSMA content to allow for efficient cross-linking and nanogel formation. Polymers containing 1:0.8 (PDSMA$_1$-co-TrMA$_{0.8}$) and 1:1.7 PDSMA to TrMA (PDSMA$_1$-co-TrMA$_{1.7}$) incorporation as determined by $^1$H NMR were obtained.

The resulting polymers were characterized using size exclusion chromatography (SEC) (Table 1). An increase in number average molecular weight (Mn) from 4,900 (PDSMA$_1$-co-TrMA$_{0.8}$) to 9,700 (PDSMA$_1$-co-TrMA$_{1.7}$) Da was observed, which corresponds to increasing trehalose content as well as increased hydrophilicity of the polymer. The broad dispersities of the resulting polymers are typical of trehalose glycopolymers synthesized by FRP. Reversible addition-fragmentation chain transfer (RAFT) conditions were additionally screened to obtain polymers with narrower dispersities, though these attempts were unsuccessful. Applicants envision that this is likely specific to the monomers used, and RAFT may be a possible way to make these types of materials with other monomers.

need to add reducing agent in order to form nanogels, we anticipated that this strategy would be useful for the encapsulation of sensitive peptides and proteins that might lose activity in a reducing environment.

Figure 18:
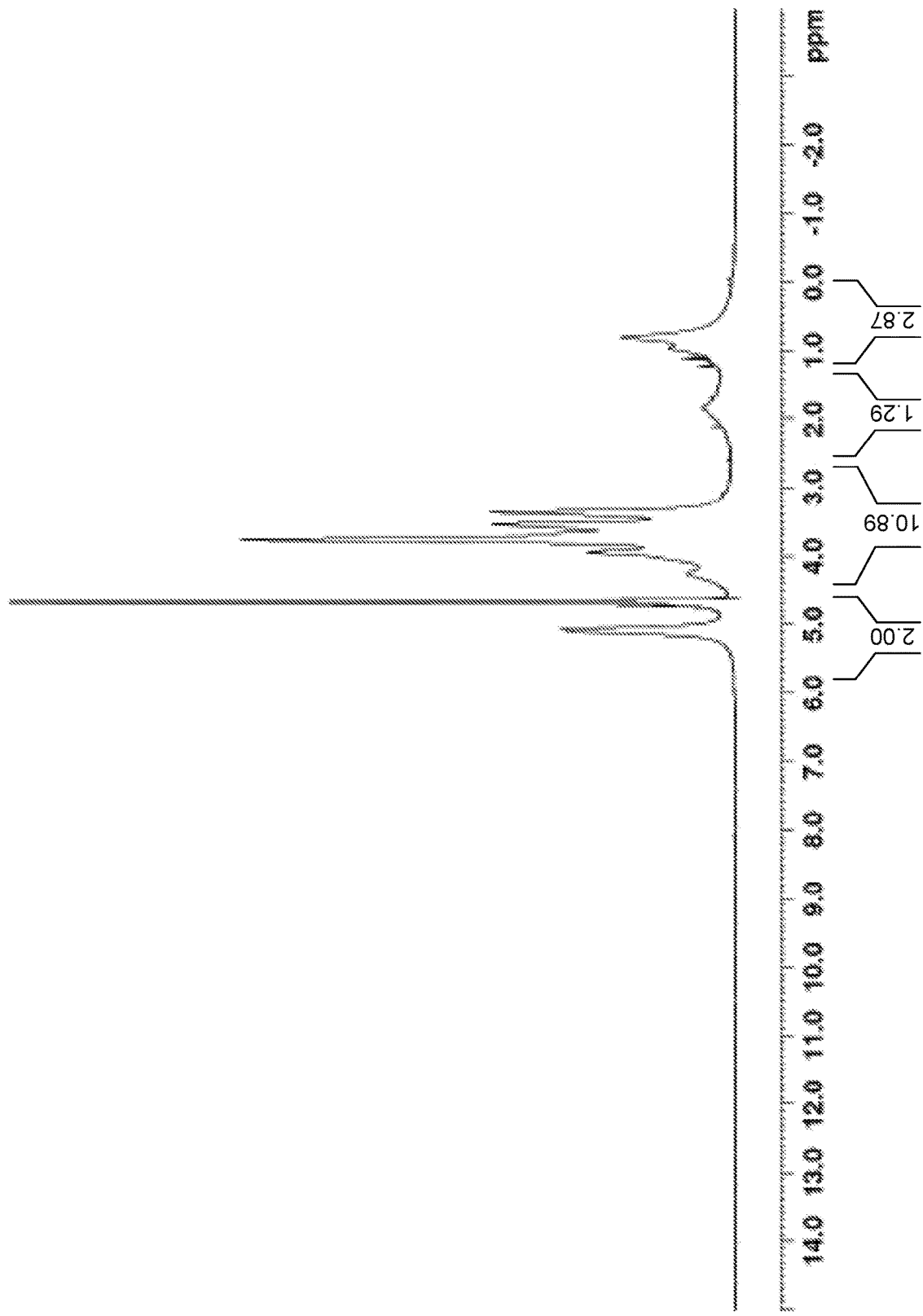
FIG. 18 is a $^1$H NMR spectrum of poly(TrMA) acquired in $D_2O$.
Figure 21:
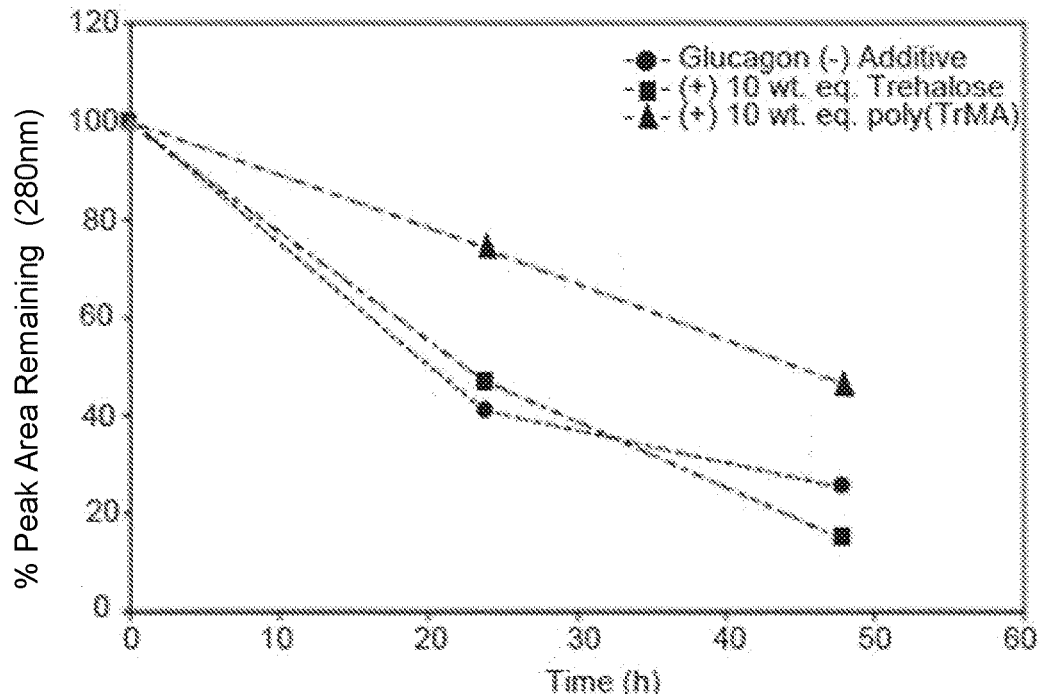
FIG. 21 is a graph of glucagon solutions containing no additive, trehalose, or poly(TrMA) monitored by HPLC over time.
Figure 22:
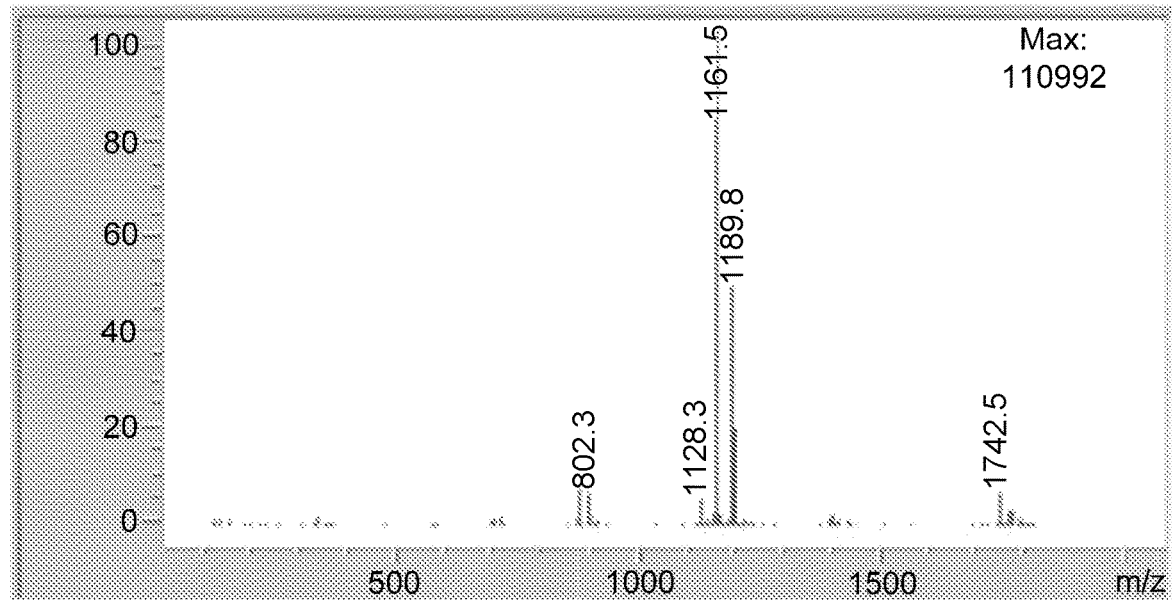
FIG. 22 is a graph of ESI-MS of glucagon thiolated with Traut's reagent. m/z of 1161.5 corresponds to glucagon and m/z of 1189.8 corresponds to the byproduct of singly thiolated glucagon (z=3).
Figure 23:
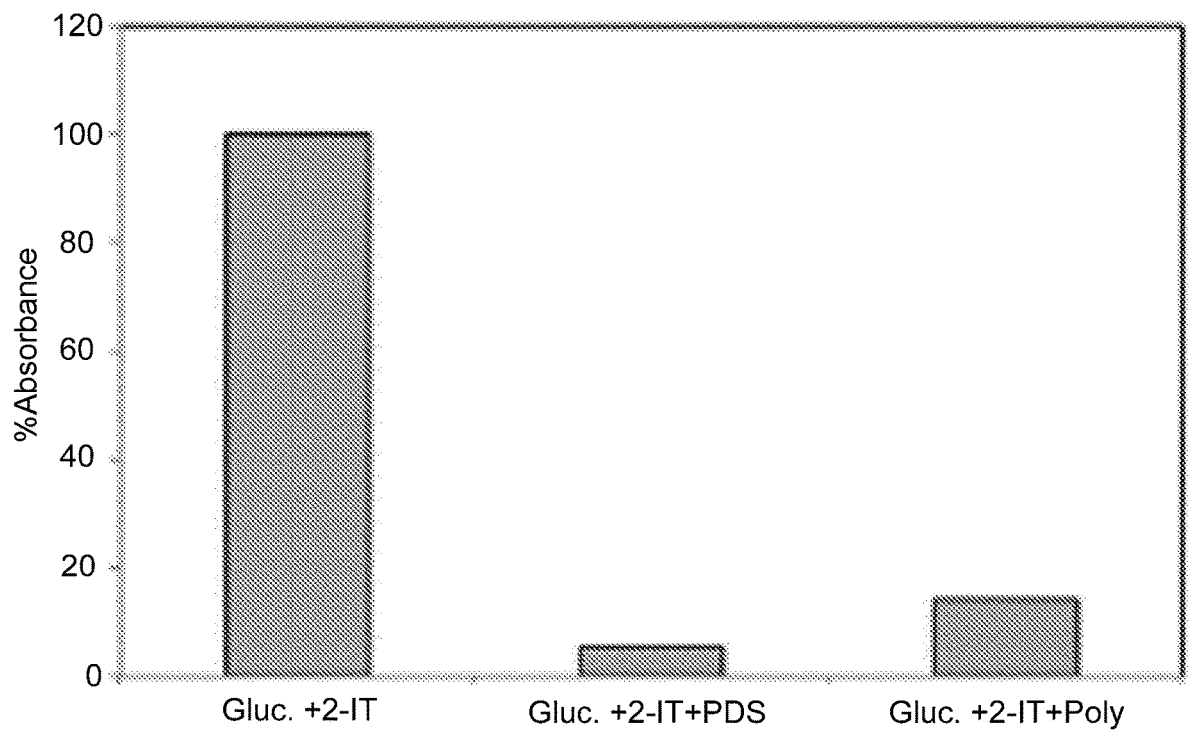
FIG. 23 is a graph of Ellman's assay results of glucagon thiolated with 2-IT tapped with PDS or $PDSMA_{-co}$-TrMA.

Initial studies showed that when TrMA homopolymers were added to glucagon as excipients, glucagon aggregation was slowed, suggesting that trehalose-containing nanogels might stabilize glucagon (FIGS. 18 and 21). At first, we attempted non-covalent incorporation of the glucagon. However, likely due to its small size (3485 Da), the peptide was not retained within the nanogels. Thus, to maximize encapsulation efficiency, strategies for covalent encapsulation of glucagon were explored. For this application, the ideal encapsulation strategy would allow for glucagon to remain attached to the nanogels through covalent yet reversible attachment until release is triggered by an external stimulus, such as a reducing environment. Since native glucagon does not contain any cysteines, thiol groups needed to be installed through modification of amino acid side chains. It has previously been shown that preservation of the positive charge at lysine 12 is essential for binding and glucagon activity, yet there is some tolerance for structural modification, as changing this residue to arginine retained up to 50% activity in vivo. Modification of the N-terminal histidine either by acetylation or methylation has minimal effect on glucagon efficacy.[35] Therefore, we were interested in using a modification strategy that would retain the positive charges of amines while simultaneously installing thiol groups at these sites that might tolerate minor modification. Because glucagon has two amine groups in its structure, at the N-terminus and lysine 12, we aimed to modify both in order to use the peptide as a cross-linker.

Initially, glucagon was modified with 2-iminothiolane (2-IT), resulting in the formation of an amidine group linked to a thiol (Scheme 2A). While thiolation attempts were successful, we observed the formation of a cyclic non-thiol byproduct via LCMS that has also been reported in the literature (FIG. 22). Because this byproduct forms after thiolation, we attempted to trap the thiol prior to cyclization using both PDS and PDSMA-co-TrMA, which was monitored using Ellman's assay (FIG. 23). After mixing glucagon and 2-IT, an initial increase in absorbance was observed that suggested thiolation was occurring, while a decrease in signal after addition of PDS or polymer indicated the thiols were being consumed. While this approach was successful, exact reaction conditions, such as concentration and extent of modification, were difficult to control.

Scheme 2. Thiolation with (A) 2-IT and (B) DTBP, where R represents glucagon. (C) General glucagon nanogel formation and release with the representative structure of glucagon cross-linked PDSMA-co-TrMA.

A

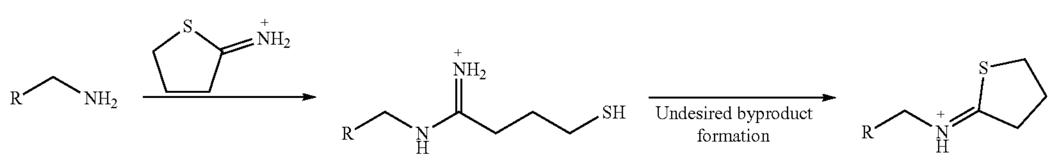

B

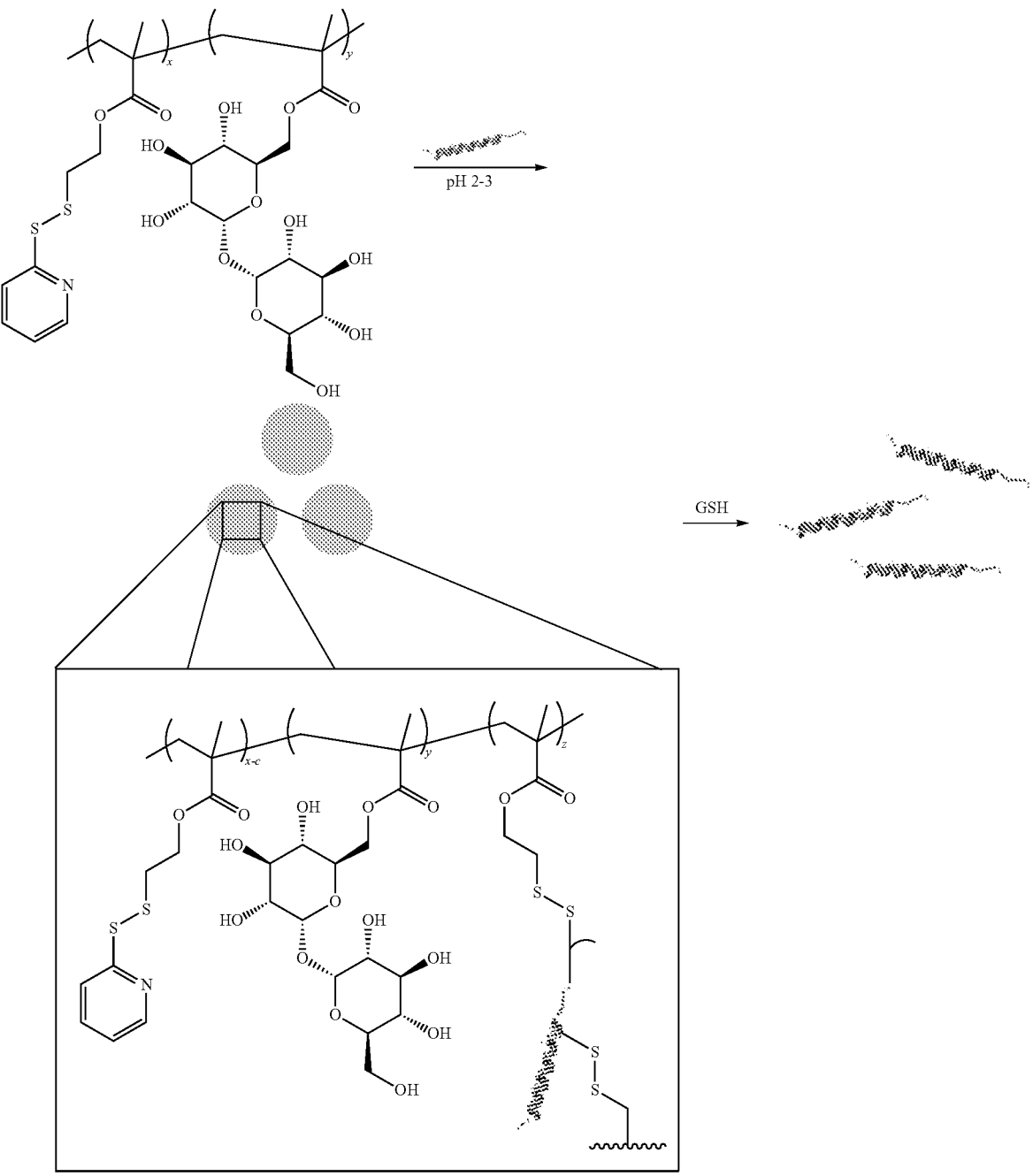

Figure 24:
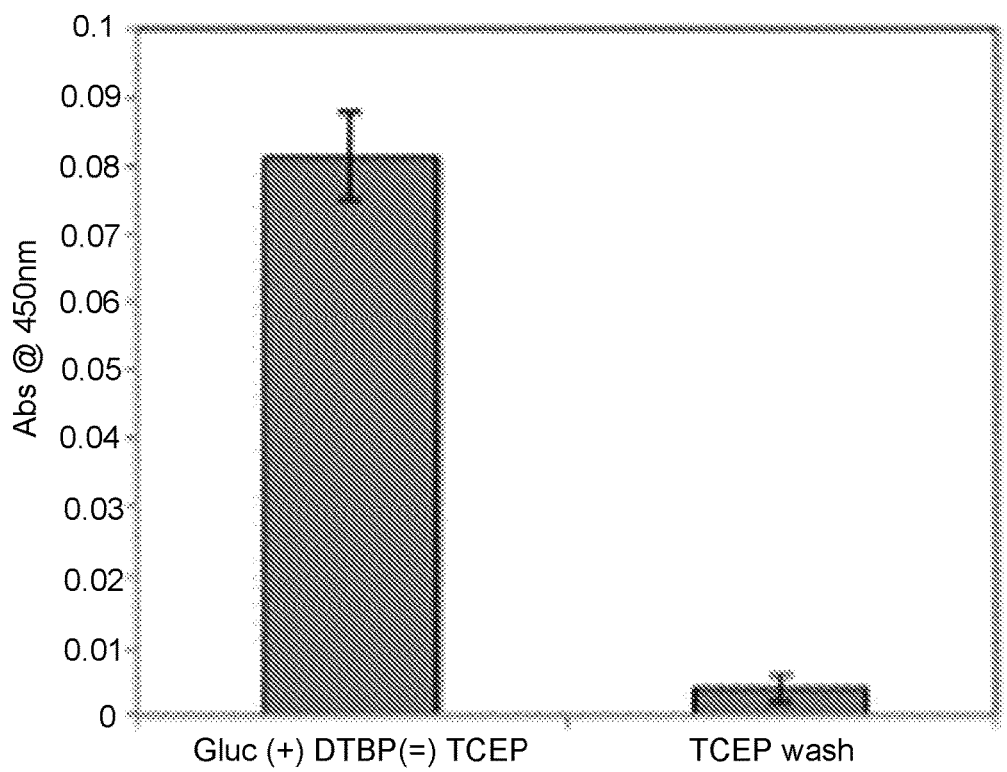
FIG. 24 is a graph of Ellman's assay results of thiolated glucagon and wash solution.
Figure 25A:
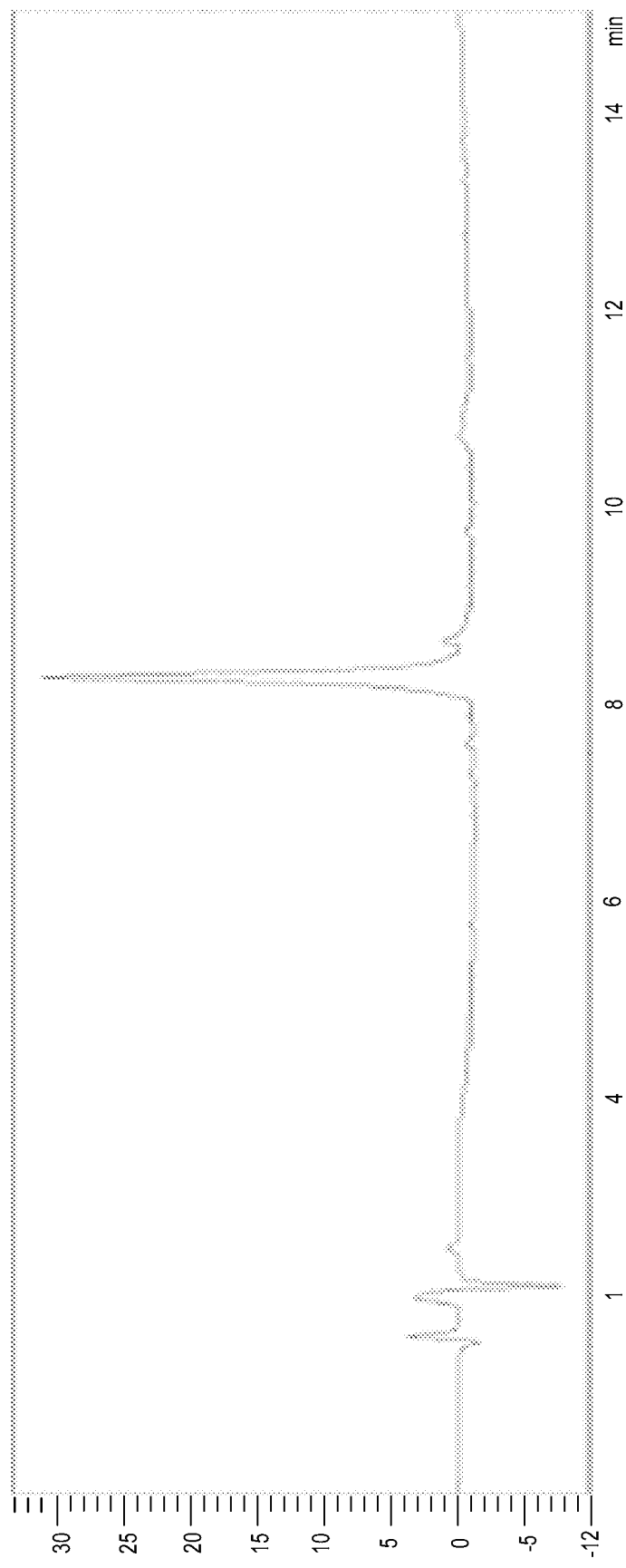
FIGS. 25A-B are a set of graphs showing (A) LC trace after TCEP reduction of glucagon thiolated with DTBP with a peak at 8.3 minutes, and (B) ESI-MS data of thiolated glucagon after TCEP reduction. m/z of 1191.2 corresponds to singly thiolated glucagon and m/z of 1219.6 corresponds to doubly thiolated glucagon (z=3).
Figure 25B:
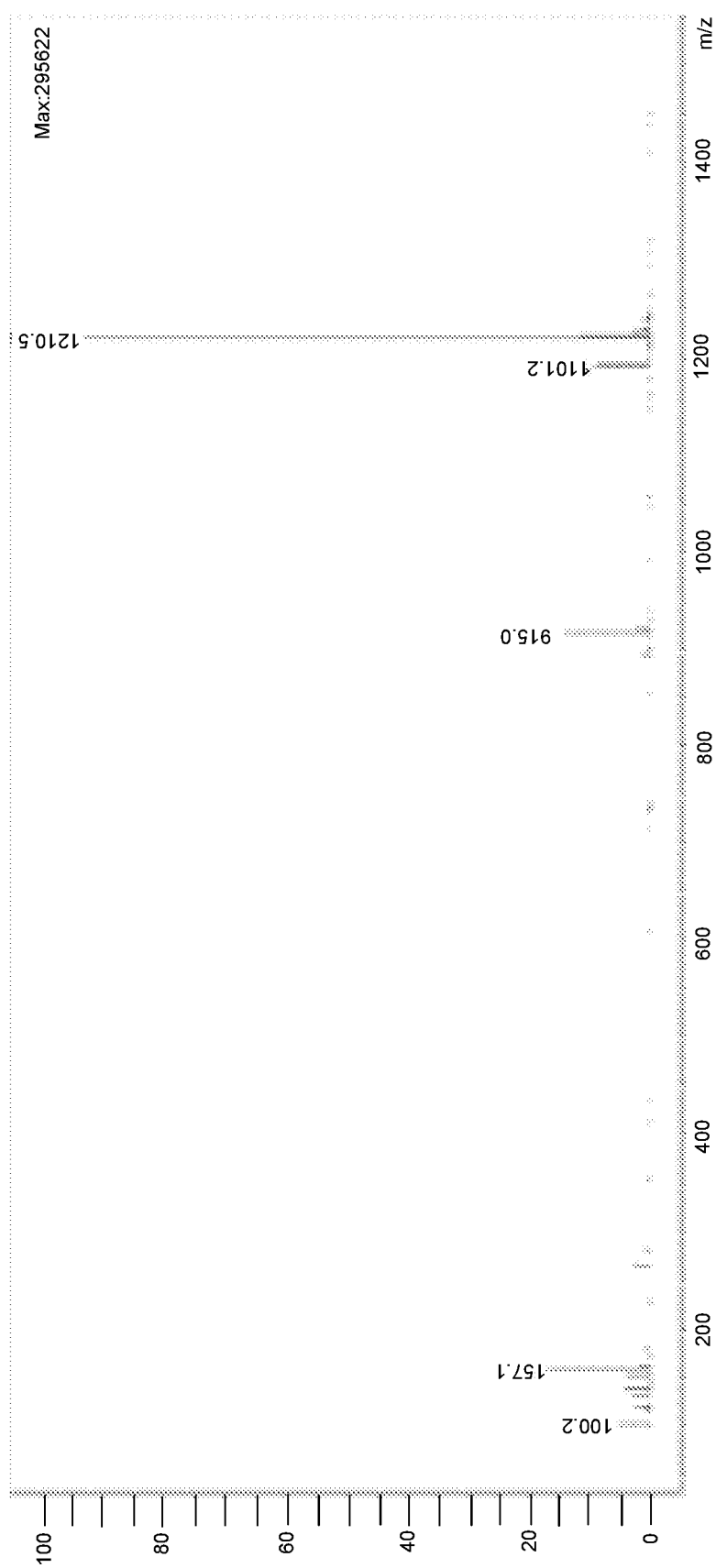

Switching to dimethyl-3,3'-dithio-bis(propionimidate) (DTBP) as the thiolating reagent allowed for efficient and reproducible modification of glucagon under mild conditions without noticeable side reactions (Scheme 2B). While DTBP is less commonly used than 2-IT, it has been found to be biocompatible and has previously been used to create pluronic-horse radish peroxidase conjugates for enhanced cellular delivery. Furthermore, DTBP is a dimeric disulfide that can be used as a built-in protecting group when the reagent is used in excess. Glucagon thiolation with DTBP was monitored using Ellman's assay and LCMS. Because TCEP is added after modification to reduce disulfides, the wash solutions after reduction were also analyzed by Ellman's assay (FIG. 24). The lack of an absorbance increase for the wash solution indicated the modification of glucagon with DTBP and subsequent reduction were successful. Via LCMS, we were able to monitor the disappearance of glucagon (m/z=1161, z=3) and the appearance of two new peaks, m/z=1191 and 1219 (z=3), corresponding to singly and doubly modified glucagon, respectively (FIG. 25A-B). We anticipated that the mixture of products would allow us to attach glucagon to the polymers both as a cross-linker and conjugate by mixing PDSMA-co-TrMA with thiolated glucagon at acidic pH (Scheme 2C).

Figure 2A:
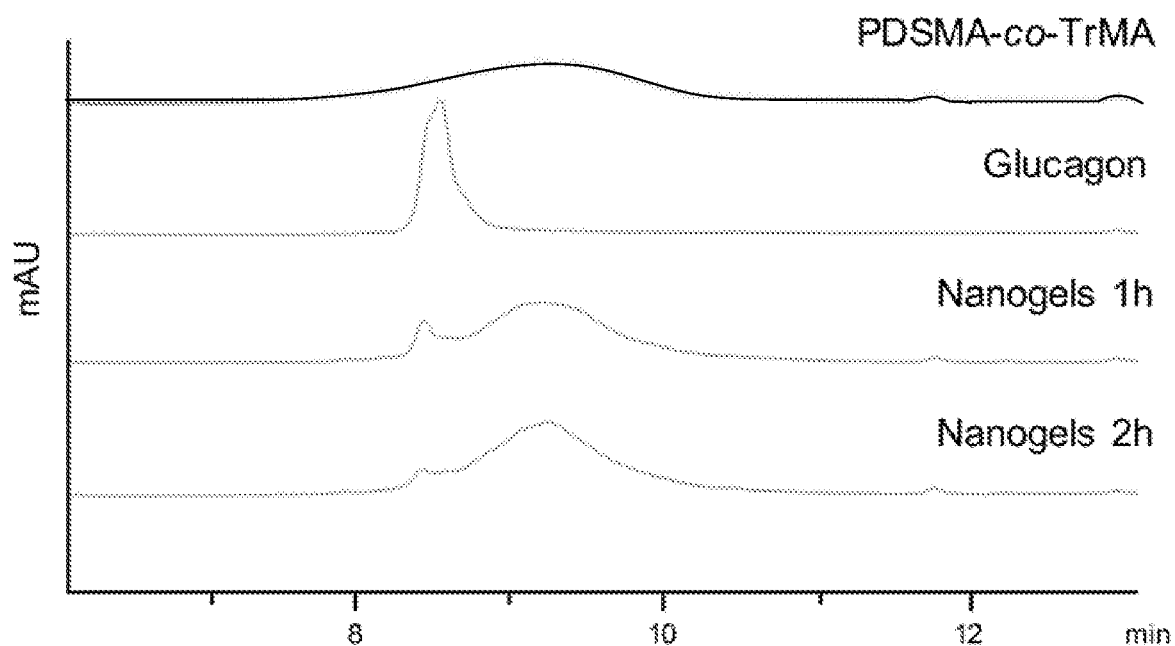
FIGS. 2A-D are a set of graphs showing (A) Glucagon conjugation to PDSMA1-co-TrMA0.8 was monitored via HPLC at 280 nm and (B) SDS-PAGE. Lane 1: protein ladder; lane 2: thiolated glucagon; lane 3: PDSMA1-co-TrMA0.8; lane 4: crude nanogel; lane 5: purified nanogel; lane 6: nanogel from lane 5 reduced with TCEP (10 mg/mL). TEM images of glucagon nanogels formed at (C) 2 mg/mL PDSMA1-co-TrMA0.8 and (D) 0.65 mg/mL PDSMA1-co-TrMA0.8.
Figure 2B:
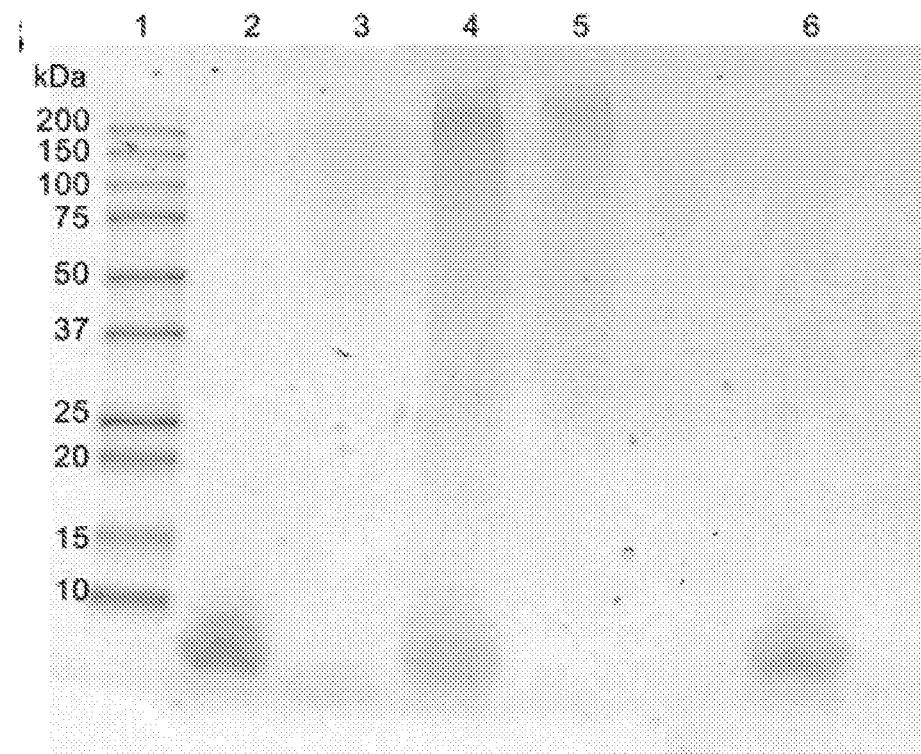
Figure 2C:
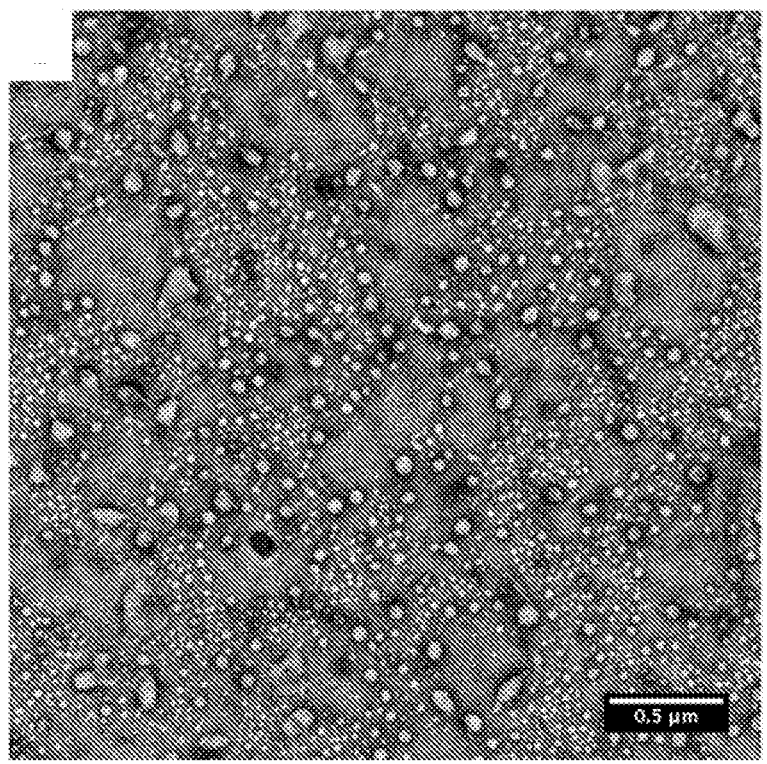
Figure 2D:
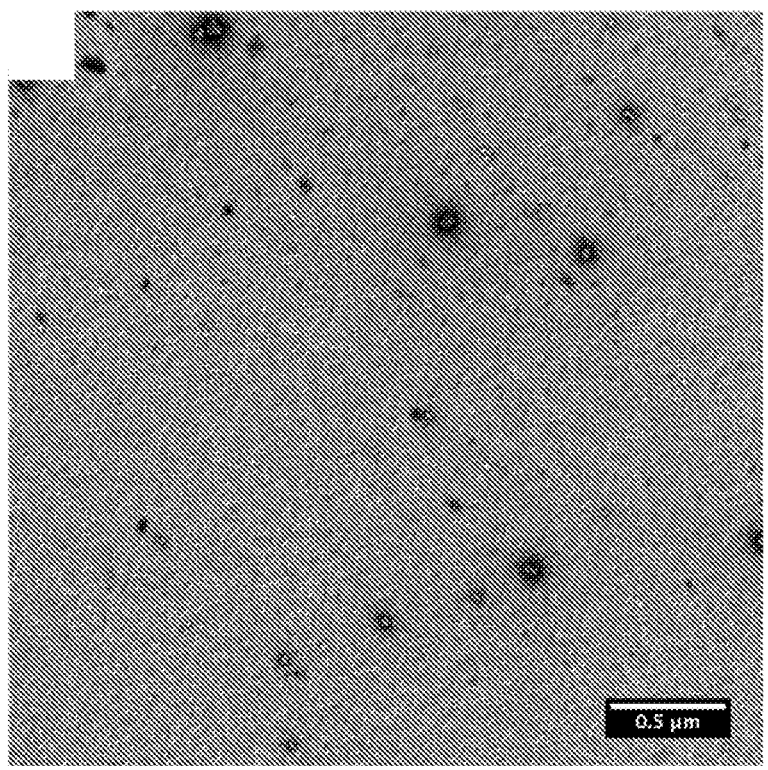

Conjugation of glucagon to $PDSMA_1$-co-$TrMA_{0.8}$ was initially monitored using HPLC (FIG. 2A). Polymer and thiolated glucagon were analyzed separately before mixing the two components and taking measurements at one and two hour time points. After one hour, a significant decrease in the glucagon peak intensity was observed as well as a narrowing of the polymer peak, suggesting peptide and polymer were reacting. Narrowing of the polymer peak indicated that cross-linking may have occurred, contracting the overall polymer structure. After two hours, glucagon was almost completely consumed as indicated by the disappearance of the peak. Moreover, an increase in polymer peak height was also observed, suggesting the successful conjugation of glucagon to PDSMA-co-TrMA. We further assessed glucagon conjugation through SDS-PAGE to analyze the individual components and resulting glucagon-nanogel conjugate (FIG. 2B). Lane 2 contained only thiolated glucagon (3.7 kDa for doubly thiolated) which appeared below the 10 kDa band after staining with Coomassie. Lane 3 contained PDSMA-co-TrMA and could be seen as a very faint high molecular weight smear. Glucagon and polymer were mixed together for two hours before running SDS-PAGE analysis, as shown in lane 4. The appearance of an intense high molecular weight band was observed as well as a decrease in glucagon band intensity, suggesting the peptide successfully reacted with the polymer. After purification, as shown in lane 5, only the high molecular weight band corresponding to nanogel remained. The purified glucagon-nanogel conjugate was then subjected to reducing conditions (10 mg/mL TCEP), as shown in lane 6. Upon reduction, glucagon was released, as indicated by the reappearance of an approximately 3.7 kDa band and the disappearance of the nanogel band.

After confirming that thiolated glucagon could be used to assemble and cross-link $PDSMA_1$-co-$TrMA_{0.8}$ nanogels, the effect of polymer concentration on nanogel morphology was assessed. We found that using 2 mg/mL PDSMA-co-TrMA to form nanogels resulted in fairly disperse nanogels ranging from 10-100 nm in diameter by TEM (FIG. 2C). When PDSMA-co-TrMA concentration was decreased to 1.0-0.5 mg/mL, a decrease in particle size and dispersity was observed (FIG. 2D). Particles observed via TEM corresponded well to DLS results, which indicated that nanogels were approximately 9 nm in diameter (FIG. 3). We hypothesized that at higher concentrations, thiolated glucagon could be able to interact with multiple polymers, potentially linking several smaller nanogels together, accounting for the observed aggregates and dispersity. Concentrations lower than 0.5 mg/mL were low yielding and therefore not investigated further.

Additionally, the effect of cross-linking density and trehalose content on glucagon encapsulation was investigated using the two PDSMA-co-TrMA polymers, $PDSMA_1$-co-$TrMA_{0.8}$ and $PDSMA_1$-co-$TrMA_{1.7}$. Two different ratios of polymer to glucagon were also explored when forming nanogels: 5:1 and 10:1 with respect to thiol groups. A 5:1 thiol ratio of $PDSMA_1$-co-$TrMA_{0.8}$ to glucagon would contain approximately equal amounts by weight of polymer and peptide, indicating high load capacity of the gels. Nanogel conjugation was quantified by comparing the amount of remaining glucagon in the crude nanogel solutions to a thiolated glucagon control (Table 3). On average, nanogels were obtained in 60-70% yield after purification. Interestingly, it was found that using 5:1 thiol ratio of polymer to glucagon resulted in higher yielding conjugations than nanogels prepared at a 10:1 thiol ratio. Moreover, after examining nanogels by TEM, 5:1 nanogels were more uniform and well defined than 10:1 nanogels (FIGS. 26A-D). TEM images of fresh $PDSMA_1$-co-$TrMA_{1.7}$ glucagon nanogels in solution, aged for 2 days, and three days after reduction (FIGS. 27A-C). This could be because a large excess of polymer could effectively cap thiol groups on glucagon with a single chain, resulting in uncross-linked glucagon conjugates instead of nanogels. It was also observed that nanogels formed using $PDSMA_1$-co-$TrMA_{0.8}$ retained more glucagon than $PDSMA_1$-co-$TrMA_{1.7}$, likely due to the higher density of PDS groups capable of conjugating to glucagon. At 10:1 $PDSMA_1$-co-$TrMA_{1.7}$ to glucagon, only a few irregular nanogels were observed by TEM, and the conjugation yield could not be calculated because no defined nanogel band was obtained by SDS PAGE (Table 3). Therefore, we chose to use nanogels prepared at the 5:1 ratio for the majority of subsequent experiments.

TABLE 3

Conjugation yields of nanogels made from $PDSMA_{1-co}$-$TrMA_{0.8}$ and $PDSMA_{1-co}$-$TrMA_{1.7}$ at two different ratios.

| Polymer | Polymer to Glucagon (w.r.t. thiols) | Conjugation Yield (%) |
|---|---|---|
| $PDSMA_{1-co}$-$TrMA_{0.8}$ | 5 | 84 |
| $PDSMA_{1-co}$-$TrMA_{0.8}$ | 10 | 76 |
| $PDSMA_{1-co}$-$TrMA_{1.7}$ | 5 | 77 |
| $PDSMA_{1-co}$-$TrMA_{1.7}$ | 10 | N/A |

Example 3: Glucagon Stabilization and Cytotoxicity and Bioactivity Studies

Glucagon Stabilization and Cytotoxicity and Bioactivity Studies can be found in Boehnke et al., Adv. Funct. Mater., 2018.

The cell compatibility of the polymer and nanogel components to HDFs was evaluated using a LIVE/DEAD viability/cytotoxicity assay (Invitrogen). A control containing no polymer or nanogel was also prepared. Cells were cultured using fibroblast basal medium supplemented with a low serum growth kit (ATCC) at 37° C. with 5% CO2. The cells were seeded in 96-well plates (BD Falcon) at a density of 1000 cells per well. After 24 hours, culture media was replaced with 100 µL media containing PDSMA-co-TrMA or PEG cross-linked nanogels and the cells were incubated for 24 hours. Cells were then washed with pre-warmed Dulbecco's phosphate buffered saline (D-PBS) and stained with LIVE/DEAD reagents (2 µM calcein AM and 4 µM ethidium homodimer-1). Fluorescent images of each well were captured on an Axiovert 200 microscope. The number of live (green) and dead (red) cells were counted, and % cell viability was calculated by dividing the number of live cells by the total number of live and dead cells. All experiments were performed a total of three times. The data is presented by normalizing each set to the control containing no additive.

Characteristic fluorescence microscopy images of the HDFs incubated with $PDSMA_1$-co-$TrMA_{1.7}$ nanogels cross-linked with thiolated glucagon are shown in FIGS. 28A-F. A graph of the cytotoxicity studies is shown in FIG. 29. The characteristic fluorescence microscopy images of HDFs incubated with $PDSMA_1$-co-$TrMA_{1.7}$ using LIVE/DEAD/ staining is in FIGS. 30A-C.

Example 4: Experimental Section

The detail of Experimental section and other related information can be found in Boehnke et al., Adv. Funct. Mater., 2018.

It is envisioned that the disclosed method of stabilizing biomolecules may be combined with other current approaches used for stabilizing biomolecules, such as, for example, chemical modification, protein engineering (e.g. PEGylation, addition of polymeric sucrose and/or dextran, methoxypolyethylene glycol, poly-carboxybetaine, and/or poly-stryrene sulfonate, etc.), protein cross-linkage (e.g. production of cross-linked enzymes crystals or CLEC's, etc.), catalyst immobilization, engineered fusion-proteins and other chemical or biological methodologies. Combining stabilization techniques may enhance pharmacological properties and significantly increase biomolecule's stability to temperature, desiccation, light, storage, exposure to enzymes, endo- and exo-nucleases and pH variation.

Polymerization of TrMA and PDSMA: For 1:1 PDSMA: TrMA(C6 regiosiomer) feed ratio, TrMA (65 mg, 0.16 mmol), PDSMA (40.4 mg, 0.16 mmol), and azobisisobutyronitrile (AIBN) (0.65, 0.004 mmol) were dissolved in DMF (0.60 mL) to give a [TrMA]:[PDSMA]:[initiator] ratio of 40:40:1. For 1 PDSMA:3 TrMA (C6 regioisomer) feed ratio, TrMA (60 mg, 0.15 mmol), PDSMA (12.4 mg, 0.05 mmol), and AIBN (0.4 mg, 0.002 mmol) were dissolved in DMF (0.46 mL) to give a [TrMA]:[PDSMA]:[initiator] ratio of 20:60:1. The solutions were degassed by freeze-pump-thawing five times before initiating polymerization at 70° C. in an oil bath. The polymerizations were stopped after 5 and 6 h, respectively, by exposing the solutions to air. The resulting polymers were purified by precipitating once into ethyl acetate and dialyzing against water using 3.5 kDa molecular weight cutoff (MWCO) tubing for 2 d. The polymers were obtained in 60% and 70% yield after lyophilization, respectively. Monomer incorporation was calculated to be 0.8 to 1 and 1.7 to 1 by comparing the integration of the PDS protons (8.55-8.35 μm, 1H) to the CH3 protons (1.40-0.45 ppm) of the backbone by 1H NMR. Polymer Mn and dispersity (Đ) were determined via SEC to be 4900 Da and 2.90 for PDSMA1-co-TrMA0.8 and 9700 Da and 2.38 for PDSMA1-co-TrMA1.7.

PDSMA$_{co}$TrMA NMR (400 MHz, DMSO-d$_6$) 8.55-8.35 (CHN), 7.90-7.63 (aromatic), 7.28-7.14 (aromatic), 5.30-4.50 (trehalose OHs), 4.50-2.70 (CH2CH2O, CH2CH2O, CH2CHO, CHOH), 2.30-1.40 (CH2 polymer backbone), 1.40-0.45 (CH3, polymer backbone) ppm.

Representative Nanogel Formation with PEG-dithiol: PDSMA1-co-TrMA0.8 (1 mg) was dissolved in 300 μL pH 7.4 PBS. A solution of 1 kDa PEG-dithiol (0.37 mg) was prepared separately in $10 \times 10^{-3}$ m HCl (200 μL). The two solutions were transferred to a glass vial equipped with a stir bar and mixed at 1000 rpm for 3 h. The resulting nanogel solution was purified using 10 kDa MWCO centriprep filters.

Those skilled in the art will recognize, or be able to ascertain using no more than routine experimentation, numerous equivalents to the specific materials and methods described herein and in Boehnke et al., Adv. Funct. Mater., 2018, incorporated herein by reference. Such equivalents are considered to be within the scope of this invention and encompassed by the following claims.

Example 5: Glucagon Stabilization

Figure 3A:
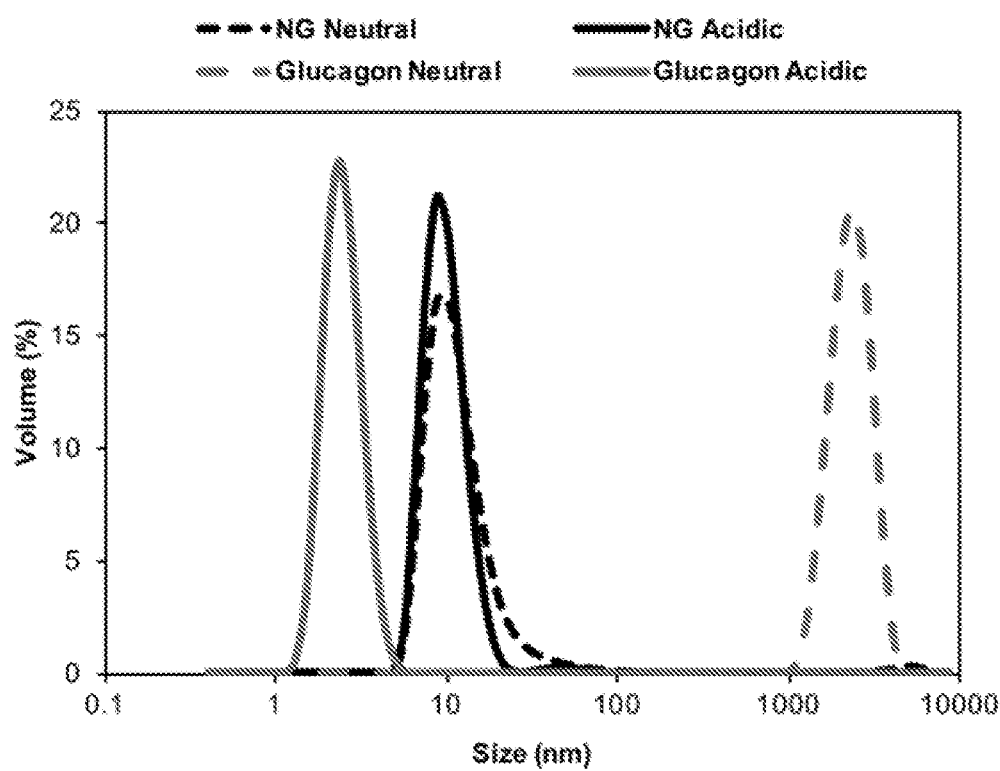
FIGS. 3A-B are a set of graphs showing (A) DLS data of glucagon and PDSMA1-co-TrMA0.8 nanogels at acidic and neutral pH indicate that nanogels remain soluble at both neutral and acidic pH in contrast to unencapsulated glucagon. (B) DLS measurements of glucagon nanogels formed with PDSMA1-co-TrMA1.7 at 0 and 5 days in solution (pH 7.4).
Figure 3B:
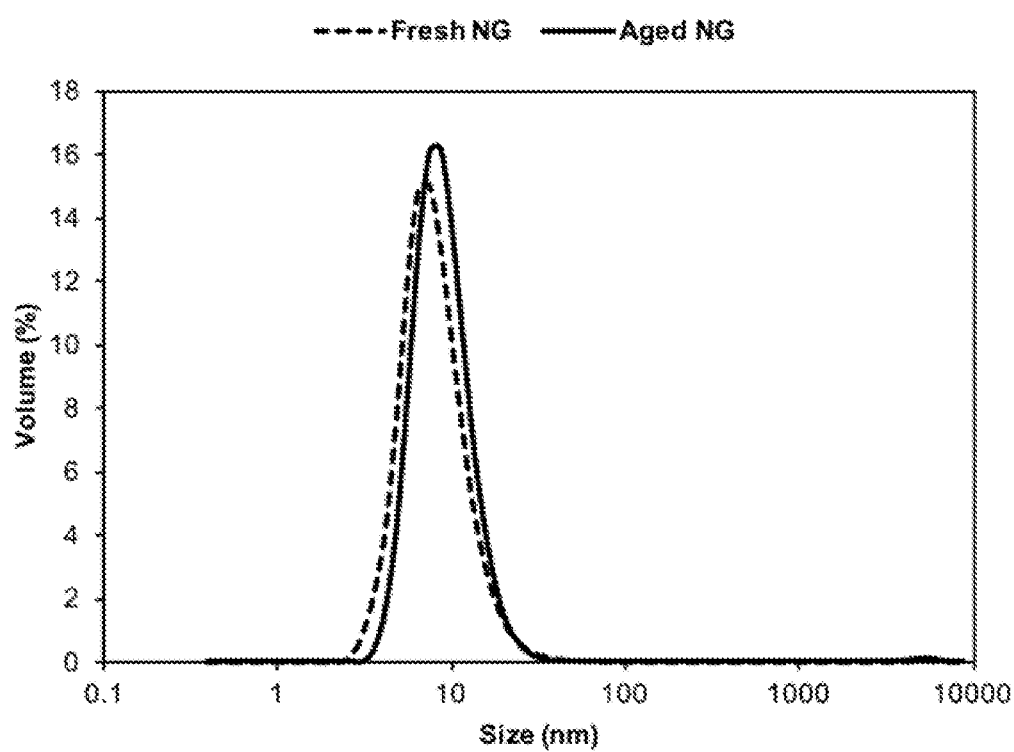

Because glucagon is not soluble at neutral pH, we were interested in studying the solubilizing effect of the glucagon-nanogel conjugates under those conditions. Using DLS, the hydrodynamic diameter of unencapsulated glucagon and glucagon nanogels were measured at neutral and acidic pH (FIG. 3A). Analysis of glucagon solubilized in $10 \times 10^{-3}$ m HCl showed signals corresponding to a diameter of 2-3 nm. When glucagon was neutralized however, a dramatic shift to a diameter of 2000-3000 nm was observed, and the aggregation was additionally confirmed visually as glucagon precipitated out of solution. While a fairly narrow signal was observed, the solution contained many large sized particles that were most likely too large for DLS analysis. Glucagon nanogels, on the other hand, did not change in size in either acidic or neutral pH. Under both conditions, 9 nm diameter signals were observed, indicating that encapsulated glucagon does not aggregate or precipitate out of solution with pH change, which was also confirmed visually as the solution remained homogeneous and clear. It is important to note that this observed change in solubility may be due to covalent attachment of a soluble polymer, and similar stabilization effects could potentially be observed with different types of polymers.

Figures 4A, 4B, 4C:
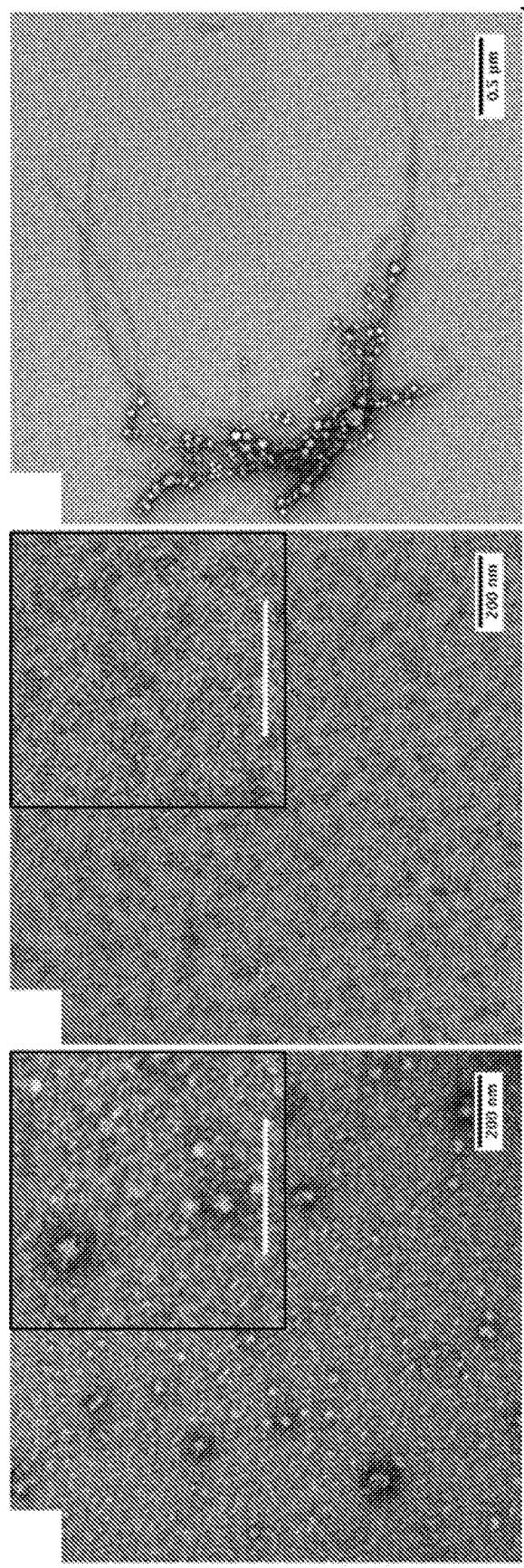
FIGS. 4A-C are a set of images showing (A) TEM images of PDSMA1-co-TrMA0.8 glucagon nanogels in solution and (B) immediately after reduction. (C) 24 h after reduction and release, glucagon fibrils were observed, indicating the nanogels stabilized glucagon until release. Nanogels were formed at 1.3 mg/mL polymer at a 5:1 ratio of polymer to protein with respect to thiol groups. Scale bars=200 nm.

One of the main challenges preventing broader clinical application of glucagon is its instability. Upon dissolution, fibrillation, which is associated with cytotoxicity and loss of activity, is observed within hours, Therefore, when assessing glucagon stability, extent of fibrillation is frequently used as an indirect measure of retention of activity. Due to previous success of stabilizing glucagon to aggregation using PEG, we were interested in investigating the stabilizing effect of the PDSMA-co-TrMA nanogels on glucagon in solution (pH 7.4) using TEM imaging (FIG. 4). Nanogel solutions were pre-pared using PDSMA$_1$-co-TrMA$_{0.8}$ and imaged. Then, TCEP was added to the solution to reduce disulfide cross-links and release glucagon, and the solution was imaged at 0 h (just after reduction) and at 24 h. Immediately after reduction, no nanogels, fibrils, or other aggregates were observed (FIG. 4B). This indicates that while encapsulated, glucagon does not aggregate, suggesting the nanogels are able to stabilize the peptide cargo. After letting the reduced solution sit at 22° C. for 24 h, fibrils and aggregates were clearly observed (FIG. 4C), indicating that glucagon was successfully released under reducing conditions and aggregated when no longer bound inside the nanogels. The experiment was repeated using the higher trehalose content polymer, PDSMA$_1$-co-TrMA$_{1.7}$, and similar results were obtained (FIGS. 27A-C). Additionally, DLS was used to analyze nanogel solutions at days 0 and 5 to ensure no aggregation occurred (FIG. 3B), in agreement with the TEM images we obtained, again indicating that the gels remained stable in solution (pH 7.4) for the duration of the experiment.

A longer stability study was carried out using TEM imaging to determine the extent of glucagon stabilization by the trehalose nanogels in solution (FIG. 5). PDSMA1-co-TrMA1.7 NGs were prepared and imaged at 7, 14, and 21 d. At day 7, round small particles were seen and no glucagon aggregates or fibrils were observed (FIG. 5A). At day 14, a change in nanogel morphology compared to the day 7 images was seen, wherein the particles looked less rounded and slightly smaller (FIGS. 5B and C). This could be due to a change in salt identity or concentration, as the particles were formed in PBS but switched to $200 \times 10^{-3}$ m HEPES for aging and imaging. At day 21, similar particles as observed for day 14 were seen (FIG. 5D). No aggregates were observed in the images. Thus, to verify that glucagon was still retained and stabilized by the polymer, the nanogel solution aged 21 d was reduced with TCEP (5 mg mL-1) and reimaged 3 days later in order to monitor aggregation of glucagon after release from the nanogels (FIGS. 5E and F). The high concentration of TCEP was chosen to ensure that all disulfide bonds would be reduced and unable to reform during this time. Large aggregates were observed after reduction and release from the nanogels; this demonstrates that the glucagon was prevented from fibrillating while encapsulated over the 3 week period. While these aggregates looked different compared to the fibrils imaged in other experiments, it is known that glucagon goes through several different stages of fibrillation, and this type of structure has been reported previously.

Figure 6:
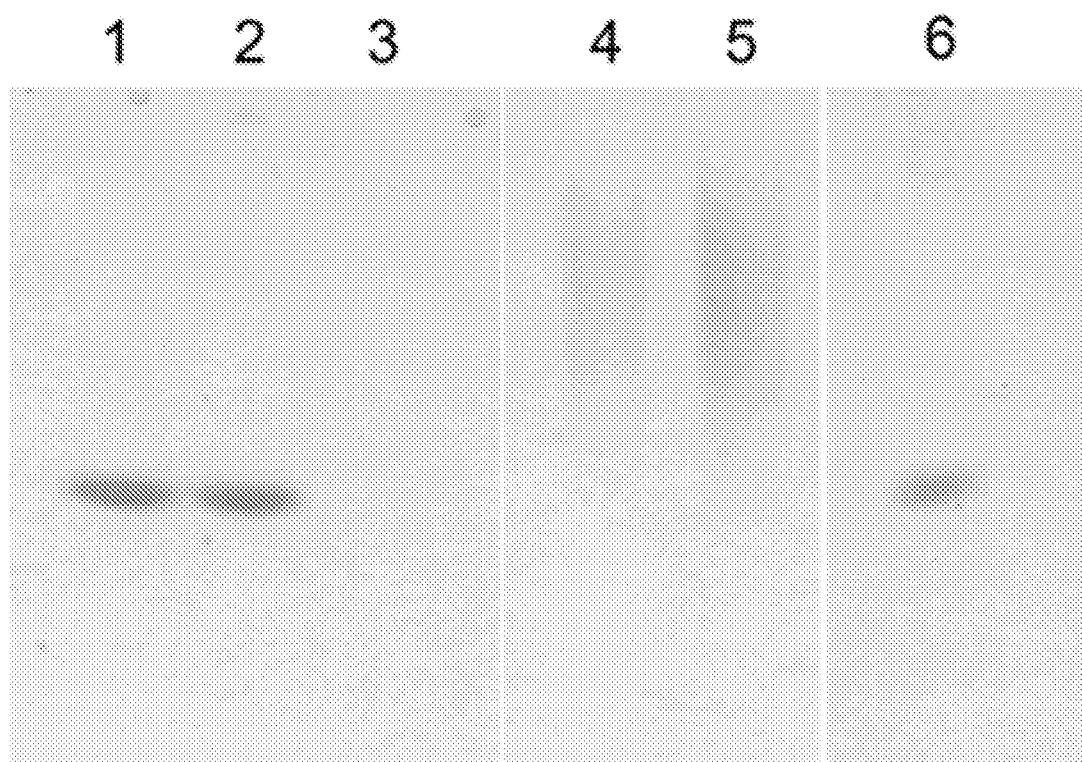
FIG. 6 is a set of graphs showing Native PAGE of glucagon and nanogels. Lane 1: glucagon; lane 2: thiolated glucagon; lane 3: PDSMA1-co-TrMA1.7; lane 4: glucagon-PDSMA1-co-TrMA1.7 nanogel; lane 5: glucagon-PDSMA1-co-TrMA1.7 nanogel aged 5 days in solution (pH 7.4); lane 6: glucagon-PDSMA1-co-TrMA1.7 nanogel from lane 5 reduced with TCEP (10 mg/mL).

Long-term PDSMA$_1$-co-TrMA$_{1.7}$ NG stability was assessed using native PAGE to ensure glucagon was not released over time through hydrolysis (FIG. 6). We also compared native and thiolated glucagon and observed no shift in the bands, indicating the two compounds run comparably on the gel. No differences were observed when comparing fresh nanogels and nanogels aged in pH 7.4 PBS for 5 d, which appeared as a smear on the gel that is typical of protein-polymer conjugates, and the lack of a glucagon band indicated non-specific release was not occurring. After addition of reducing agent, a single band corresponding to glucagon was obtained (lane 6), comparable to the result observed via SDS-PAGE, indicating successful nanogel degradation and glucagon release.

Example 6: Cytotoxicity and Bioactivity Studies

In order to ensure the polymers and nanogels were biocompatible for potential in vitro and in vivo applications, cytotoxicity was assessed using a live/dead assay. Nanogels consisting of PDSMA1-co-TrMA1.7 cross-linked with thiolated glucagon and PEG-dithiol were tested up to 2.5 mg mL$^{-1}$ with human dermal fibroblasts (HDFs) and high cell viability and normal morphology were observed indicating that these particles would be compatible with further biological applications (FIG. 7D and FIG. 28). When tested by itself, PDSMA1-co-TrMA1.7 was also noncytotoxic to HDFs up to 2.5 mg mL$^{-1}$ (FIG. 29). It is important to note that at this concentration the cells exhibited a rounded morphology, indicating they may not be healthy (FIG. 30A-C). However, at 1 mg mL$^{-1}$, normal cell morphology was observed. The increased cytotoxicity of polymer compared to nanogel could be explained by the presence of the PDS side chains that can easily be reduced by cells, as we have previously shown that high concentrations of polymeric thiols elicit cytotoxic effects.

Figures 7A, 7B:
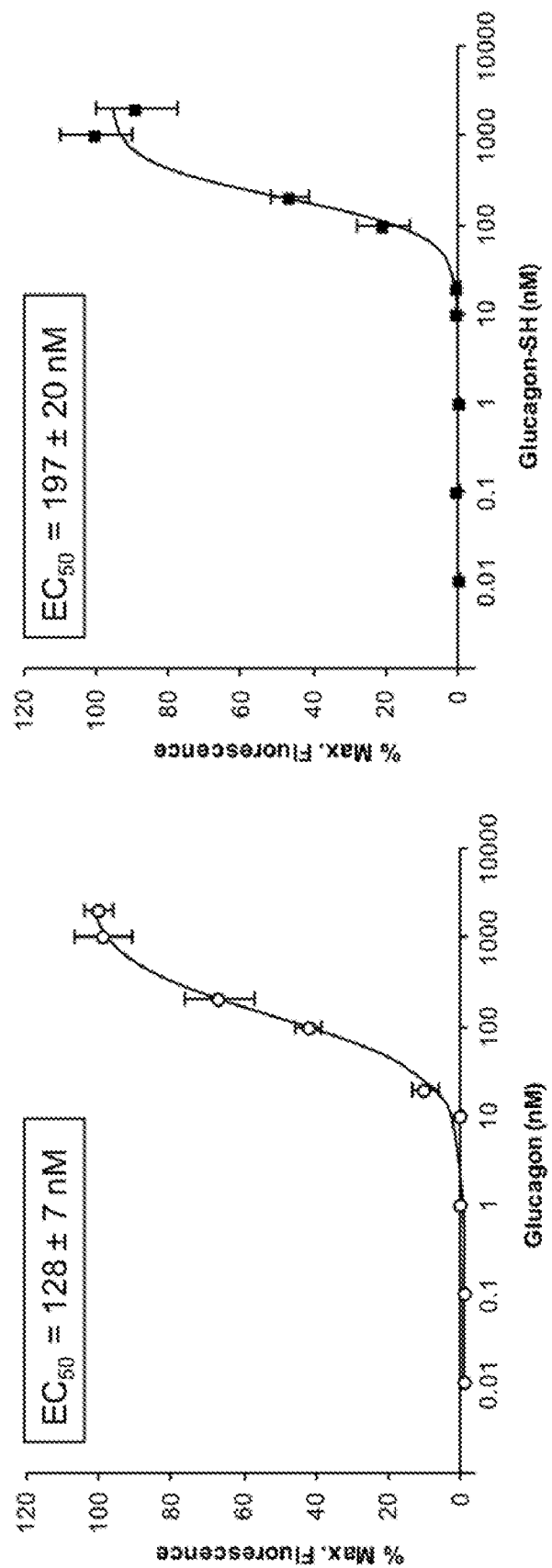
FIGS. 7A-D are a set of graphs showing Dose response curves of (A) glucagon and (B) thiolated glucagon using Chem-1 cells expressing human glucagon receptor. (C) Signal in response to PDSMA1-co-TrMA1.7 glucagon nanogels was also measured before and after reduction and compared to PEG-dithiol cross-linked nanogels. Data are shown as the average and standard error of the mean of two to six independent repeats. (D) Cytotoxicity studies of PDSMA1-co-TrMA1.7 nanogels cross-linked with thiolated glucagon and PEG-dithiol with HDFs via LIVE/DEAD assay indicate that nanogels are non-cytotoxic up to 2.5 mg/mL. Data are shown as the average and standard deviation of three independent repeats.
Figures 7C, 7D:
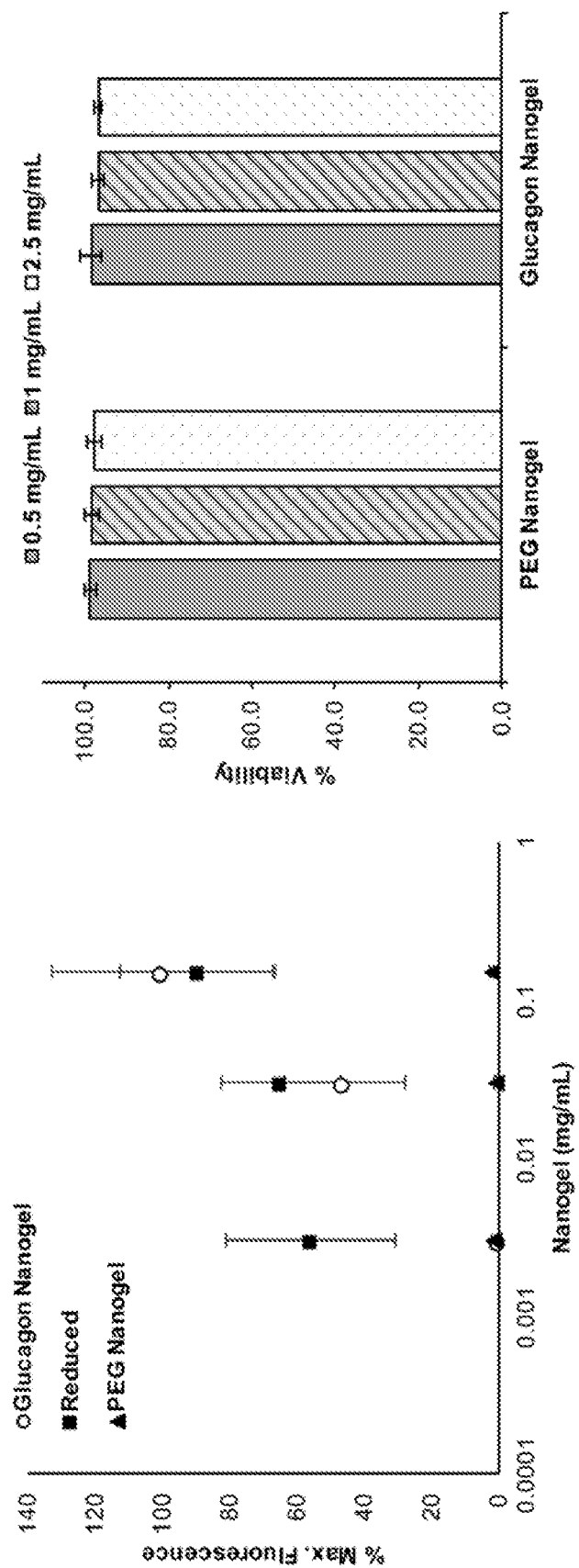
Figure 8:
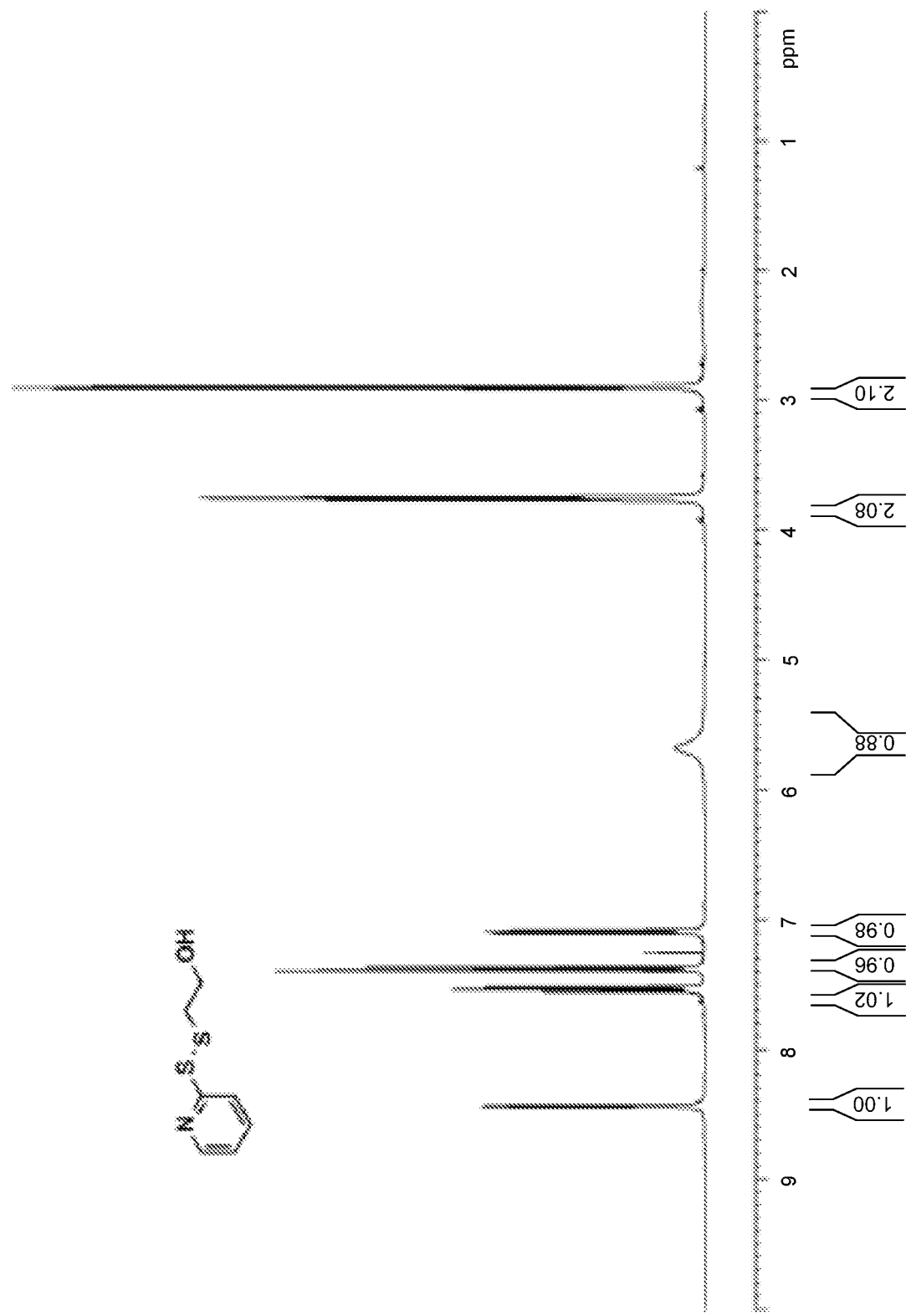
FIG. 8 is a $^1$H NMR spectrum of PDSOH in $CDCl_3$.
Figure 9:
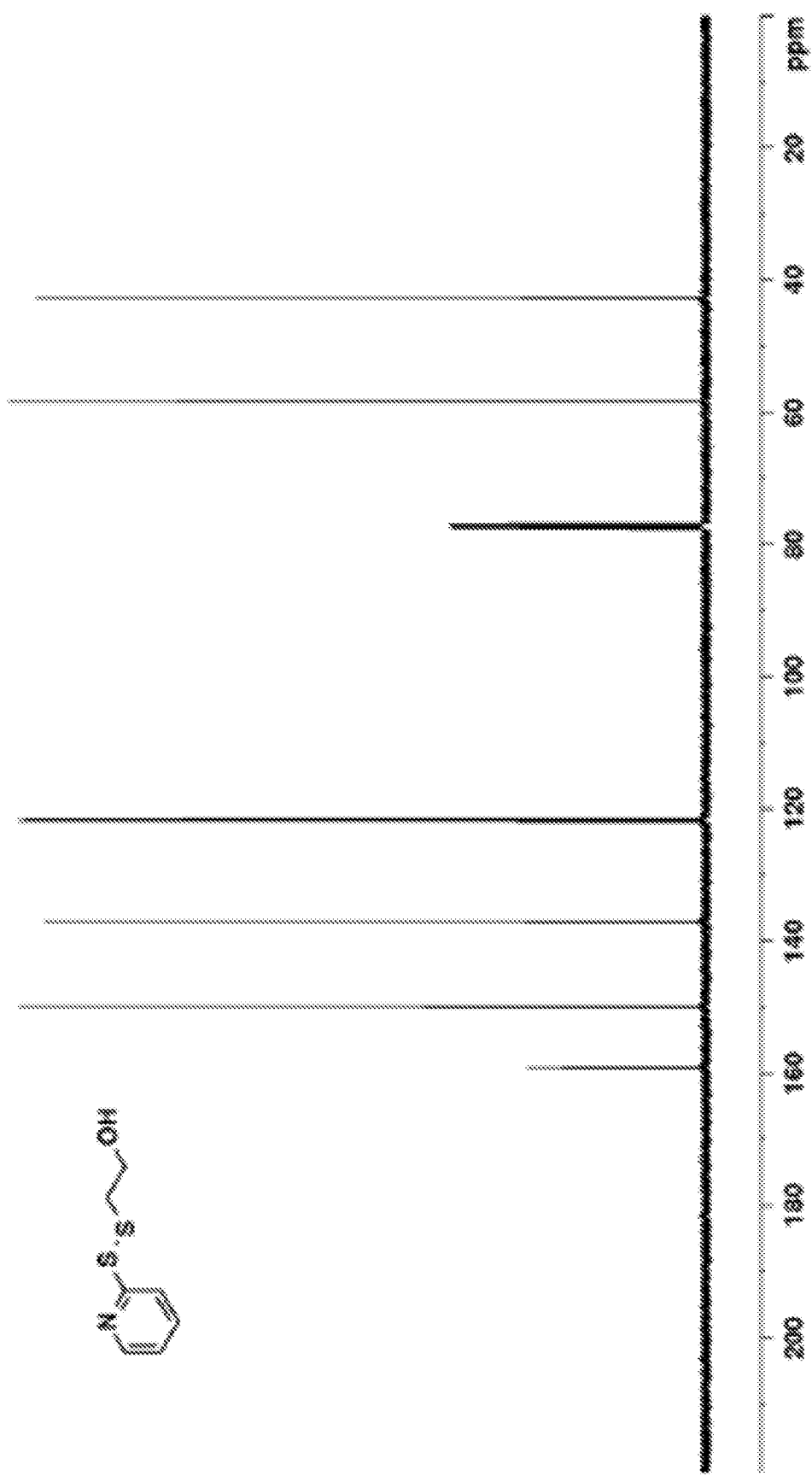
FIG. 9 is a $^{13}$C NMR spectrum of PDSOH in $CDCl_3$.
Figure 10:
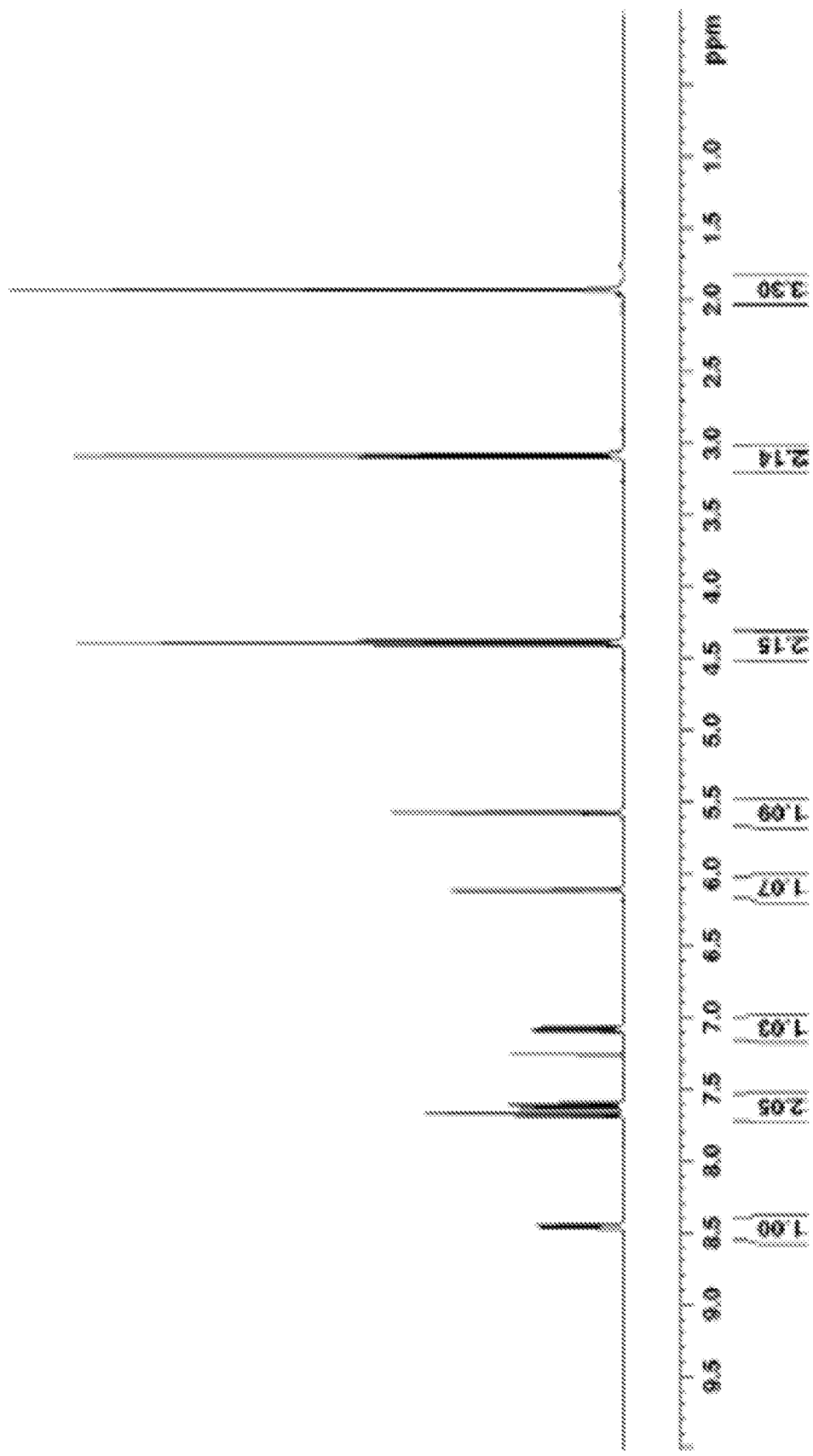
FIG. 10 is a $^1$H NMR spectrum of PDSMA in $CDCl_3$.
Figure 11:
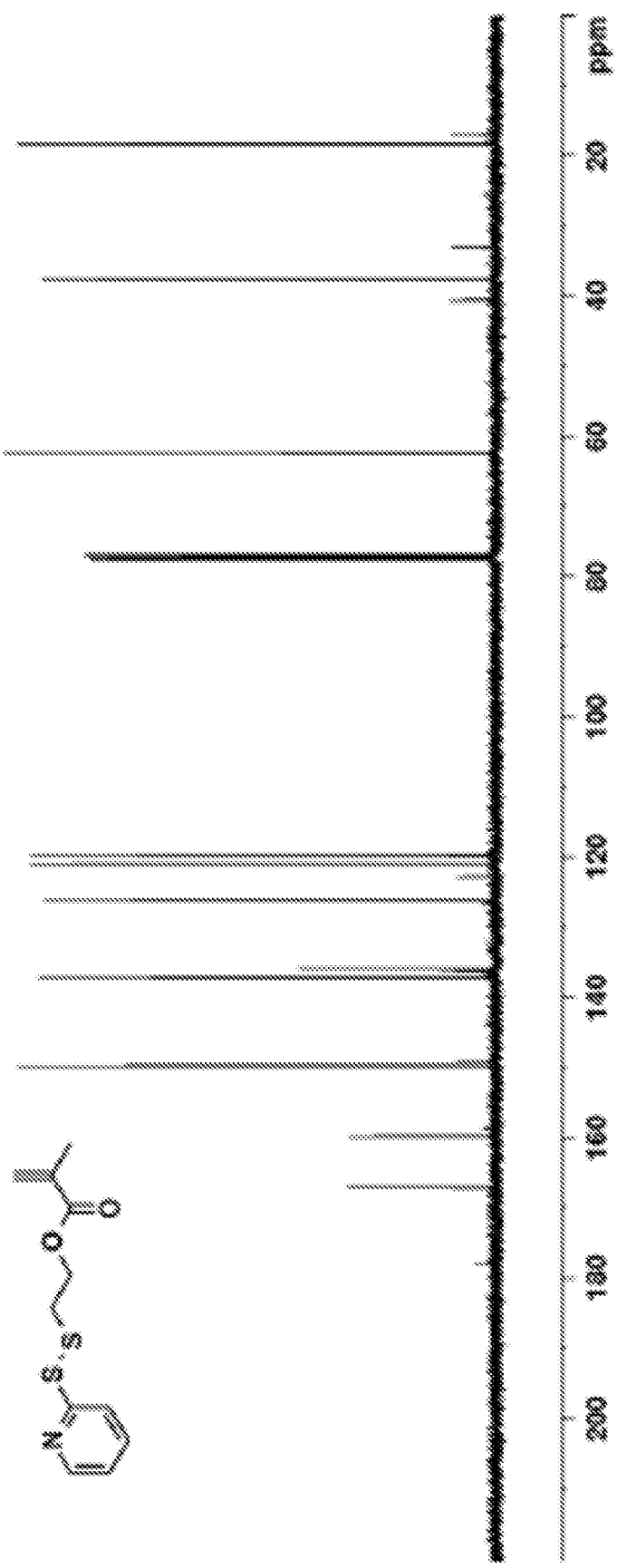
FIG. 11 is a $^{13}$C NMR spectrum of PDSMA in $CDCl_3$.

In vitro glucagon activity studies were carried out to assess the extent of bioactivity of thiolated glucagon compared to native glucagon (FIG. 7A, B). A commercially available assay kit containing hematopoietic rat cells expressing human glucagon receptor on the cell surface was utilized for these experiments. Using a four-parameter logistic fit, we obtained an EC50 value of $(128\pm7)\times10^{-9}$ m ($R^2$=0.99) for native glucagon and a value of $(197\pm20)\times10^{-9}$ m ($R^2$=0.99) for thiolated glucagon (FIG. 7A, B). While the value for glucagon is approximately tenfold higher than what has been reported previously using a different assay, the previously reported assay utilized a radioimmunoassay to study the effects of glucagon in pancreatic islet cells that naturally express the glucagon receptor. Thus, the systems are very different and not comparable. Most importantly, the signal response curves of glucagon and thiolated glucagon were similar. The chemical modification of glucagon resulted in a small shift in onset of signal, suggesting that the thiolated compound retained much of the bioactivity.

Additionally, glucagon nanogels also were active, suggesting the peptide is able to interact with its receptor even when covalently bound to polymer (FIG. 7C). While it is possible that the nanogels were taken up by cells and cleaved by glutathione present inside the cell, the released glucagon would need to be expelled from the cells in order to act on its extracellular receptor. Because the signal response was observed within seconds of compound addition, and endo- and exocytosis of nanoparticles has been reported to occur within minutes or hours, we believe the signal observed was elicited by the intact glucagon nanogels. Further, as mentioned previously, thiolation of glucagon resulted in a mixture of singly and doubly modified peptide and we anticipate that singly thiolated glucagon, or doubly thiolated glucagon that only added once, could be covalently conjugated to the outside of the nanogel, allowing for interaction with the receptor. After reduction of glucagon nanogels with $10\times10^{-3}$ m dithiothreitol (DTT), a stronger signal was observed at lower concentrations (0.003 mg mL$^{-1}$ nanogel), corresponding to release of glucagon from the interior of the nanogel, further strengthening our hypothesis.

These results demonstrated that we successfully synthesized a bioactive glucagon analog with reactive functional handles for easy conjugation and stabilization. The peptide with two thiols was an effective cross-linker for trehalose glycopolymers, forming encapsulated glucagon nanoparticles. Unlike glucagon, which aggregates within 24 h in solution, the nano particles stabilized the peptide for at least three weeks in solution. Furthermore, the nanoparticle stabilized the peptide at pH 7.4, whereas native glucagon quickly aggregates at neutral pH. The instability of glucagon in solution and the requirement to keep it in low pH are both difficulties in therapeutic administration of glucagon. Since glucagon is an important therapeutic, yet is limited by its solution instability, we believe this approach to trehalose glycopolymer nanoparticles is promising. Indeed, studies to examine the in vivo bioactivity for the treatment of hypoglycemia are underway. Moreover, this approach to utilize the combination of stabilizing trehalose glycopolymers and peptide/protein cross-linkers for high loadings may be effective forencapsulation and delivery of a variety of other biomolecules.response to PDSMA1-co-TrMA1.7 glucagon nanogels was also measured before and after reduction and compared to PEG-dithiol cross-linked nanogels. Data are shown as the average and standard error of the mean of two to six independent repeats. D) Cytotoxicity studies of PDSMA$_1$-co-TrMA$_{1.7}$ nanogels cross-linked with thiolated glucagon and PEG-dithiol with HDFs via live/dead assay indicate that nanogels are noncytotoxic up to 2.5 mg mL$^{-1}$. Data are shown as the average and standard deviation of three independent repeats. Detailed assay protocols can be found in the experimental and supporting information sections.

Example 7: Conclusions

The use of a modified glucagon to assemble and cross-link PDSMA-co-TrMA polymers into nanogels without the need for any additional reagents or cross-linkers is described. Nanogels were obtained with conjugation efficiency greater than 80%. Moreover, glucagon-nanogel conjugates exhibited superior stability in solution to aggregation compared to unencapsulated glucagon with the additional benefit of being soluble at both acidic and neutral pH. Glucagon release was observed under mild reducing conditions, suggesting that this encapsulation strategy may be a useful delivery vehicle. In addition to presenting a stabilizing nanogel system, we also synthesized a modified glucagon compound with a reactive functional handle. This modified glucagon was found to retain bioactivity both when conjugated and upon release, suggesting it may be a promising candidate for further study.

Example 8: Experimental Section

Polymerization of TrMA and PDSMA: For 1:1 PDSMA:TrMA (C6 regiosiomer) feed ratio, TrMA (65 mg, 0.16 mmol), PDSMA (40.4 mg, 0.16 mmol), and azobisisobutyronitrile (AIBN) (0.65, 0.004 mmol) were dissolved in DMF (0.60 mL) to give a [TrMA]:[PDSMA]:[initiator] ratio of 40:40:1. For 1 PDSMA: 3 TrMA (C6 regioisomer) feed ratio, TrMA (60 mg, 0.15 mmol), PDSMA (12.4 mg, 0.05 mmol), and AIBN (0.4 mg, 0.002 mmol) were dissolved in DMF (0.46 mL) to give a [TrMA]:[PDSMA]:[initiator] ratio of 20:60:1. The solutions were degassed by freeze-pump-thawing five times before initiating polymerization at 70° C. in an oil bath. The polymerizations were stopped after 5 and 6 h, respectively, by exposing the solutions to air. The resulting polymers were purified by precipitating once into ethyl acetate and dialyzing against water using 3.5 kDa molecular weight cutoff (MWCO) tubing for 2 d. The polymers were obtained in 60% and 70% yield after lyophilization, respectively. Monomer incorporation was calculated to be 0.8 to 1 and 1.7 to 1 by comparing the integration of the PDS protons (8.55-8.35 µm, 1H) to the CH3 protons (1.40-0.45 ppm) of the backbone by 1H NMR. Polymer Mn and dispersity (Đ) were determined via SEC to be 4900 Da and 2.90 for PDSMA1-co-TrMA0.8 and 9700 Da and 2.38 for PDSMA1-co-TrMA$_{1.7}$.

PDSMA-co-TrMA NMR (400 MHz, DMSO-d$_6$) δ 8.55-8.35 (CHN), 7.90-7.63 (aromatic), 7.28-7.14 (aromatic), 5.30-4.50 (trehalose OHs), 4.50-2.70 (CH2CH2O, CH2CH2O, CH2CHO, CHOH), 2.30-1.40 (CH2 polymer backbone), 1.40-0.45 (CH3, polymer backbone) ppm.

Representative Nanogel Formation with PEG-dithiol: PDSMA1-co-TrMA$_{0.8}$ (1 mg) was dissolved in 300 µL pH 7.4 PBS. A solution of 1 kDa PEG-dithiol (0.37 mg) was prepared separately in 10×10$^{-3}$ m HCl (200 µL). The two solutions were transferred to a glass vial equipped with a stir bar and mixed at 1000 rpm for 3 h. The resulting nanogel solution was purified using 10 kDa MWCO centriprep filters.

Representative Nanogel Formation with Thiolated Glucagon: Thiolated glucagon (0.1 mg, ≈1:1 singly to doubly thiolated peptide), lyophilized from 10×10$^{-3}$ m HCl, was dissolved in deionized water (100 µL). Separately, PDSMA1-co-TrMA0.8 (0.13 mg) or PDSMA1-co-TrMA1.7 (0.21 mg) was dissolved in 100 µL pH 7.4 PBS. The polymer solution along with additional 100 µL 10×10$^{-1}$ m HCl was transferred to a glass vial equipped with a stir bar. The solution was stirred at 1000 rpm, at which point the glucagon solution was added in dropwise. After stirring for 2 h, crude nanogels were purified using 30 kDa MWCO centriprep filters by centrifuging at 12 000 rpm for 20 min for three cycles. In between, the solution was replenished with 10×10$^{-3}$ m HCl then PBS.

Glucagon Activity Assay: A commercial assay kit containing Chem-1 cells expressing the human glucagon receptor was purchased from Eurofins (HTS112RTA) and used in conjunction with Fluo-8 dye kit from AAT Bioquest (36314). Cells were plated according to manufacturer's protocol for 96-well plate assay (2 vials of cells/96-well plate). After 24 h, media was removed from the wells and replaced with 100 µL dye solution, which was prepared according to manufacturer's instructions. Plates were incubated in the dark at 37° C. for 30 min and at 22° C. (room temperature) for an additional 30 min. Glucagon compounds were prepared in 0.05 m acetic acid, then diluted 1:10 into Hank's buffered saline solution without calcium, magnesium, or phenol red, supplemented with 1% DMSO and 10% v/v PBS. The thiolated glucagon sample used for these studies contained ≈1:1 singly to doubly thiolated peptide as characterized by LCMS. Measurements were carried out on a FlexStation II plate reader from Molecular Devices using the following conditions: Ex/Em: 490/525 nm; pipet height: 50 µL; pipet rate: 3 (78 µL s$^{-1}$); volume added: 10 µL at t=20 s; no mixing; assay duration: 80 s. A blank correction was applied to the data by subtracting the first data point (prior to ligand addition) from all subsequent data points. All data were expressed as the % maximum for each condition tested. A four-parameter logistic fit was applied to the results to obtain EC values. The mean and standard error of the mean of to six independent repeats were used for calculations.

Example 9: Synthesis of Pyridyl Disulfide Alcohol (PDSOH)

PDSOH was synthesized according to a previously published protocol as seen in Ghosh 2006. NMR (400 MHz, CDCl$_3$) δ 8.46-8.41 (m, 1H, CHN), 7.57-7.50 (m, 1H, CHCHCN), 7.40-7.36 (dt, 1H, CHCHCN), 7.12-7.07 (m, 1H, CHCHN), 5.83-5.50 (broad s, 1H, OH), 3.80-3.72 (2H, t, CH2OH), 2.94-2.86 (2H, t, CH2S) ppm; 13C NMR (400 MHz, CDCl3) δ 159.2, 149.8, 136.9, 121.9, 121.5, 58.4, 42.7 ppm.

Example 10: Synthesis of Pyridyl Disulfide Ethyl Metharcylate (PDSMA)

PDSMA was synthesized according to a previously published protocol as described by Ghosh 2006.

NMR (400 MHz, CDCl$_3$) δ 8.47-8.43 (m, 1H, CHN), 7.70-7.65 (m, 1H, CHCHCHN), 7.64-7.58 (m, 1H, CHCN), 7.11-7.05 (m, 1H, CHCHN), 6.13-6.09 (m, 1H, CHHC), 5.58-5.55 (m, 1H, CHHC), 4.42-4.35 (t, 2H, CH$_2$O, J=6.3 Hz), 3.10-3.05 (t, 2H, CH$_2$CH$_2$O, J 6.3 Hz), 1.94-1.90 (3H, s, CH$_3$) ppm; $^{13}$C NMR (400 MHz, CDCl$_3$) δ 167.0, 159.8, 149.8, 137.1, 136.0, 126.0, 120.9, 119.8, 62.4, 37.5, 18.31 ppm.

Example 11: Synthesis of Methacrylate Trehalose Monomer (TrMA)

Trehalose was added to 10 mL of anhydrous dimethylsulfoxide (DMSO) under argon and stirred 10-15 minutes to dissolve. Triethylamine was added to the stirring solution before adding methacrylic anhydride dropwise. The solution was stirred for 17 h at 21° C. during which time it turned a faint clear yellow color. To purify, the reaction solution was added to ice cold 8:2 hexanes/DCM (200 mL) and stirred for 5-10 minutes. The organic layer was decanted, leaving a sticky solid on the bottom of the flask, which was re-dissolved in deionized water (20 mL). The remaining organic solvent was removed via rotary evaporator prior to HPLC purification (C18 column, 20 ml/min flow, 10-60% MeOH, 20 min run). The product (C6 regioisomer), which had a retention time of 14 minutes, was collected and lyophilized to yield a white, fluffy solid. NMR (500 MHz, D2O) δ 6.06-6.01 (s, 1H, CHHCCH3), 5.65-5.61 (s, 1H, CHHCCH3), 5.08-5.02 (m, S8 2H, OCHO), 4.41-4.22 (m, 2H, COCH2CH), 3.99-3.36 (m, 10H, CH and CH2OH), 1.84-1.80 (s, 3H, CH3) ppm; 13C NMR (500 MHz, DMSO-d$_6$) δ 166.9, 136.5, 126.3, 93.7, 93.6, 73.3, 73.1, 72.1, 72.0, 70.7, 70.5, 70.1, 64.3, 61.2, 18.4 ppm.

TrMA (77 mg, 0.19 mmol) was dissolved in deioinized water (0.25 mL). Separately, AIBN was dissolved (0.48 mg, 0.003 mmol) was dissolved in DMF (0.25 mL). The two solutions were transferred to a Schlenk tube equipped with a stir bar. The solution was degassed through five freeze-pump-thaw cycles before initiation the polymerization at 70° C. in an oil bath. The polymerization was stopped after 10 hours by exposing the solution to air. The resulting polymer was purified by dialyzing against water using a 3.5 kDa MWCO tubing for two days. GPC was utilized to determine the Mn and Đ of 70 kDa and 7.33, respectively. Poly(TrMA) NMR (400 MHz, D2O) δ 5.33-4.90 (OCHO, 2H), 4.45-3.12 (trehalose protons, 7H), 2.25-1.40 (CH2, polymer backbone) 1.35-0.40 ppm (CH3, polymer backbone).

Example 12: TEM Imaging

TEM images were acquired on a FEI T12 instrument using formvar/carbon coated grids (200 mesh, Cu, Ted Pella). Grids were glow discharged for 15 seconds. 2.5 µL of sample were placed on the grid and allowed to adhere for 5 minutes. After, the grids were washed 3× with 1 drop of water, followed by staining with uranyl acetate.

Example 13: Excipient Stabilization of Glucagon

Glucagon was dissolved in 10 mM HCl to make a 5 mg/mL solution. Excipient solutions (50 mg/mL) were prepared by dissolving trehalose or poly(TrMA) in pH 7.4 PBS. The glucagon and excipient solutions were mixed in a 1:1 ratio to yield solutions with a final glucagon concentration of 2.5 mg/mL containing 10 weight equivalents of trehalose or polymer. Glucagon solution without additive was prepared using pH 7.4 PBS. For the duration of the experiment, glucagon solutions were kept in clear glass vials at 23° C. Solution stability was monitored using LC-MS at 0, 24, and 48 hour time points using the method described in the HPLC Methods section. The glucagon peak area at 280 nm was integrated for each time point per condition and expressed as a percent of the 0 h glucagon without additives peak area.

Example 14: Thiolation of Glucagon with Traut's Reagent

Glucagon (1 mg) was solubilized in 1:1 ACN/50 mM HCl (200 µL). 2-IT was dissolved in pH 9 PBS immediately before use (0.08 mg/50 µL). Glucagon solution (100 µL) and 2-IT solution (50 µL) plus an additional 300 µL pH 9 PBS were mixed in a 0.5 mL lo-bind tube for 90 min before analyzing sample via LCMS.

Example 15: Thiolation of Glucagon with DTBP

Glucagon (3 mg) was dissolved in 1 mL 0.1 M NaOH. Separately, DTBP (5 mg) was dissolved in 0.5 ml 100 mM borate buffer pH 9 and added to the glucagon solution. The solution was mixed for five minutes before adding additional DTBP (2 mg) in 0.2 mL borate buffer. The same addition was repeated two minutes later. After mixing for 40 minutes, DTBP (1 mg) in 0.1 mL borate buffer was added to the solution. Cloudiness developed in the solution over time, but the addition of 0.1 M NaOH caused the solution to return to clear. DTBP-modified glucagon was purified using 3 kDa MWCO centriprep filters, centrifuged at 12,000 rpm for 20 minute cycles. To reduce the disulfides, 10 mM TCEP was added to the solution and mixed for 10-15 minutes before continuing centriprep cycles until TCEP was completely removed.

Example 16: Ellman's Assay 5,5'-dithiobis-(2-nitrobenzoic acid (DTNB) (0.5 mg) was dissolved in pH 7.9 PBS+1 mM EDTA (1 mL). To each well of a polystyrene 96 well plate, 250 µL pH 7.9 PBS+1 mM EDTA, 10 µL DTNB solution were added followed by 25 µL sample solution. After letting the color develop, absorbance measurements were performed at 405 nm on ELX800 Universal Micoplate Reader. Results were reported as the average and standard deviation of three independent repeats.

Example 17: HPLC Method

An Eclipse XDB-C18 (4.6×150 mm, 5 µm) column was utilized to analyze glucagon thiolation using a gradient of 10-100% $H_2O$+0.1% TFA/ACN+0.1% TFA over 13 minutes. Glucagon and modified glucagon eluted at approximately 8.3 minutes.

Example 18: Gel Electrophoresis

Samples were loaded using 2× Laemmli sample buffer and run on Mini-Protean TGX, Any kD gels (Bio-Rad) at 180V for 25-30 minutes using Tris/Glycine/SDS buffer (Bio-Rad). Gels were stained with Coomassie.

Native-PAGE: Samples were loaded using native sample buffer (Bio-Rad) and run on Mini-Protean TGX, 4-20% gels (Bio-Rad) at 180V for 90 minutes using Tris/Glycine buffer (Bio-Rad). Gels were stained with Coomassie.

Example 19: Estimating Conjugation Yield

Conjugation yields were calculated using ImageJ software to compare glucagon band intensity before and after conjugation.

Example 20: Cytotoxicity Studies

The cell compatibility of the polymer and nanogel components to HDFs was evaluated using a LIVE/DEAD viability/cytotoxicity assay (Invitrogen). A control containing no polymer or nanogel was also prepared. Cells were cultured using fibroblast basal medium supplemented with a low serum growth kit (ATCC) at 37° C. with 5% $CO_2$. The cells were seeded in 96-well plates (BD Falcon) at a density of 1000 cells per well. After 24 hours, culture media was replaced with 100 µL media containing PDSMA-co-TrMA or PEG cross-linked nanogels and the cells were incubated for 24 hours. Cells were then washed with pre-warmed Dulbecco's phosphate buffered saline (D-PBS) and stained with LIVE/DEAD reagents (2 µM calcein AM and 4 µM ethidium homodimer-1). Fluorescent images of each well were captured on an Axiovert 200 microscope. The number of live (green) and dead (red) cells were counted, and % cell viability was calculated by dividing the number of live cells by the total number of live and dead cells. All experiments were performed a total of three times. The data is presented by normalizing each set to the control containing no additive.

RELATED PUBLICATIONS

[1] R. H. Unger, Diabetologia, 1985, 28, 574.//
[2] P. E. Cryer, S. N. Davis, H. Shamoon, Diabetes Care, 2003, 26, 1902.//
[3] C. D. Peterson, J. S. Leeder, S. Sterner, Drug Intell. Clin. Pharm., 1984, 18, 394.//
[4] J. R. Chabenne, M. A. DiMarchi, V. M. Gelfanov, R. D. DiMarchi, Biopolymers, 2011, 96, 468.//
[5] a) J. S. Pedersen, J. Diabetes Sci. Technol., 2010, 4, 1357; b) S. Onoue, K. Ohshima, K. Debari, K. Koh, S. Shioda, S. Iwasa, K. Kashimoto, T. Yajima, Pharm. Res., 2004, 21, 1274.//
[6] a) A. B. Joshi, L. E. Kirsch, J. Pharm. Sci., 2002, 91, 2332; b) N. Caputo, J. R. Castle, C. P. Bergstrom, J. M. Carroll, P. A. Bakhtiani, M. A. Jackson, C. T. Roberts, L. L. David, W. K. Ward, Peptides, 2013, 45, 40; c) L. Matilainen, S. L. Maunu, J. Pajander, S. Auriola, I. Jaaskelainen, K. L. Larsen, T. Jarvinen, P. Jarho, Eur. J. Pharm. Sci., 2009, 36, 412.//
[7] J. Chabenne, M. D. Chabenne, Y. Zhao, J. Levy, D. Smiley, V. Gelfanov, R. DiMarchi, Mol. Metab., 2014, 3, 293.//
[8] P. A. Mroz, D. Perez-Tilve, F. Liu, J. P. Mayer, R. D. DiMarchi, ACS Chem. Biol., 2016, 11, 3412.//
[9] a) P. Stigsnaes, S. Frokjaer, S. Bjerregaard, M. van de Weert, P. Kingshott, E. H. Moeller, Int. J. Pharm., 2007, 330, 89; b) C. Pinholt, J. T. Bukrinsky, S. Hostrup, S. Frokjaer, W. Norde, L. Jorgensen, Eur. J. Pharm. Biopharm., 2011, 77, 139.//
[10] M. J. Webber, E. A. Appel, B. Vinciguerra, A. B. Cortinas, L. S. Thapa, S. Jhunjhunwala, L. Isaacs, R. Langer, D. G. Anderson, Proc. Natl. Acad. Sci. U.S.A, 2016, 113, 14189.//
[11] F. Authier, B. Desbuquois, Cell. Mol. Life Sci., 2008, 65, 1880.//
[12] W. J. Fang, W. Qi, J. Kinzell, S. Prestrelski, J. F. Carpenter, Pharm. Res., 2012, 29, 3278.//
[13] a) S. Ohtake, Y. J. Wang, J. Pharm. Sci., 2011, 100, 2020; b) J. K. Kaushik, R. Bhat, J. Biol. Chem., 2003, 278, 26458.//
[14] H. Tapia, D. E. Koshland, Curr. Biol., 2014, 24, 2758.//
[15] H. Tapia, L. Young, D. Fox, C. R. Bertozzi, D. Koshland, Proc. Natl. Acad. Sci. U.S.A, 2015, 112, 6122.//
[16] N. Guo, I. Puhlev, D. R. Brown, J. Mansbridge, F. Levine, Nat. Biotechnol., 2000, 18, 168.//
[17] a) S. S. Kale, K. G. Akamanchi, Mol. Pharm., 2016, 13, 4082; b) N. K. Jain, I. Roy, Protein Sci., 2009, 18, 24; c) J. R. Wendorf, C. J. Radke, H. W. Blanch, Biotechnol. Bioeng., 2004, 87, 565.//
[18] A. Eroglu, M. J. Russo, R. Bieganski, A. Fowler, S. Cheley, H. Bayley, M. Toner, Nat. Biotechnol., 2000, 18, 163.//
[19] M. Sola-Penna, J. R. Meyer-Fernandes, Arch. Biochem. Biophys., 1998, 360, 10.//
[20] R. S. Herdeiro, M. D. Pereira, A. D. Panek, E. C. A. Eleutherio, Biochim. Biophys. Acta, 2006, 1760, 340.//
[21] M. Sakurai, Biological Functions of Trehalose as a Substitute for Water, in: K. Kuwajima, Y. Goto, F. Hirata, M. Kataoka, M. Terazima (Eds.) Water and Biomolecules, Springer 2009, pp. 219.//
[22] J. H. Crowe, J. F. Carpenter, L. M. Crowe, Annu. Rev. Physiol., 1998, 60, 73.//
[23] a) P. S. Belton, A. M. Gil, Biopolymers, 1994, 34, 957; b) G. Cottone, G. Ciccotti, L. Cordone, J. Chem. Phys., 2002, 117, 9862.//
[24] a) R. J. Mancini, J. Lee, H. D. Maynard, J. Am. Chem. Soc., 2012, 134, 8474; b) J. Lee, E. W. Lin, U. Y. Lau, J. L. Hedrick, E. Bat, H. D. Maynard, Biomacromolecules, 2013, 14, 2561; c) U. Y. Lau, S. S. Saxer, J. Lee, E. Bat, H. D. Maynard, ACS Nano, 2016, 10, 723; d) E. Bat, J. Lee, U. Y. Lau, H. D. Maynard, Nat. Commun., 2015, 6; e) E. M. Pelegri-O'Day, S. J. Paluck, H. D. Maynard, J. Am. Chem. Soc., 2017, 139, 1145.//
[25] Y. Liu, J. Lee, K. M. Mansfield, J. H. Ko, S. Sallam, C. Wesdemiotis, H. D. Maynard, Bioconjugate Chem., 2017,//
[26] a) T. M. O'Shea, M. J. Webber, A. A. Aimetti, R. Langer, Adv. Healthcare Mater., 2015, 4, 1802; b) J. Lee, J. H. Ko, E. W. Lin, P. Wallace, F. Ruch, H. D. Maynard, Polym. Chem., 2015, 6, 3443.//
[27] a) A. Sizovs, L. Xue, Z. P. Tolstyka, N. P. Ingle, Y. Y. Wu, M. Cortez, T. M. Reineke, J. Am. Chem. Soc., 2013, 135, 15417; b) Z. P. Tolstyka, H. Phillips, M. Cortez, Y. Y. Wu, N. Ingle, J. B. Bell, P. B. Hackett, T. M. Reineke, ACS Biomater. Sci. Eng., 2016, 2, 43.//
[28] A. V. Kabanov, S. V. Vinogradov, Angew. Chem. Int. Ed., 2009, 48, 5418.//
[29] J. H. Ryu, R. T. Chacko, S. Jiwpanich, S. Bickerton, R. P. Babu, S. Thayumanavan, J. Am. Chem. Soc., 2010, 132, 17227.//
[30] a) J. H. Ryu, S. Jiwpanich, R. Chacko, S. Bickerton, S. Thayumanavan, J. Am. Chem. Soc., 2010, 132, 8246; b) L. Y. Li, K. Raghupathi, C. H. Yuan, S. Thayumanavan, Chem. Sci., 2013, 4, 3654.//
[31] a) J. Ventura, S. J. Eron, D. C. Gonzalez-Toro, K. Raghupathi, F. Wang, J. A. Hardy, S. Thayumanavan, Biomacromolecules, 2015, 16, 3161; b) K. Dutta, D. Hu, B. Zhao, A. E. Ribbe, J. M. Zhuang, S. Thayumanavan, J. Am. Chem. Soc., 2017, 139, 5676.//
[32] N. M. Matsumoto, D. C. Gonzalez-Toro, R. T. Chacko, H. D. Maynard, S. Thayumanavan, Polym. Chem., 2013, 4, 2464.//
[33] S. Ghosh, S. Basu, S. Thayumanavan, Macromolecules, 2006, 39, 5595.//
[34] W. W. Bromer, L. G. Sinn, A. Staub, O. K. Behrens, J. Am. Chem. Soc., 1956, 78, 3858.//
[35] J. Sueirasdiaz, V. A. Lance, W. A. Murphy, D. H. Coy, J. Med. Chem., 1984, 27, 310.//
[36] M. Mokotoff, Y. M. Mocarski, B. L. Gentsch, M. R. Miller, J. H. Zhou, J. Chen, E. D. Ball, J. Pept. Res., 2001, 57, 383.//
[37] a) R. J. Christie, K. Miyata, Y. Matsumoto, T. Nomoto, D. Menasco, T. C. Lai, M. Pennisi, K. Osada, S. Fukushima, N. Nishiyama, Y. Yamasaki, K. Kataoka, Biomacromolecules, 2011, 12, 3174; b) M. J. Hunter, M. L. Ludwig, J. Am. Chem. Soc., 1962, 84, 3491.//
[38] V. Charulatha, A. Rajaram, J. Biomed. Mater. Res., 2001, 54, 122.//
[39] X. Yi, E. Batrakova, W. A. Banks, S. Vinogradov, A. V. Kabanov, Bioconjugate Chem., 2008, 19, 1071.//
[40] S. Ghodke, S. B. Nielsen, G. Christiansen, H. A. Hjuler, J. Flink, D. Otzen, FEBS J., 2012, 279, 752.//
[41] C. W. Chang, E. Bays, L. Tao, S. N. S. Alconcel, H. D. Maynard, Chem. Commun., 2009, 3580.//
[42] K. Moens, H. Heimberg, D. Flamez, P. Huypens, E. Quartier, Z. D. Ling, D. Pipeleers, S. Gremlich, B. Thorens, F. Schuit, Diabetes, 1996, 45, 257.//
[43] D. Montero, C. Tachibana, J. R. Winther, C. Appenzeller-Herzog, Redox Biol., 2013, 1, 508.//
[44] C. M. Koth, J. M. Murray, S. Mukund, A. Madjidi, A. Minn, H. J. Clarke, T. Wong, V. Chiang, E. Luis, A. Estevez, J. Rondon, Y. N. Zhang, I. Hotzel, B. B. Allan, Proc. Natl. Acad. Sci. U.S.A, 2012, 109, 14393.

[45] N. Oh, J. H. Park, Int. J. Nanomedicine, 2014, 9, 51.
[46] N. Boehnke, J. K. Kammeyer, R. Damoiseaux, H. D. Maynard, Adv. Funct. Mater., 2018, 28, 1705475
[47] N. Boehnke, J. K. Kammeyer, R. Damoiseaux, H. D. Maynard, Adv. Funct. Mater., 2018, 28, 201705475
[48] S. Ghosh, S. Basu, S. Thayumanavan, *Maromolecules* 2006, 39, 5595-5597.

The invention claimed is:

1. A trehalose-based nanogel, the nanogel comprising:
    (a) a copolymer comprising first units and second units, wherein
        (i) the first units comprise trehalose side chains; and
        (ii) the second units comprise disulfide side chains; and
    (b) dithiol cross-linkers;
    wherein the dithiol cross-linkers cross-link the copolymer through the disulfide side chains of the second units; and
    wherein the nanogel further comprises one biomolecule covalently bonded with the copolymer,
    wherein the biomolecule is used as a cross-linker.

2. The trehalose-based nanogel of claim 1, wherein
    (i) the first units are first methacrylate units comprising the trehalose side chains; and
    (ii) the second units are second methacrylate units comprising the disulfide side chains;
    wherein the dithiol cross-linkers cross-link the copolymer through the disulfide side chains of the second methacrylate units.

3. The trehalose-based nanogel of claim 2, wherein the nanogel has an average particle size in the range of 2-500 nm.

4. The trehalose-based nanogel of claim 3, wherein the nanogel has an average particle size in the range of 6-20 nm.

5. The trehalose-based nanogel of claim 2, wherein the copolymer has the structure of:

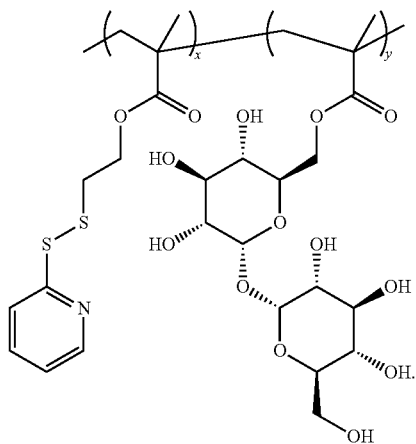

6. The trehalose-based nanogel of claim 1, wherein the biomolecule is glucagon.

7. The trehalose-based nanogel of claim 1, wherein the nanogel is biocompatible.

8. The trehalose-based nanogel of claim 1, wherein the biomolecule is controlled-releasable.

9. A Glucagon-containing nanogel, the nanogel comprising a trehalose-based copolymer comprising:
    a) a methacrylate-based backbone;
    b) at least one trehalose-based side chain;
    c) at least one disulfide side chain; and
    d) glucagons;
    wherein the glucagons are chemically modified to include more than one thiol and the glucagons cross link the disulfide side chains of the nanogel.

10. The Glucagon-containing nanogel of claim 9, wherein the nanogel has an average particle size in the range of 2-500 nm.

11. The Glucagon-containing nanogel of claim 10, wherein the nanogel has an average particle size in the range of 6-20 nm.

12. The Glucagon-containing nanogel of claim 9, wherein the nanogel is biocompatible.

13. The Glucagon-containing nanogel of claim 9, wherein the glucagons are controlled-releasable.

14. The Glucagon-containing nanogel of claim 9, wherein the trehalose-based copolymer comprises:

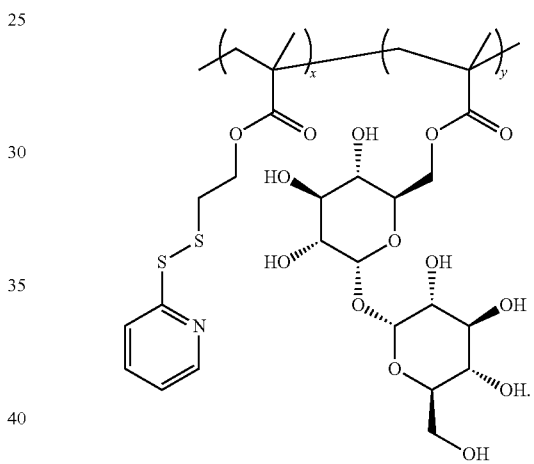

15. A method of making glucagon-containing nanogels, comprising the steps of:
    a) producing a copolymer comprising first methacrylate units and second methacrylate units, wherein the first methacrylate units comprise trehalose side chains; and the second methacrylate units comprise disulfide side chains;
    b) reacting glucagon with a thiolating agent to produce modified glucagon having more than one thiol; and
    c) conjugating the modified glucagon into the co-polymer to form glucagon-containing nanogels.

16. The method of claim 15, wherein the nanogel has an average particle size in the range of 2-500 nm.

17. The method of claim 15, wherein the nanogel is biocompatible or the glucagon are controlled-releasable.

* * * * *